US010638689B2

(12) United States Patent
Schaareman et al.

(10) Patent No.: US 10,638,689 B2
(45) Date of Patent: May 5, 2020

(54) **LETTUCE PLANTS COMPRISING RESISTANCE AGAINST *NASONOVIA RIBISNIGRI* BIOTYPE 1**

(71) Applicant: NUNHEMS B.V., Nunhem (NL)

(72) Inventors: Robert Theodorus Gerardus Schaareman, Roggel (NL); Vincent Pierre Andre Thomas, Aurillac (FR); Adrianus J. M. Van Der Arend, Monster (NL); Robert Johannes Martinus Raedts, Sevenum (NL); Olga Julian Rodriguez, Nunhem (NL)

(73) Assignee: NUNHEMS B.V., Nunhem (NL)

( * ) Notice: Subject to any disclaimer, the term of this patent is extended or adjusted under 35 U.S.C. 154(b) by 180 days.

(21) Appl. No.: 15/523,219

(22) PCT Filed: Oct. 29, 2015

(86) PCT No.: PCT/EP2015/075127
§ 371 (c)(1),
(2) Date: Apr. 28, 2017

(87) PCT Pub. No.: WO2016/066748
PCT Pub. Date: May 6, 2016

(65) Prior Publication Data
US 2017/0318770 A1    Nov. 9, 2017

(30) Foreign Application Priority Data
Oct. 30, 2014 (EP) .................................... 14191135

(51) Int. Cl.
*A01H 6/14* (2018.01)
*C12Q 1/6827* (2018.01)
*A01H 1/04* (2006.01)
*A01H 5/12* (2018.01)

(52) U.S. Cl.
CPC .............. *A01H 6/1472* (2018.05); *A01H 1/04* (2013.01); *C12Q 1/6827* (2013.01); *A01H 5/12* (2013.01)

(58) Field of Classification Search
None
See application file for complete search history.

(56) References Cited

U.S. PATENT DOCUMENTS

| 2011/0126308 A1 | 5/2011 | Thabuis et al. |
| 2012/0144513 A1 | 6/2012 | Van Schijndel |
| 2013/0239250 A1 | 9/2013 | Thabuis et al. |
| 2014/0289883 A1 | 9/2014 | Van Zee |

FOREIGN PATENT DOCUMENTS

| EP | 0921720 B2 | 5/2012 |
| WO | WO 2011/058192 A1 | 5/2011 |
| WO | WO-2011058192 A1 * | 5/2011 | ............ A01H 5/12 |
| WO | WO 2012/065629 A1 | 5/2012 |
| WO | WO 2012/066008 A1 | 5/2012 |

OTHER PUBLICATIONS

Cid et al (New sources of resistance to lettuce aphids in Lactuca spp. Arthropod-Plant Interactions 6:655-669, 2012).*
Gallois et al (Role of the Genetic Background in Resistance to Plant Viruses. Int. J. Mol. Sci. 19, 1-20, 2018) (Year: 2018).*
JI582884 (segeunce matches) (Year: 2011).*
Cid et al (New sources of resistance to lettuce aphids in *Lactuca* spp. Arthropod-Plant Interactions 6:655-669, 2012) (Year: 2012).*
Jeuken et al (Efficient QTL detection for nonhost resistance in wild lettuce: backcross inbred lines versus F2 population. Theor Appl Genet. 116:845-857, 2008) (Year: 2008).*
Zhang et al (QTLs for shelf life in lettuce co-locate with those for leaf biophysical properties but not with those for leaf developmental traits. Journal of Experimental Botany, vol. 58, No. 6, pp. 1433-1449, 2007) (Year: 2007).*
Allen et al., "Transcript-specific, single-nucleotide polymorphism discovery and linkage analysis in hexaploid bread wheat (*Triticum aestivum* L.)", Plant Biotechnology J. 2011, No. 9, pp. 1086-1099.
Arend et al., Eucarpia Leafy Vegetables '99. Palacky University, Olomouc, Czech Republic. 1999, pp. 149-157.
Cid et al., "New Sources of Resistance to Lettuce Aphids in *Lactuca* spp.", Arthropod-Plant Interactions, 2012, vol. 6, pp. 655-669.
Eenink et al., "Inheritance of resistance to the leaf aphid nasonovia ribis-nigri in the wild lettuce species lactuca virosa", Euphytica 1983, vol. 32, pp. 691-695.
Eenink et al., "Resistance of Lettuce (*Lactuca*) to the leaf aphid nasonovia ribis nigri I. Transfer of resistance from L. virosa to selection of resistant breeding lines", Euphytica 1982, vol. 31, pp. 291-299.
European Search Report issued in European Patent Application No. 14191135 dated Jan. 28, 2015 (9 pages).
Halmer, "Commercial seed treatment technology". In: Seed technology and its biological basis 2000, Eds: Black, M. and Bewley, J. D., pp. 257-286.
Henikoff et al., "Amino acid substitution matrices from protein blocks", PNAS 1992, vol. 89, pp. 10915-10919.
Hill et al., "Primed Lettuce Seeds Exhibit Increased Sensitivity to Moisture Content During Controlled Deterioration", HortScience 2007, vol. 42, No. 6, pp. 1436-1439.
Huang et al., "The genome of the cucumber, *Cucumis sativus* L.", Nature Genetics 2009, vol. 41, No. 12, p. 1275-1283.
International Search Report and Written Opinion issued in International Patent Application No. PCT/EP2015/075127 dated Feb. 4, 2016 (14 pages).

(Continued)

*Primary Examiner* — Ashley K Buran
*Assistant Examiner* — Wayne Zhong
(74) *Attorney, Agent, or Firm* — Arent Fox LLP

(57) ABSTRACT

The present invention relates to the field of lettuce breeding, in particular to Quantitative Trait Loci for resistance against the lettuce aphid *Nasonovia ribisnigri* biotype Nr:1 and to cultivated lettuce comprising one or more of these Quantitative Trait Loci.

13 Claims, 5 Drawing Sheets

Figure 1A:
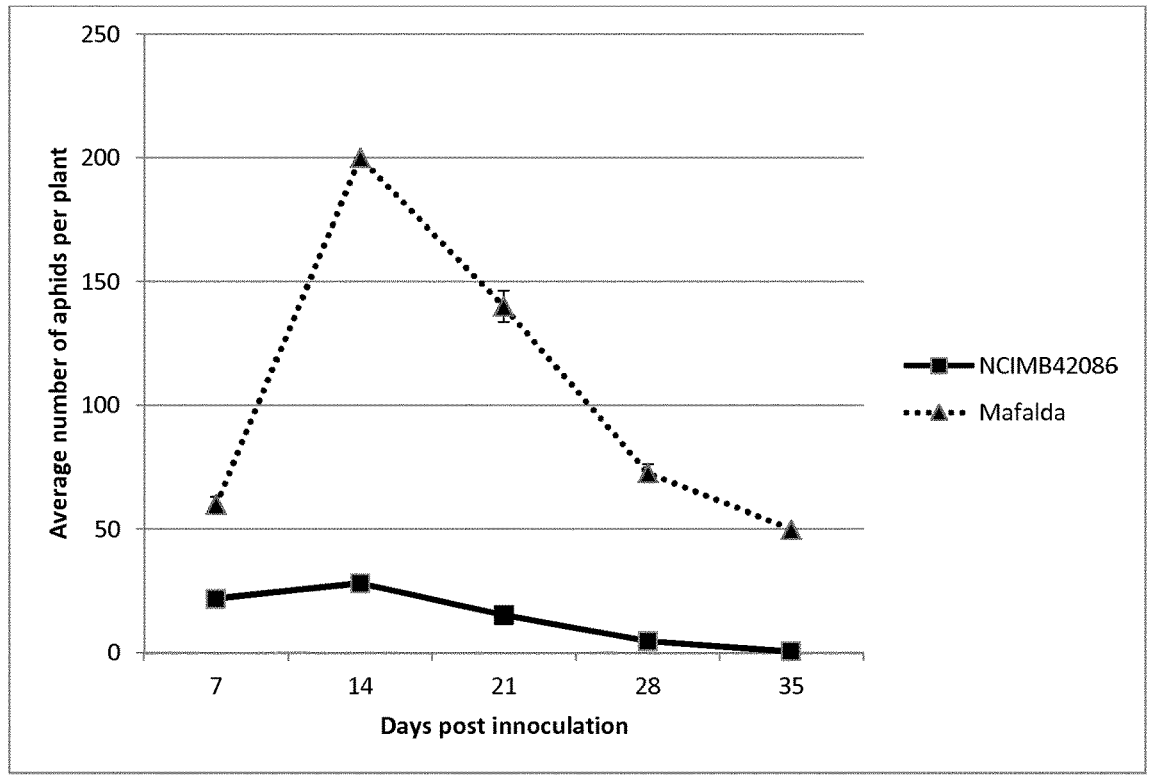

Specification includes a Sequence Listing.

(56) References Cited

OTHER PUBLICATIONS

Lebeda et al., Lebeda et al., Wild Lactuca Species, Their Genetic Diversity, Resistance to Diseases and Pests, and Exploitation in Lettuce Breeding, Eur J Plant Pathol, 2014, vol. 138, pp. 597-640.
Maisonneuve et al., "Sexual and somatic hybridization in the genus *Lactuca*", Euphytica, 1995, vol. 85, pp. 281-285.
Maisonneuve., "Utilisation de la culture in vitro d'embryons immatures pour les croisements interspécifiques entre Lactuca sativa L. et L. saligna L. ou L. virosa L.; étude des hybrides obtenus", Agronomie, 1987, vol. 7, No. 5, pp. 313-319.
McCreight et al., "Resistance to Lettuce Aphid (*Nasonovia ribisnigri*) Biotype 0 in Wild Lettuce Accessions PI 491093 and PI 274378", HortScience 2012, vol. 47, No. 2, pp. 179-184.
McCreight., "Potential Sources of Genetic Resistance in *Lactuca* spp. to the Lettuce Aphid, *Nasanovia ribisnigri* (Mosely) (Homoptera: Aphididae)", HortScience, 2008, vol. 43, No. 5, pp. 1355-1358.
Mou, "Mutations in lettuce improvement", International Journal of Plant Genomics, 2011, pp. 1-8.
Qi et al., "A genomic variation map provides insights into the genetic basis of cucumber domestication and diversity", Nature Genetics Dec. 2013, vol. 45, No. 12, pp. 1510-1518.
Resistance to the Lettuce leaf aphid Nasonovia ribisnigri, 4. Nov. 2008, IP.COM document 000176078D.
Teng et al., "Rapid Regeneration of Lettuce from Suspension Culture", HortScience 1992, vol. 27, No. 9, pp. 1030-1032.
Teng et al., "Regenerating Lettuce from Suspension Culture in a 2-Liter Bioreactor", HortScience 1993, vol. 28, No. 6, pp. 669-1671.
Thompson et al., "Descriptions and Pedigrees of Nine", US Dept Agric Tech Bul. No. 1224, 1961, pp. 1-19.
Verlaan et al., "Chromosomal rearrangements between tomato and Solanum chilense hamper mapping and breeding of the TYLCV resistance gene Ty-1", 2011, Plant Journal 68: 1093-1103.
Zhang et al., "Genotypic effects on tissue culture response of lettuc cotyledons", Journal of Genetics and Breeding 1992, vol. 46, No. 3, pp. 287-290.

\* cited by examiner

LETTUCE PLANTS COMPRISING RESISTANCE AGAINST *NASONOVIA RIBISNIGRI* BIOTYPE 1

CROSS REFERENCE TO RELATED APPLICATIONS

This application is a 35 U.S.C. 371 National Phase of PCT Application No. PCT/EP2015/075127 filed Oct. 29, 2015, which claims benefit to European Patent Application No. 14191135.4 filed Oct. 30, 2014, the disclosure of which is hereby incorporated by reference in its entirety.

FIELD OF THE INVENTION

The present invention relates to cultivated lettuce (*Lactuca sativa*) seeds, plants and plant parts comprising one or more introgression fragments from a wild lettuce, such as *Lactuca virosa*, on chromosome 6 and/or chromosome 7, whereby the introgression fragment comprises a Quantitative Trait Locus (QTL) for resistance against *Nasonovia ribisnigri* biotype 1 (also called herein Nr:1 or biotype Nr:1), referred to as QTL6.1 (for the QTL on chromosome 6) and QTL7.1 and 7.2 (for two QTLs on chromosome 7). The present invention also relates to cultivated lettuce (*Lactuca sativa*) seeds, plants and plant parts grown from the seeds, that are resistant to *Nasonovia ribisnigri* biotype 1 due to the presence of an introgression fragment from *L. virosa* comprising QTL6.1 and/or QTL7.1 (and/or QTL7.2) as well as to progenies of the plants and propagation material for producing the plants. The invention further relates to wild lettuce sources of the resistance-conferring QTLs for use in breeding Nr:1 resistant lettuce plants.

BACKGROUND OF THE INVENTION

The lettuce aphid (*Nasonovia ribisnigri* (Mosley)) is a major pest occurring in lettuce worldwide. The problem started to be severe for lettuce production in the 1970's in North Western Europe and spread rapidly all across Europe. Then, in the 1980's, the aphid was detected in Canada. Later on, the problem was reported in the USA (California and Arizona). More recently, the lettuce aphid was found in New Zealand and Australia.

Lettuce aphids can colonize lettuce plants at any plant stage and feed preferably from younger leaves. Large amount of aphids on the plant are able to reduce plant growth and deform the shape of the head so that the lettuce heads are then not marketable. The presence of high amounts of aphids in lettuce heads is a reason for retailers to refuse to buy lettuce from growers. At young plant stage it is possible to control the lettuce aphid using insecticide. Several products were reported to be efficient in controlling aphid populations. However, resistance to chemicals were reported in some aphid populations. Moreover, at older developmental stages it is not possible to control aphids using insecticides, as chemical products cannot enter into the lettuce head.

Since 2007, two biotypes of lettuce aphid have been known in Europe, which were designated biotype Nr:0 and Nr:1. Complete and partial resistance against *Nasonovia ribisnigri* biotype Nr:0 were found in *Lactuca virosa*, a wild relative of lettuce (Eenink and Dieleman, Euphytica 32(3), 691-695 (1982)). The complete resistance was due to a single dominant gene, termed the Nr gene. The Nr gene was transferred from *L. virosa* accession IVT280 into cultivated *L. sativa* and was highly effective (Arend et al. 1999, Eucarpia Leafy Vegetables '99. Palacky University, Olomouc, Czech Republic, p 149-157).

However, breeders experienced that the release of varieties resistant to lettuce aphid was not straightforward. The Nr resistance gene was found tightly linked to recessive genes conferring strong negative side-effects. Plants homozygous for the Nr gene showed a reduced growth, a lighter green colour and accelerated degradation of chlorophyll in the older leaves. This negative phenotype was also referred to as the "Compact Growth and Rapid Ageing" phenotype or "CRA phenotype" and it was possible to find recombinant lettuce plants in which the Nr gene was present in homozygous form, but in which the CRA phenotype was not expressed (see, e.g., EP 0921720 B1). These recombinant plants, in which a recombination event (i.e. meiotic crossing-over) had taken place between the Nr gene and the linked recessive genes, served as the source of the Nr resistance gene that was not linked to the negative side-effect phenotype.

The Nr resistance gene from IVT280 (CGN04683) is widely used in commercial lettuce cultivars, such as cultivars 'Barcelona', 'Mafalda' (both Nunhems B.V.) and many others.

Other sources of biotype Nr:0 resistance are still being sought, as the wide-scale use of a single resistance gene faces the threat of resistance breakdown. Genes which have different resistance mechanisms can be effectively employed in such circumstances. For example new biotype Nr:0 resistance genes were found in an *L. serriola* accessions PI 491093 and in an *L. virosa* accession PI 274378 (Mc Creight 2008 HortScience 43:1355-1358; McCreight and Liu (2012), HortScience 47(2):179-184). The resistance found in PI274378 was found to be complete and allelic to the Nr gene from IVT280. In PI49093 partial resistance was found, and the authors proposed to designate this resistance allele $Nr0^P$ (in contrast to $Nr0^C$ for the complete resistance allele found in PI274378). They suggested using this partial resistance allele in areas where the complete resistance allele has not yet been widely employed in order to delay or prevent emergence of aphid biotypes that overcome Nr resistance.

Also resistance against *Nasonovia ribisnigri* biotype Nr:1 is sought after. Different resistance genes and resistance mechanisms are also desired regarding Nr:1, to prolong the use of resistance genes. When large scale use is made of one resistance gene, which has a certain resistance mechanism, the chances are high that resistance will be overcome by the aphid population, as happened in 2007 for the Nr gene in Europe, when the new *Nasonovia ribisnigri* biotype Nr: 1 appeared. Thus, the current situation is that the aphid biotype Nr:0 can still be controlled by the single Nr gene derived from the IVT *L. virosa* accession (for example in the USA, where biotype Nr:1 does not yet occur), but that this gene is ineffective against aphid biotype Nr:1 found in Europe. The Nr: 1 biotype was first found only in central Europe, but is now spreading to other areas and in 2010 has also been found in fields in Spain (Cid et al. 2012, Arthropod-Plant Interactions 6: 655-669).

Several publications describe sources which are suggested to contain a resistance gene against lettuce aphid biotype Nr:1. For example three accessions (CGN13361, CGN16266, CGN16272) were described to be resistant against both aphid biotypes Nr:0 and Nr:1 (Anonymous, 4, Nov. 2008, IP.COM document 000176078) and were suggested to be used in breeding for combined Nr:0 and Nr:1 resistant lettuce. In this article *L. virosa* accessions CGN16272 and CGN16266 are said to be used in backcrossing programs with cultivar Daguan (Syngenta) and cultivar Funly (Syngenta), respectively (both these cultivars lack *Nasonovia* resistance genes), and the offspring are said to show a resistance similar to the resistance of the donor accessions. Also markers for the resistance gene of CGN16272 are said to be developed from crosses of CGN16272 with cultivar Cobham Green (Anonymous, 4, Nov. 2008, supra). These three accessions were also analyzed in Cid et al. (2012, supra) and were found to comprise high Nr:0 resistance but only partial biotype Nr:1 resistance.

Cid et al. (2012, supra) also identified three *L. virosa* accessions with some resistance against both biotypes Nr:1 and Nr:0, namely CGN16274, CGN21399 and CGN05148. In this study, the authors aim was to find resistance against both lettuce aphid biotypes, Nr: 0 and Nr: 1, in single wild *Lactuca* accession. However, aphids of biotype Nr:1 are still able to feed and reproduce on these wild accessions, albeit to a lower extent than on the susceptible controls (see FIG. 4).

WO2011/058192 reports *L. serriola* 10G.913571 as being resistant against biotype Nr:1, although no data are provided to substantiate this claim and no indication of the level of resistance and methods to determine this is given.

WO2012/066008 and WO2012/065629 also report Nr: 1 resistance from an *L. serriola* accession to be transferred into a bulk seed sample designated 10G.913569. Again, no data are provided and no indication on the resistance level and methods to determine resistance is given.

Thus, in the prior art, such as Anonymous 2008, above, and Cid et al. 2012, above, only a few wild accessions are identified on which the amount of Nr: 1 aphids is reduced to some extent and no genetic basis is provided.

There remains a need for identifying genes which can confer resistance against biotype Nr:1 in order to develop cultivated lettuce comprising Nr:1 resistance. The instant inventors looked for accessions which were thought to be susceptible to aphids of biotype Nr:0, in order to identify (new) resistance gene(s) against biotype Nr: 1 in these accessions. In addition, they also looked for the identification of genes which can confer both free-choice and non-choice resistance. They found a *L. virosa* accession (of which a representative sample of seeds was deposited under NCIMB42086) comprising high levels of resistance against biotype Nr:1, both under free choice and non-choice conditions, and decided to try to map the resistance, in order to identify how many and which *L. virosa* genome regions are responsible for conferring Nr:1 resistance.

When trying to map the resistance, the inventors encountered severe problems in creating a population of plants useable for QTL mapping (i.e. a mapping population which consists of individuals that have undergone chromosomal meiotic recombination between the *L. sativa* and *L. virosa* genomes). The reason is likely that the chromosomes of *L. virosa* and *L. sativa*, which are two different species, are quite different, leading to crossing barriers and infertility, as well as potential problems during meiosis and crossing over. No useable F2 populations could be generated, and only after many crosses with various recurrent parents the inventors succeeded in generating large enough backcross families which could be used in mapping studies. These mapping populations were also not easy to analyze using molecular markers and phenotyping, i.e. it was quite surprising that the inventors managed to generate a genetic map with SNP markers that are polymorphic between the recurrent parent and the *L. virosa* accession, and were also able to map *Nasonovia* Nr:1 resistance onto that map.

Surprisingly, in the initial QTL mapping study (using a BC1 population) they did not find a single gene, but three genomic regions (of which only two were later also found in a different backcross population) on two different chromosomes of *L. virosa* which contribute to the Nr:1 resistance. Both controlled environment inoculations (free choice and non-choice) and field data (also free choice and non-choice) showed high levels of Nr:1 resistance, against three geographically distinct Nr:1 biotypes (Germany, France and Spain). In fact, in field evaluations in Spain (Murcia) semi-adult and adult plants of the accession NCIMB42086 did not have any Nr:1 aphids on their leaves in both free-choice and non-choice tests.

In the later mapping study, two of the QTLs (QTL6.1 and QTL7.1) were found again and the QTL region could be narrowed down. This second mapping study does not invalidate the results of the first study, and all three QTLs are encompassed herein.

It is an object of the invention to provide three QTLs (designated QTL6.1, QTL7.1 and/or QTL7.2) from *L. virosa* which can be used to generate cultivated lettuce plants comprising resistance against biotype Nr:1.

It is also an object of the invention to provide cultivated lettuce plants comprising one or two or three QTLs (QTL6.1 and/or QTL7.1 and/or QTL7.2) introgressed from a wild lettuce, such as *L. virosa*, into the *L. sativa* genome, whereby the introgressions confer resistance against biotype Nr: 1.

Thus, different cultivated lettuce plants are encompassed herein: a) cultivated lettuce plants comprising only one QTL conferring Nr:1 resistance, selected from QTL6.1, QTL7.1 and QTL7.2; b) cultivated lettuce plants comprising two QTLs conferring Nr:1 resistance selected from QTL6.1 and QTL7.1 and QTL7.2 (in one aspect a plant comprising both QTL6.1 and QTL7.1 is a specific embodiment); c) cultivated lettuce plants comprising three QTLs conferring Nr:1 resistance selected from QTL6.1, QTL7.1 and QTL7.2.

It is also an object of the invention to provide cultivated lettuce plants comprising one or two QTLs selected from QTL6.1 and QTL7.1 introgressed from a wild lettuce, such as *L. virosa*, into the *L. sativa* genome, whereby the introgressions confer resistance against biotype Nr: 1.

In one aspect the QTLs are obtainable from (are as in) seeds deposited under accession number NCIMB42086. The introgression fragment(s) comprising the QTL(s) is/are detectable by a molecular marker assay which detects at least 1, 2, 3, 4, or more markers. In another aspect the QTLs are obtainable from (are as in) other Nr:1 resistant wild lettuce accessions, especially in *L. virosa* accessions, whereby the introgression fragment(s) is/are detectable by a molecular marker assay which detects at least 1, 2, 3, 4, or more (i.e. 5, 6, 7, 8, 9, 10, 11, 12, or more) markers disclosed herein. In one aspect the *L. virosa* accession is one of two types of accessions, and the introgression fragment comprises a *L. virosa* accession specific SNP marker (named VSP for *Virosa* Specific), selected from VSP1 and VSP2, both specific for one *L. virosa* accession and VSP3 and VSP4, both specific for another *L. virosa* accession.

Despite problems in interspecific QTL mapping mentioned above, like infertility, segregation distortion, etc., the originally found QTL regions (which were originally mapped to a physical region spanning 60 to 240 Mb on chromosome 6; and 170 to 235 Mb on chromosome 7 for QTL7.1; and 70 to 150 Mb for QTL 7.2) could be mapped to a region spanning 77 Mb to 161 Mb on chromosome 6 (comprising QTL6.1) and 203 Mb to 219 Mb on chromosome 7 comprising QTL7.1.

Thus, in one aspect a cultivated *Lactuca sativa* plant is provided comprising an introgression fragment on chromosome 6 (comprising QTL6.1) and/or on chromosome 7

(comprising QTL7.1), each in homozygous or heterozygous form, wherein said introgression fragment confers resistance against *Nasonovia ribisnigri* biotype 1 (Nr:1). In one aspect the introgression fragment comprises all or part of the region starting at 77 Mb on chromosome 6 and ending at 161 Mb on chromosome 6 and/or the introgression fragment comprises all or part of the region starting at 203 Mb on chromosome 7 and ending at 219 Mb on chromosome 7. See e.g. FIG. 3B, showing *L. sativa* chromosomes 6 and 7, where the gray bars illustrate the introgression fragments from a wild Nr:1 resistant accession, such as a *L. virosa* accession (e.g. NCIMB42086) comprising the resistance conferring QTLs QTL6.1 and QTL7.1, or variants thereof. In one aspect an introgression fragment comprising QTL7.2 may also optionally be present in the cultivated lettuce plant.

It is understood that a smaller introgression fragment (i.e. comprising a resistance conferring part of the above mentioned region spanning 77 Mb to 161 Mb of chromosome 6) which retains the QTL6.1 (or variant) may be a fragment having a size of 80 Mb, 70 Mb, 60 Mb, 50 Mb, 40 Mb, 30 Mb, 20 Mb, 10 Mb, 5 Mb, 2.5 Mb, 2 Mb, 1 Mb, 0.5 Mb, 100 kb, 50 kb or less and comprise the QTL6.1 or a variant thereof. In one aspect the part is at least 5 kb, 10 kb, 20 kb in size, or more.

It is further understood that a smaller introgression fragment (i.e. comprising a resistance conferring part of the above mentioned region spanning 203 Mb to 219 Mb of chromosome 7) which retains the QTL7.1 (or variant) may be a fragment having a size of 15 Mb, 10 Mb, 5 Mb, 2.5 Mb, 2 Mb, 1 Mb, 0.5 Mb, 100 kb, 50 kb or less and comprise the QTL7.1 or a variant thereof. In one aspect the part is at least 5 kb, 10 kb, 20 kb in size, or more.

In one aspect, the introgression fragment on chromosome 6 is detectable by a molecular marker assay which detects at least one, preferably at least 2 or 3 or 4 or 5 (or more) of the markers selected from the group consisting of:

a) The CC or CT genotype for the Single Nucleotide Polymorphism marker SNP1.23 in SEQ ID NO: 23 (or in a sequence comprising substantial sequence identity to SEQ ID NO: 23);

b) the CC or CT genotype for the Single Nucleotide Polymorphism marker SNP_02 in SEQ ID NO: 2 (or in a sequence comprising substantial sequence identity to SEQ ID NO: 2);

c) the TT or CT genotype for the Single Nucleotide Polymorphism marker SNP2.24 in SEQ ID NO: 24 (or in a sequence comprising substantial sequence identity to SEQ ID NO: 24);

the AA or AC genotype for the Single Nucleotide Polymorphism marker SNP_03 in SEQ ID NO: 3 (or in a sequence comprising substantial sequence identity to SEQ ID NO: 3);

d) any wild lettuce genome specific marker, especially *L. virosa*-genome specific marker, located physically in-between SNP1.23 and SNP_03 (e.g. in-between SNP1.23 and SNP2.24, SNP1.23 and SNP_02); or in between SNP_02 and SNP_03 (e.g. in-between SNP_02 and SNP2.24); or in between SNP2.24 and SNP_03;

e) any wild lettuce genome specific marker especially *L. virosa*-genome specific marker, located within a distance of 10 Mb, preferably within 5 Mb, of any marker selected from SNP1.23, SNP_02, SNP2.24, or SNP_03.

Optionally, in one aspect, the introgression fragment comprises (and is detectable by) a *L. virosa* accession specific marker selected from the GG or GT genotype for the Single Nucleotide Polymorphism marker VSP1 in SEQ ID NO: 26 (or in a sequence comprising substantial sequence identity to SEQ ID NO: 26) and the AA or AC genotype for the Single Nucleotide Polymorphism marker VSP3 in SEQ ID NO: 27 (or in a sequence comprising substantial sequence identity to SEQ ID NO: 27). Using the SNP markers VSP1 and VSP3 the introgression fragments comprising QTL6.1 from two different *L. virosa* type accessions can be distinguished.

In another aspect, the introgression fragment at the far end of chromosome 7 comprising QTL 7.1 (at a physical position between 203 Mb and 219 Mb of chromosome 7) is detectable by a molecular marker assay which detects at least one, preferably at least 2 or 3 or 4 or 5 (or more) of the markers selected from the group consisting of:

a. the TT or TC genotype for the Single Nucleotide Polymorphism marker SNP_17 in SEQ ID NO: 17 (or in a sequence comprising substantial sequence identity to SEQ ID NO: 17);

b. the TT or TC genotype for the Single Nucleotide Polymorphism marker SNP17.25 in SEQ ID NO: 25 (or in a sequence comprising substantial sequence identity to SEQ ID NO: 25);

c. the GG or GC genotype for the Single Nucleotide Polymorphism marker SNP_18 in SEQ ID NO: 18 (or in a sequence comprising substantial sequence identity to SEQ ID NO: 18);

d. the GG or GA genotype for the Single Nucleotide Polymorphism marker SNP_19 in SEQ ID NO: 19 (or in a sequence comprising substantial sequence identity to SEQ ID NO: 19);

e. any wild lettuce genome specific marker, especially *L. virosa*-genome specific marker, located physically in-between SNP_17 and SNP_19 (e.g. in-between SNP_17 and SNP_18, in between SNP_17 and SNP17.25; or in between SNP17.25 and SNP_19, or in between SNP17.25 and SNP_18, or in between SNP_18 and SNP_19);

f. any wild lettuce genome specific marker especially *L. virosa*-genome specific marker, located within a distance of 12 Mb, 10 Mb, preferably within 5 Mb, of any marker selected from SNP_17, SNP_17.25, SNP_18 and SNP_19.

Optionally, in one aspect, the introgression fragment comprises (and is detectable by) a *L. virosa* accession specific marker selected from the CC or AC genotype for the Single Nucleotide Polymorphism marker VSP2 in SEQ ID NO: 28 (or in a sequence comprising substantial sequence identity to SEQ ID NO: 28) and the GG or GA genotype for the Single Nucleotide Polymorphism marker VSP4 in SEQ ID NO: 29 (or in a sequence comprising substantial sequence identity to SEQ ID NO: 29). Using the SNP markers VSP2 and VSP4 the introgression fragments comprising QTL7.1 from two different types *L. virosa* accessions can be distinguished.

When referring to the introgression fragment being "detectable by a molecular marker assay which detects" one or more markers, this means that the introgression fragment comprises the resistance genotype of that marker.

In a further aspect, seeds, plants and plant parts or cultivated lettuce comprising an introgression fragment from a wild lettuce, such as from *L. virosa*, comprising QTL6.1 and/or QTL7.1 (and optionally QTL7.2) is provided, whereby the introgression fragment confers resistance against *Nasonovia ribisnigri* biotype Nr:1. In one aspect the introgression fragment is from *L. virosa*, especially from *L. virosa* accessions comprising Nr:1 resistance in both free choice and non-choice tests as described herein. In one aspect the introgression fragment is from accession NCIMB42086 or is obtainable from accession NCIMB42086, or progeny or descendants thereof.

In another aspect the introgression fragment is from a *L. virosa* accession which comprises the following *L. virosa* accession specific SNP markers: the GG genotype (homozygous) or GT genotype (heterozygous) at nucleotide 71 of SEQ ID NO: 26 (or in a sequence comprising substantial sequence identity to SEQ ID NO: 26), named the VSP1 marker; and the CC genotype (homozygous) or AC genotype (heterozygous) at nucleotide 71 of SEQ ID NO: 28 (or in a sequence comprising substantial sequence identity to SEQ ID NO: 28), named VSP2. VSP1 and VSP2 are found in Nr:1 resistant accessions, such as NCIMB42086.

In another aspect the introgression fragment is from a *L. virosa* accession which comprises the following *L. virosa* accession specific SNP markers: the AA genotype (homozygous) or AC genotype (heterozygous) at nucleotide 71 of SEQ ID NO: 27 (or in a sequence comprising substantial sequence identity to SEQ ID NO: 27), named the VSP3 marker; and the GG genotype (homozygous) or AG genotype (heterozygous) at nucleotide 71 of SEQ ID NO: 29 (or in a sequence comprising substantial sequence identity to SEQ ID NO: 29), named VSP4. VSP3 and VSP4 are found in other Nr: 1 resistant accessions.

Also methods for making and/or identifying and/or selecting cultivated lettuce plants comprising an introgression from wild lettuce, such as from *L. virosa*, on chromosome 6 (comprising QTL6.1) and/or chromosome 7 (comprising QTL 7.1 and/or QTL7.2) are provided, as are methods for transferring QTLs to different cultivated lettuce plant lines or varieties, especially to Nr:1 susceptible lettuce lines or varieties.

Definitions

The indefinite article "a" or "an" does not exclude the possibility that more than one of the element is present, unless the context clearly requires that there be one and only one of the elements. The indefinite article "a" or "an" thus usually means "at least one".

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one or two or three loci or genes (or phenotypic characteristics due to these specific loci or genes), but which can otherwise differ from one another enormously as regards the other loci or genes in the genome.

"Lettuce" or "cultivated lettuce" or "cultivated *Lactuca sativa*" refers herein to plants of the species *Lactuca sativa* L. (or seeds from which the plants can be grown), and parts of such plants, bred by humans for food and having good agronomic characteristics. This includes any cultivated lettuce, such as breeding lines (e.g. backcross lines, inbred lines), cultivars and varieties of any type. Generally heading and non-heading types of lettuce are distinguished. Heading types include for example crisphead, butterhead and romaine (cos) types, while non-heading types include leaf-types. Cultivated lettuce plants are not "wild lettuce" plants or "wild *Lactuca*" plants, i.e. plants which generally have much poorer yields and poorer agronomic characteristics than cultivated plants and e.g. grow naturally in wild populations.

"Wild lettuce" or "wild *Lactuca*" accessions refers to plants of species other than cultivated *Lactuca sativa*, such as *Lactuca virosa, Lactuca serriola, Lactuca saligna, Lactuca perennis*, and others. Preferably, such wild lettuce comprises or consists of *Lactuca* species which are cross fertile with *L. sativa*, optionally with the aid of embryo rescue techniques (see Maisonneuve 1987, Agronomique 7: 313-319 and Maisonneuve et al. 1995, Euphytica 85:281-285) and/or chromosome doubling techniques (Thompson and Ryder 1961, US Dept Agric Tech Bul. 1224), or methods whereby genes can be transferred into *L. sativa* via a bridge species, such as *L. serriola* (Eenink et al. 1982, supra).

As used herein, the term "plant" includes the seed (from which the plant can be grown), the whole plant or any parts such as plant organs (e.g., harvested or non-harvested leaves, etc.), plant cells, plant protoplasts, plant cell- or tissue cultures, plant callus, plant cell clumps, plant transplants, seedlings, plant cells that are intact in plants, plant clones or micro-propagations, or parts of plants (e.g., harvested tissues or organs), such as plant cuttings, vegetative propagations, embryos, pollen, ovules, flowers, leaves, heads, seeds (produced on the plant after self-fertilization or cross-fertilization), clonally propagated plants, roots, stems, stalks, root tips, grafts, parts of any of these and the like, or derivatives thereof, preferably having the same genetic make-up (or very similar genetic make-up) as the plant from which it is obtained. Also any developmental stage is included, such as seedlings, cuttings prior or after rooting, mature and/or immature plants or mature and/or immature leaves. When "seeds of a plant" are referred to, these either refer to seeds from which the plant can be grown or to seeds produced on the plant, after self-fertilization or cross-fertilization.

"Somatice cells" and "reproductive cells" can be distinguished, whereby somatic cells are cells other than gametes (e.g. ovules and pollen), germ cells and gametocytes. Gametes, germ cells and gametocytes are "reproductive cells".

"Tissue Culture" or "cell culture" refers to an in vitro composition comprising isolated cells of the same or a different type or a collection of such cells organized into plant tissue. Tissue cultures and cell cultures of lettuce, and regeneration of lettuce plants therefrom, is well known and widely published (see, e.g., Teng et al., HortScience. 1992, 27(9): 1030-1032 Teng et al., HortScience. 1993, 28(6): 669-1671, Zhang et al., Journal of Genetics and Breeding. 1992, 46(3): 287-290).

"Harvested plant material" refers herein to plant parts (e.g., leaves, leaf parts or heads detached from the whole plant) which have been collected for further storage and/or further use.

"Harvested seeds" refers to seeds harvested from a line or variety, e.g., produced after self-fertilization or cross-fertilization and collected.

"Harvested leaves" or "harvested heads" as used herein refers to lettuce leaves, or leaf parts or heads, i.e., the plant without the root system, for example substantially all (harvested) leaves. Leaves may be whole or cut into parts.

"Progeny" or "progenies" or "descendants" as used herein refers to offspring, or the first and all further descendants derived from (obtained from) (derivable from or obtainable from) a plant of the invention that comprises (retains) the one or more Nr:1 resistance conferring QTLs in homozygous or heterozygous form and/or the Nr:1 resistance phenotype described herein. Progeny may be derived by regeneration of cell culture or tissue culture, or parts of a plant, or selfing of a plant, or by producing seeds of a plant. In further embodiments, progeny may also encompass lettuce plants derived from crossing of at least one lettuce plant with another lettuce plant of the same or another variety or (breeding) line, or wild *Lactuca* plants, backcrossing, inserting of a locus into a plant or mutation. A progeny is, e.g., a first generation progeny, i.e. the progeny is directly derived from, obtained from, obtainable from or derivable from the parent plant by, e.g., traditional breeding methods (selfing and/or crossing) or regeneration or transformation. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above. Also double haploid plants are progeny.

A "plant line" or "breeding line" refers to a plant and its progeny being highly uniform in plant phenotype. As used herein, the term "inbred line" refers to a plant line which has been repeatedly selfed and is nearly homozygous for all alleles. Thus, an "inbred line" or "parent line" refers to a plant which has undergone several generations (e.g. at least 4, 5, 6, 7 or more) of inbreeding, resulting in a plant line with a high uniformity.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"Hybrid" refers to the seeds harvested from crossing one plant line or variety with another plant line or variety, and the plants or plant parts grown from said seeds.

"F1 hybrid" plant (or F1 hybrid seed) is the generation obtained from crossing two non-isogenic inbred parent lines. Thus, F1 hybrid seeds are seeds from which F1 hybrid plants grow.

An "interspecific hybrid" refers to a hybrid produced from crossing a plant of one species, e.g. *L. sativa*, with a plant of another species, e.g. *L. virosa*.

"Crossing" refers to the mating of two parent plants. Equally "Cross-pollination" refers to fertilization by the union of two gametes from different plants.

"Selfing" refers to the self-pollination of a plant, i.e. to the union of gametes from the same plant.

"Backcrossing" refers to a breeding method by which a trait, such as one or more Nr: 1 resistance-conferring QTLs, can be transferred from an inferior genetic background (e.g. a wild lettuce; also referred to as "donor") into a superior genetic background (also referred to as "recurrent parent"), e.g. cultivated lettuce. An offspring of a cross (e.g. an F1 plant obtained by crossing a wild, Nr: 1-resistant lettuce with a cultivated, Nr:1-susceptible lettuce; or an F2 plant or F3 plant, etc., obtained from selfing the F1) is "backcrossed" to the parent with the superior genetic background, e.g. to the cultivated, Nr:1-susceptible, parent After repeated backcrossing, the trait of the inferior genetic background will have been incorporated into the superior genetic background. The terms "gene converted" or "conversion plant" or "single/double/triple locus conversion" in this context refer to plants which are developed by backcrossing wherein essentially all of the desired morphological and/or physiological characteristics of the recurrent parent are recovered in addition to the one or more QTLs (e.g. the Nr:1 resistance conferring QTL6.1, QTL7.1 and/or QTL7.2) transferred from the donor parent.

The term "traditional breeding techniques" encompasses herein crossing, backcrossing, selfing, selection, chromosome doubling, double haploid production, embryo rescue, the use of bridge species, protoplast fusion, marker assisted selection, mutation breeding etc. as known to the breeder (i.e. methods other than genetic modification/transformation/transgenic methods), by which, for example, one or more Nr:1-resistance conferring QTLs, referred herein to as QTL6.1, QTL7.1 and/or QTL7.2, can be obtained, identified, selected, and/or transferred.

"Regeneration" refers to the development of a plant from in vitro cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting off) leaf, pollen, embryo, cotyledon, hypocotyl, cells, protoplasts, meristematic cell, root, root tip, pistil, anther, flower, shoot tip, shoot, stem, fruit, and petiole. When a whole plant is regenerated by vegetative propagation, it is also referred to as a "vegetative propagation" or a "vegetatively propagated plant".

"Single (or double or triple) locus converted (conversion) plant" refers to plants which are developed by plant breeding techniques comprising or consisting of backcrossing, wherein essentially all of the desired morphological and/or physiological characteristics of a lettuce plant are recovered in addition to the characteristics of the single locus (or two or three loci) having been transferred into the plant via e.g. the backcrossing technique.

"Transgene" or "chimeric gene" refers to a genetic locus comprising a DNA sequence which has been introduced into the genome of a lettuce plant by transformation. A plant comprising a transgene stably integrated into its genome is referred to as "transgenic plant".

"Substantially equivalent" or "not significantly different" or "not statistically significantly different" refers to a characteristic that, when compared e.g. between two plant lines or varieties, is equivalent or almost identical. In other words, a characteristic being "substantially equivalent" between two plant lines or varieties means that the mean value for said characteristic differs less than 10% (e.g. 9, 8, 7, 6, 5, 4, 3, 2, 1% or less) and the statistical significance of this difference is not having a p≥0.05 using ANOVA.

"Average" refers herein to the arithmetic mean. The term "mean" refers to the arithmetic mean of several measurements. The skilled person understands that the phenotype of a plant line or variety depends to some extent on growing conditions and that, therefore, arithmetic means of at least 10, 15, 20, 30, 40, 50 or more plants are measured, preferably in randomized experimental designs with several replicates and suitable control plants grown under the same conditions in the same experiment.

"Statistically significant" or "statistically significantly" different or "significantly" different refers to a characteristic of a plant line or variety, such as Nr: 1 resistance, that, when compared to a suitable control (e.g. herein the genetic control line lacking the QTLs, or a Nr: 1 susceptible control variety, such as Mafalda) show a statistically significant difference in that characteristic (e.g. the p-value is less than 0.05, p<0.05, using ANOVA) from the (mean of the) control. So, e.g. a plant line or variety or genotype which has on average "statistically significantly fewer" aphids or "significantly fewer" aphids than the control, is a plant wherein the difference in average aphid number is statistically significant from the control plant.

"Lettuce aphid" refers to aphids of the species *Nasonovia ribisnigri*.

"Biotype Nr:0" refers to the lettuce aphid biotype against which the Nr gene from IVT280 provides resistance, i.e. lettuce aphids of this biotype are unable to feed and reproduce on varieties comprising the Nr gene, such as Mafalda (Nunhems), Barcelona (Nunhems), or others.

"Biotype Nr:1" refers to the lettuce aphid biotype against which the Nr gene from IVT280 does not provide resistance. Thus, lettuce aphids of this biotype can feed and reproduce on varieties and lines comprising the Nr gene, such as Mafalda (Nunhems), Barcelona (Nunhems), or others.

When referring to resistance tests carried out under controlled environmental conditions (e.g. in climate cells), preferably clonal colonies of single, selected aphids of biotype Nr:0 or Nr:1 are referred to. These are also referred to as aphid "isolates" herein.

A wild or cultivated lettuce plant line, variety or accessions is said to be a "Nr:0 resistant plant", or a "plant resistant against biotype Nr:0", or a plant having "Nr:0 resistance", or an "Nr:0 resistance phenotype", if reproduction (average number of aphids per plant, counted periodically, e.g. after about 7, 14, 21, 28, 35 and/or more days, after infestation with aphids of biotype Nr:0) of biotype Nr:0 is statistically significantly reduced compared to control plants lacking lettuce aphid resistance genes, such as susceptible varieties Salinas (synonym Saladin; originally developed by breeder Ryder E.J., USDA, ARS, California, USA), or others. A significant reduction in reproduction of biotype Nr:0 can be determined using e.g. a greenhouse test or caged field test, as known in the art, e.g. as described in McCreight and Liu, 2012, HortScience 47(2), in Materials and Methods, or others. The greenhouse test or caged field test may be a free-choice (aphids are able to feed and reproduce on several plant lines or varieties) and/or a non-choice test (aphids are only able to feed and reproduce on one plant line or variety). Alternatively, open field tests may be carried out, whereby the natural infestation of susceptible controls, such as variety Salinas (synonym Saladin), is monitored and when infestation on the control is numerous, aphids are counted on test plants and controls. The term encompasses both "partial Nr:0 resistance" (as in PI491093 described in McCreight and Liu, 2012) and "complete Nr:0 resistance" (as in IVT280, see idem McCreight and Liu 2012). On completely Nr:0 resistant plants virtually no aphids of biotype Nr:0 feed and reproduce at the weekly time points measured post-inoculation or post-infestation.

A wild or cultivated lettuce plant line, variety or accessions is said to be a "Nr:1 resistant plant", or a "plant resistant against biotype Nr:1", or a plant having "Nr:1 resistance", or an "Nr:1 resistance phenotype", or a "plant having significantly reduced susceptibility", or "significantly enhanced resistance", if the average number of aphids of biotype Nr:1 per plant, counted at one or more time-points after infestation with aphids of biotype Nr:1 (e.g. 2, 3, 4, 5, 6, 7, 8, 9, 10, 11, 12, 13, 14 or more weeks after transplant of seedlings into the field; and/or after plants have reached the 3-4 true leaf stage and thereafter, i.e. when plants have reached 30%, 40%, 50%, 60%, 70%, 80%, 90% or 100% of the final adult size) is statistically significantly reduced compared to control plants lacking lettuce aphid resistance genes (such as variety Salinas (synonym Saladin)) and/or compared to control plants having the Nr resistance gene, such as variety Mafalda (Nunhems) and/or the genetic control lacking the introgression fragment(s) but otherwise being genetically identical or genetically very similar to the plant comprising the introgression fragment(s). In one aspect, a significant reduction refers to the average number of aphids on the Nr:1 resistant plant being at most 50%, 49%, 48%, 47%, 45%, preferably at most 40%, preferably at most 30%, 20% or 10%, more preferably at most 5%, 3%, 2%/0, or 1% of the average number of aphids found on a Nr:1 susceptible variety, such as variety Mafalda (or other Nr:1 susceptible varieties comprising the Nr gene), or on the genetic control, when grown under the same conditions. In one embodiment, plants are free or virtually free (less than an average of 10, 9, 8, 7, 6, 5, 4, 3 aphids per plant line or variety) of Nr:1 aphids. Nr:1 resistance can be determined in Nr:1 resistance assays as defined and as described in the Examples.

A "Nr: 1-resistance assay" may be either a non-choice test (aphids are only able to feed and reproduce on one plant line or variety) and/or a (free-) choice test, as e.g. described in the Examples. The choice or non-choice tests may be in controlled environments, such as climate cells, or in the field (open field for choice or caged field for non-choice tests). Choice-tests for resistance refers to tests where the aphids can choose among different plant genotypes for feeding and reproduction. Generally, choice-tests are used to identify antixenosis (non-preference) resistance, i.e. resistance caused by factors that make a plant genotype less attractive. Non-choice tests for resistance refers to tests where the aphids cannot choose among different plant genotypes for feeding and reproduction, but are only allowed to feed and reproduce on one genotype. This allows antibiosis to be detected. On Nr: 1 susceptible control plants, such as Mafalda, the aphid is able to reproduce to more than about 50, 100, 150, 200, 250, 300 or more aphids. Resistance effective under non-choice conditions affects the insects themselves, e.g. they die, produce fewer offspring or grow more slowly.

A genetic element, a locus, an introgression fragment or a gene or allele conferring a trait (such as one or more QTLs conferring resistance against *N. ribisnigri* biotype Nr: 1) is said to be "obtainable from" or can be "obtained from" or "derivable from" or can be "derived from" or "as present in" or "as found in" a plant or seed if it can be transferred from the plant or seed in which it is present into another plant or seed in which it is not present (such as a line or variety) using traditional breeding techniques without resulting in a phenotypic change of the recipient plant apart from the addition of the trait (Nr:1 resistance) conferred by the genetic element, locus, introgression fragment, gene or allele. The terms are used interchangeably and the genetic element, locus, introgression fragment, gene or allele can thus be transferred into any other genetic background lacking the trait. Not only seeds deposited and comprising the genetic element, locus, introgression fragment, gene or allele can be used, but also progeny/descendants from such seeds which have been selected to retain the genetic element, locus, introgression fragment, gene or allele, can be used and are encompassed herein, such as commercial varieties developed from the deposited seeds or from descendants thereof. Whether a plant (or genomic DNA, cell or tissue of a plant) comprises the same genetic element, locus, introgression fragment, gene or allele as obtainable from the deposited seeds can be determined by the skilled person using one or more techniques known in the art, such as phenotypic assays, whole genome sequencing, molecular marker analysis (e.g. using one or more or all of the marker disclosed herein), trait mapping, chromosome painting, allelism tests and the like, or combinations of techniques.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "gene" means a (genomic) DNA sequence comprising a region (transcribed region), which is transcribed into a messenger RNA molecule (mRNA) in a cell, and an operably linked regulatory region (e.g. a promoter). Different alleles of a gene are thus different alternative forms of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein.

"Allelism test" refers to a genetic test whereby it can be tested whether two phenotypes, e.g. two Nr:1 resistances, seen in two plant lines or varieties are determined by the same gene or by different genes. For example, the plants to be tested are crossed with each other, the F1 is selfed and the segregation of the phenotypes amongst the F2 progeny is determined. The ratio of segregation indicates if the genes are allelic.

The term "locus" (loci plural) means a specific place or places or a site on a chromosome where for example a gene or genetic marker is found. The Nr: 1 resistance locus (or Nr1 resistance-conferring locus/loci) is/are, thus, the location in the genome of wild lettuce, especially *Lactuca virosa* accession, such as (but not limited to) NCIMB 42086, where the Nr: 1-resistance conferring QTL(s) is/are found on chromosome 6 (QTL6.1) and/or on chromosome 7 (QTL7.1 and/or QTL7.2). In cultivated lettuce according to the invention one or more QTLs conferring Nr: 1 resistance are introgressed from wild lettuce accessions which comprise one or more of the QTLs, such as the wild *L. virosa* accession deposited under accession numbers NCIMB 42086.

A "quantitative trait locus", or "QTL" is a chromosomal locus that encodes for one or more alleles that affect the expressivity of a continuously distributed (quantitative) phenotype. The resistance conferring quantitative trait loci are named herein QTL6.1, QTL7.1 and QTL7.2.

"Lettuce genome" and "physical position on the lettuce genome" and "chromosome 6" and/or on "chromosome 7" refers to the physical genome of cultivated lettuce, world wide web at lgr.genomecenter.ucdavis.edu (Lettuce version 3.2 Database, comprising chromosome 6, designated Lsat_1_v4_lg6, and chromosome 7, designated Lsat_1_v4_lg7), and the physical chromosomes and the physical position on the chromosomes. So, for example SNP_01 is located at the nucleotide (or 'base') positioned physically at nucleotide 60,688,939 of chromosome 6, which has a physical size from 0 to 244.7 Mb. Likewise, SNP_08 is located at the nucleotide (or 'base') positioned at 72,772,104 of chromosome 7, which chromosome has a physical size from 0 to 242.9 Mb.

"Physical distance" between loci (e.g. between molecular markers and/or between phenotypic markers) on the same chromosome is the actually physical distance expressed in bases or base pairs (bp), kilo bases or kilo base pairs (kb) or megabases or mega base pairs (Mb).

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of 1%. If no recombinants can be found, the RF is zero and the loci are either extremely close together physically or they are identical. The further apart two loci are, the higher the RF.

"Introgression fragment" or "introgression segment" or "introgression region" refers to a chromosome fragment (or chromosome part or region) which has been introduced into another plant of the same or related species by crossing or traditional breeding techniques, such as backcrossing, i.e. the introgressed fragment is the result of traditional breeding methods referred to by the verb "to introgress" (such as backcrossing). In lettuce, wild lettuce accessions may be used to introgress fragments of the wild genome (e.g. *L. virosa*) into the genome of cultivated lettuce, *L. sativa*. Such a cultivated lettuce plant thus has a "genome of cultivated *L. sativa*", but comprises in the genome a fragment (or two or three fragments) of a wild lettuce, e.g. an introgression fragment (or two or three) of a related wild *Lactuca* genome, such as *L. virosa*. It is understood that the term "introgression fragment" never includes a whole chromosome, but only a part of a chromosome. The introgression fragment can be large, e.g. even half of a chromosome, but is preferably smaller, such as about 80 Mb, 74 Mb, 73 Mb, 70 Mb, 50 Mb, 30 Mb, 20 Mb, 15 Mb or less, such as about 10 Mb or less, about 9 Mb or less, about 8 Mb or less, about 7 Mb or less, about 6 Mb or less, about 5 Mb or less, about 4 Mb or less, about 3 Mb or less, about 2 Mb or less, about 1 Mb (equals 1,000,000 base pairs) or less, or about 0.5 Mb (equals 500,000 base pairs) or less, such as about 200,000 bp (equals 200 kilo base pairs) or less, about 100,000 bp (100 kb) or less, about 50,000 bp (50 kb) or less, about 25,000 bp (25 kb) or less.

"Uniformity" or "uniform" relates to the genetic and phenotypic characteristics of a plant line or variety. Inbred lines are genetically highly uniform as they are produced by several generations of inbreeding.

The term "Nr:1-allele" or "Nr:1 resistance allele", refers to an allele found at the locus QTL6.1 or QTL7.1 or QTL7.2 which in one aspect of the invention is introgressed into cultivated lettuce (onto cultivated *L. sativa* chromosome 6 and/or 7) from a wild lettuce, especially from a *L. virosa* accession. The term "Nr:1-allele", thus, also encompasses Nr:1-alleles obtainable from different wild lettuce accessions. When one or two Nr:1-alleles are present at a specific locus in the genome (i.e. in heterozygous or homozygous form, respectively), the plant line or variety has significantly enhanced Nr:1 resistance compared to the genetic control lacking the QTL. In cultivated lettuce plant lacking the introgression fragment, the *L. sativa* allele found at the same locus on chromosome 6 and/or 7 is herein referred to as "wild type" allele (wt). Thus, a cultivated lettuce susceptible to Nr:1 and lacking the QTLs on chromosome 6 and 7 is designated wt/wt, whereas QTL6.1/wt and/or QTL7.1/wt and/or QTL7.2/wt plants, and QTL6.1/QTL6.1 and/or QTL7.1/QTL7.1 and/or QTL7.2/QTL7.2 plants, are cultivated lettuce plants which possess the QTLs in heterozygous or homozygous form, respectively. The genotype of the SNP markers provided herein is also indicative of the wild type genotype or of the introgression fragment comprising the QTLs being in homozygous or heterozygous form. E.g. the genotype of SNP_01 indicative of QTL6.1 is 'AT' (indicative of QTL6.1/wt) or 'AA' (indicative of QTL6.1/QTL6.1) while the genotype indicative of the wild type is 'T' (wt/wt). See elsewhere herein for all other SNPs. Thus, when reference is made to a SNP marker herein or a SNP genotype, the genotype of the marker indicative of the introgression fragment comprising the QTL conferring Nr:1 resistance is referred to (in homozygous or heterozygous form).

"Variant" or "orthologous" sequences or "variant QTL6.1, QTL7.1 or QTL7.2" refers to QTLs (QTL6.1, QTL7.1 or QTL7.2), or introgression fragment(s) comprising these, which are derived from different wild lettuce plants (especially different L. virosa plants or accessions) than the QTL6.1, QTL7.1 and QTL7.2 (and genomic region comprising these) present in NCIMB42086, but which variants comprise one or more or all of the SNPs linked to QTL6.1, QTL7.1 and/or QTL7.2 and wherein the variant genomic sequence comprises substantial sequence identity to the SEQ ID NO: comprising the SNP (any one of SEQ ID NO: 1-22, SNP1.23, SNP2.24, SNP17.25, VSP1 to VSP4), i.e. at least 85%, 90%, 95%, 98%, 99% sequence identity or more. Thus, when reference herein is made to a certain SNP genotype in a specific genomic sequence (selected from SEQ ID NO: 1 to SEQ ID NO: 22, SNP1.23, SNP2.24, SNP17.25, VSP1 to VSP4), this encompasses also the SNP genotype in variants of the genomic sequence, i.e. the SNP genotype in a genomic sequence comprising at least 85%, 90%/0, 95%, 98%, 99% sequence identity or more to the sequence referred to (selected from SEQ ID NO: 1 to SEQ ID NO: 22, SNP1.23, SNP2.24, SNP17.25, VSP1 to VSP4). Thus any reference herein to any one of SEQ ID NO: 1 to 22, SNP1.23, SNP2.24, SNP17.25, VSP1 to VSP4, in one aspect also encompasses a variant of any one of SEQ ID NO: 1 to 22, SNP1.23, SNP2.24, SNP17.25, VSP1 to VSP4, said variant comprising at least 85%, 90%/0, 95%, 98%, 99% sequence identity or more to said sequence.

"Genetic control" is a lettuce line, variety or hybrid which has the same or very similar cultivated genome as the cultivated lettuce plant comprising the introgression on chromosome 6 (QTL6.1) and/or 7 (QTL7.1 and/or QTL7.2), except that it lacks said introgressions on chromosome 6 and 7, i.e. chromosomes 6 and 7 are "wild type" (wt/wt), i.e. cultivated lettuce genome.

The term "marker assay" refers to a molecular marker assay which can be used to test whether on cultivated L. sativa chromosome 6 and/or 7 an introgression from a wild lettuce is present which introgression fragment comprises the Nr:1 resistance conferring QTL (QTL6.1 and/or QTL7.1 and/or QTL7.2, or a variant of these) (or whether a wild lettuce comprises the QTL6.1 and/or QTL7.1 and/or QTL7.2 or variants of these in their genome), by determining the genotype of any one or more markers linked to the QTL6.1 (or a variant), e.g. the genotype of one or more SNP markers selected from SNP_01 to SNP_07, and/or any wild lettuce (especially L. virosa) genome-specific marker in-between SNP markers SNP_01 and SNP_07, and/or within 7 cM or within 5 cM of any one of these markers, and/or within 5 Mb, 3 Mb, 2 Mb, 1 Mb, 0.5 Mb, 0.1 Mb, 50 kb, 20 kb or less of any one of these markers; alternatively by determining the genotype of any one or more markers linked to the QTL6.1 (or a variant), e.g. the genotype of one or more SNP markers selected from SNP1.23, SNP_02, SNP2.24 and SNP_03 (optionally also VSP1 or VSP3), and/or any wild lettuce (especially L. virosa) genome-specific marker in-between SNP markers SNP1.23, SNP_02, SNP2.24 and SNP_03 (optionally also VSP1 or VSP3), and/or within 7 cM or within 5 cM of any one of these markers, and/or within 12 Mb, 10 Mb, 5 Mb, 3 Mb, 2 Mb, 1 Mb, 0.5 Mb, 0.1 Mb, 50 kb, 20 kb or less of any one of these markers; and/or the genotype of any one or more markers linked to the QTL7.1 (or a variant), e.g. the genotype of one or more SNP markers selected from SNP_15 to SNP_22, and/or any wild lettuce genome-specific marker in-between SNP markers SNP_15 and SNP_22, and/or within 7 cM or within 5 cM of any one of these markers, and/or within 5 Mb, 3 Mb, 2 Mb, 1 Mb, 0.5 Mb, 0.1 Mb, 50 kb, 20 kb or less of any one of these markers; alternatively by determining the genotype of any one or more markers linked to the QTL7.1 (or a variant), e.g. the genotype of one or more SNP markers selected from SNP_17, SNP_17.25, SNP_18 and SNP_19 (optionally also VSP2 or VSP4), and/or any wild lettuce (especially L. virosa) genome-specific marker in-between SNP markers SNP_17, SNP_17.25, SNP_18 and SNP_19 (optionally also VSP2 or VSP4), and/or within 7 cM or within 5 cM of any one of these markers, and/or within 12 Mb, 10 Mb, 5 Mb, 3 Mb, 2 Mb, 1 Mb, 0.5 Mb, 0.1 Mb, 50 kb, 20 kb or less of any one of these markers; and/or the genotype of any one or more markers linked to the QTL7.2 (or a variant), e.g. the genotype of one or more SNP markers selected from SNP_08 to SNP_14, and/or any wild lettuce genome-specific marker in-between SNP markers SNP_08 and SNP_14, and/or within 7 cM or within 5 cM of any one of these markers, and/or within 5 Mb, 3 Mb, 2 Mb, 1 Mb, 0.5 Mb, 0.1 Mb, 50 kb, 20 kb or less of any one of these markers A marker "in between" two markers is physically located in between the markers on the chromosome.

A "recombinant chromosome" refers to a chromosome having a new genetic makeup arising through crossing-over between homologous chromosomes, e.g. a "recombinant chromosome 6" or a "recombinant chromosome 7", i.e. a chromosome 6 or 7 which is not present in either of the parent plants and arose through a rare crossing-over event between homologous chromosomes of a chromosome 6 or 7 pair, respectively. Herein, for example, recombinant lettuce chromosomes 6 and 7 are provided, each comprising a Nr:1 resistance QTL.

"Marker assisted selection" or "MAS" is a process of using the presence of molecular markers, which are genetically linked to a particular locus or to a particular chromosome region (e.g. introgression fragment), to select plants for the presence of the specific locus or region (introgression fragment). For example, a molecular marker genetically linked to a Nr:1 QTL, can be used to detect and/or select lettuce plants comprising the Nr: 1 QTL on chromosome 6 and/or 7. The closer the genetic linkage of the molecular marker to the locus (e.g. about 7 cM, 6 cM, 5 cM, 4 cM, 3 cM, 2 cM, 1 cM, 0.5 cM or less), the less likely it is that the marker is dissociated from the locus through meiotic recombination. Likewise, the closer two markers are linked to each other (e.g. within 7 cM or 5 cM, 4 cM, 3 cM, 2 cM, 1 cM or less) the less likely it is that the two markers will be separated from one another (and the more likely they will co-segregate as a unit).

A marker "within 7 cM or within 5 cM" of another marker refers to a marker which genetically maps to within the 7 cM or 5 cM region flanking the marker (i.e. either side of the marker). Similarly, a marker within 10 Mb, 5 Mb, 3 Mb, 2.5 Mb, 2 Mb, 1 Mb, 0.5 Mb, 0.4 Mb, 0.3 Mb, 0.2 Mb, 0.1 Mb, 50 kb, 20 kb, 10 kb, 5 kb or less of another marker refers to a marker which is physically located within the 5 Mb, 3 Mb, 2.5 Mb, 2 Mb, 1 Mb, 0.5 Mb, 0.4 Mb, 0.3 Mb, 0.2 Mb, 0.1

Mb, 50 kb, 20 kb, 10 kb, 5 kb or less, of the genomic DNA region flanking the marker (i.e. either side of the marker).

"LOD-score" (logarithm (base 10) of odds) refers to a statistical test often used for linkage analysis in animal and plant populations. The LOD score compares the likelihood of obtaining the test data if the two loci (molecular markers loci and/or a phenotypic trait locus) are indeed linked, to the likelihood of observing the same data purely by chance. Positive LOD scores favor the presence of linkage and a LOD score greater than 3.0 is considered evidence for linkage. A LOD score of +3 indicates 1000 to 1 odds that the linkage being observed did not occur by chance.

An "isolated nucleic acid sequence" or "isolated DNA" refers to a nucleic acid sequence which is no longer in the natural environment from which it was isolated, e.g. the nucleic acid sequence in a bacterial host cell or in the plant nuclear or plastid genome.

A "host cell" or a "recombinant host cell" or "transformed cell" are terms referring to a new individual cell (or organism) arising as a result of at least one nucleic acid molecule, having been introduced into said cell. The host cell is preferably a plant cell or a bacterial cell. The host cell may contain the nucleic acid as an extra-chromosomally (episomal) replicating molecule, or comprises the nucleic acid integrated in the nuclear or plastid genome of the host cell, or as introduced chromosome, e.g. minichromosome.

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimises the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS as available on the world wide web under ebi.ac.uk/Tools/psalemboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 85%, 90%, 95%, 98%, 99% or more (e.g. at least 99.1, 99.2 99.3 99.4, 99.5, 99.6, 99.7, 99.8, 99.9 or more (as determined by Emboss "needle" using default parameters, i.e. gap creation penalty=10, gap extension penalty=0.5, using scoring matrix DNAFULL for nucleic acids an Blosum62 for proteins).

When reference is made to a nucleic acid sequence (e.g. DNA or genomic DNA) having "substantial sequence identity to" a reference sequence or having a sequence identity of at least 80%, e.g. at least 85%, 90%/0, 95%, 98%, 99%, 99.2%, 99.5%, 99.9% nucleic acid sequence identity to a reference sequence, in one embodiment said nucleotide sequence is considered substantially identical to the given nucleotide sequence and can be identified using stringent hybridisation conditions. In another embodiment, the nucleic acid sequence comprises one or more mutations compared to the given nucleotide sequence but still can be identified using stringent hybridisation conditions.

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

FIGURES

FIG. 1: A. Graph showing the average number of aphids (German isolate of Nr: 1) on susceptible control variety Mafalda and on NCIMB 42086 in a non-choice test, at 7, 14, 21, 28 and 35 days post inoculation. B. shows the same graph as A., but on a more detailed scale.

FIG. 2: A. Graph showing the average number of aphids on NCIMB 42086 in a free-choice test, at 7, 14, 21, 28 and 35 days post inoculation. A. relates to a German Nr:1 isolate from the Pfalz region, while B. relates to a French Nr: 1 isolate from the Perpignan area.

Figure 3A:
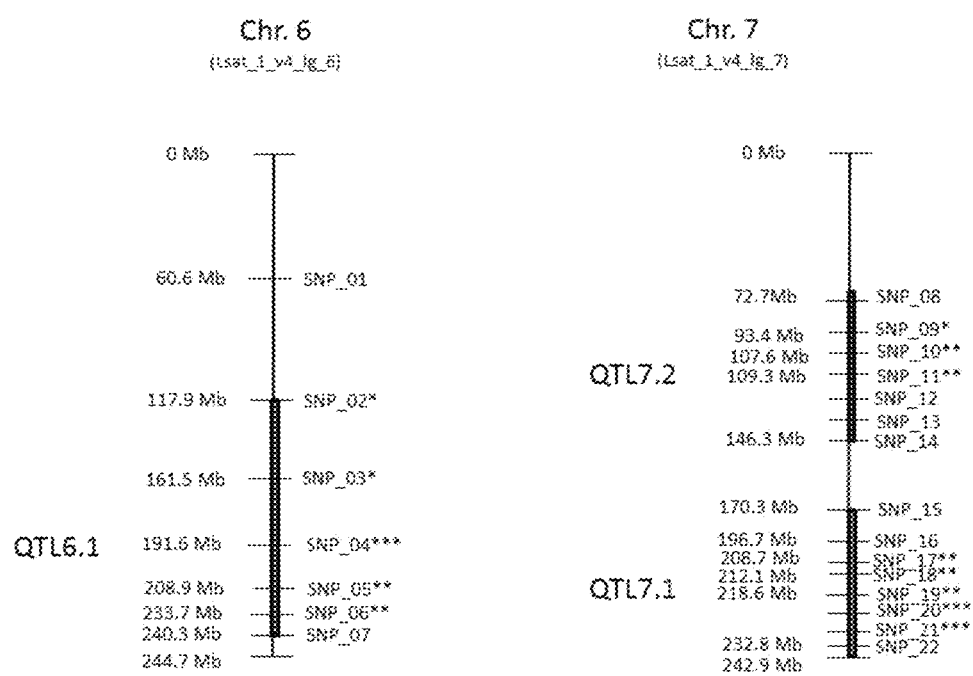
Figure 3B:
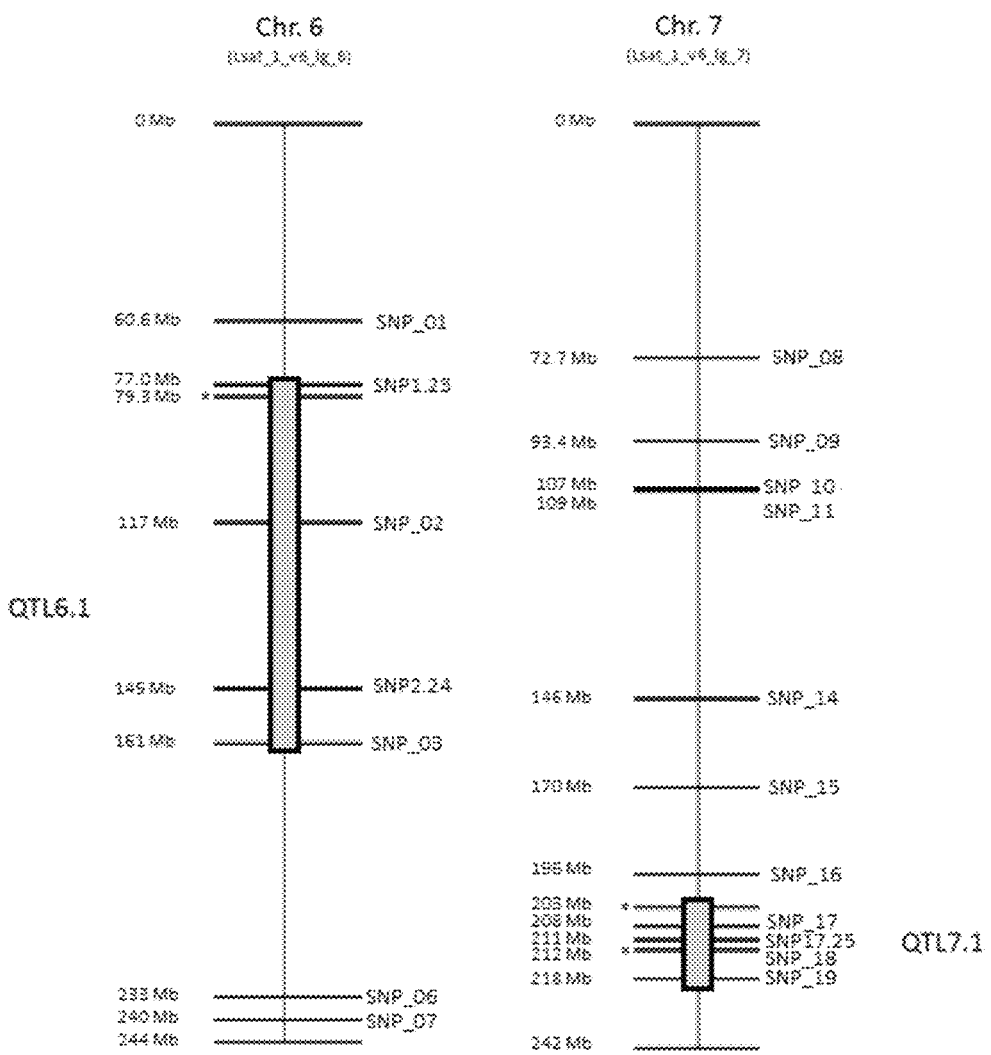

FIG. 3A: Schematic graph (not to scale) of chromosome 6 and 7 of *L. sativa* comprising an introgression fragment (exemplified by the fat bar, which may be longer or shorter than drawn herein) from *L. virosa* accession NCIMB42086 on chromosome 6 (comprising QTL6.1) and two introgression fragments from *L. virosa* accession NCIMB42086 on chromosome 7 (comprising QTL7.1 and QTL7.2), as well as the SNP markers indicative of the introgression fragments and their physical position on the lettuce genome. The number of stars (*) indicates the LOD-score being significant (one star) or highly significant (two or three stars).

FIG. 3B: Schematic graph (not to scale) of chromosome 6 and 7 of *L. sativa* comprising an introgression fragment (gray bar) from a wild *L. virosa* (e.g. from accession NCIMB42086) on chromosome 6 (comprising QTL6.1 or a variant thereof) and on chromosome 7 (comprising QTL7.1 or a variant thereof). The * indicates SNP markers which are specific for two wild *L. virosa* accessions, SNP markers VSP1 and VSP3 on chromosome 6 and VSP2 and VSP4 on chromosome 7 (whereby VSP1 and VSP2 are specific for one of the accessions and VSP3 and VSP4 are specific for the other accession.

Figure 4:
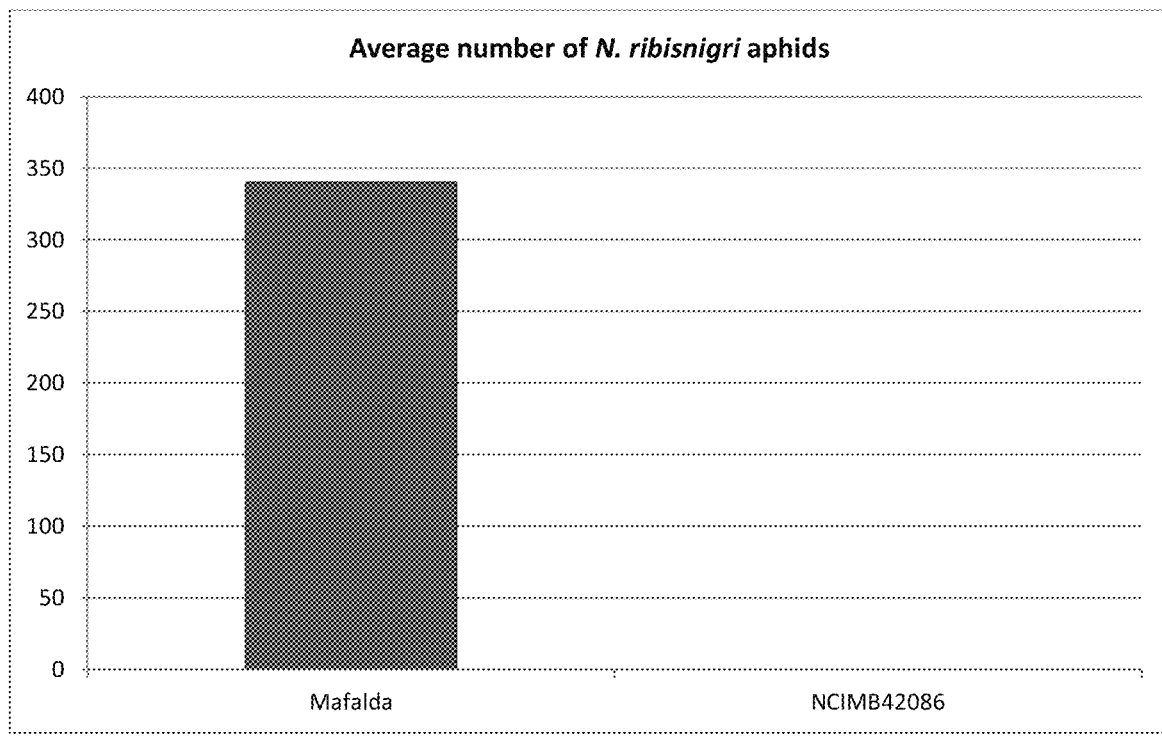

FIG. 4: Results of the non-choice field assay carried out in Murcia, Spain, showing zero aphids on NCIMB42086 compared to >300 aphids on the Nr:0 resistant variety Mafalda.

DETAILED DESCRIPTION

The present invention relates to a cultivated lettuce plant, *Lactuca sativa*, comprising one or two or three QTLs introgressed from wild lettuce, wherein said QTLs confer resistance against *N. ribisnigri* biotype 1 (Nr:1). In particular, the Nr:1 resistance is conferred by an introgression fragment on cultivated lettuce chromosome 6 (comprising QTL6.1) and/or 7 (comprising QTL 7.1 and/or QTL7.2), wherein said introgression fragment is from a wild lettuce plant, in particular a plant of the species *Lactuca virosa*.

Thus, in one aspect a *Lactuca sativa* plant is provided comprising an introgression fragment from a wild lettuce plant on chromosome 6 and/or on chromosome 7, wherein said introgression fragment on chromosome 6 comprises a Quantitative Trait Locus (QTL) referred to as QTL6.1 and wherein said introgression fragment on chromosome 7 comprises a Quantitative Trait Locus referred to as QTL7.1 and/or QTL7.2, and wherein said introgression fragment on chromosome 6 and/or 7 confers resistance against *Nasonovia ribisnigri* biotype 1 (Nr: 1). Each one of the introgression fragments may be in homozygous or heterozygous form. In one aspect, the introgression fragment(s) is/are in homozygous form. In one aspect, where the plant comprises more than one introgression fragment, i.e. two or three fragments, these originate from the same wild lettuce accession. In one embodiment of the invention this wild lettuce accession is a *L. virosa* accession (such as NCIMB 42086 or progeny thereof). In one aspect the wild accession is a *L. virosa* accession selected from an accession comprising *L. virosa* accession specific markers VSP1 and VSP2; or an accession comprising *L. virosa* accession specific markers VSP3 and VSP4.

When reference is made herein to an introgression fragment on chromosome 6 and/or 7 having Nr:1 resistance conferring QTL this encompasses various sizes of introgression fragments, e.g. the fragment comprising all SNP markers (SNP_01 to SNP_07, or in the alternative SNP1.23, SNP_02, SNP2.24 and SNP_03, or any marker in between these, for the fragment on chromosome 6 (comprising QTL6.1); SNP_08 to SNP_14, or any marker in between these, for the fragment on chromosome 7 (comprising QTL7.2); SNP_15 to SNP_22, or in the alternative SNP_17, SNP17.25, SNP_18 and SNP_19, or any marker in between these, for the fragment on chromosome 7, comprising QTL7.1), but also smaller introgression fragments (comprising e.g. 1, 2, 3 or 4 of the SNP markers), where however the fragment remains large enough to confer Nr:1 resistance when the introgression fragment(s) is/are in heterozygous or homozygous form in the cultivated lettuce genome.

When referring to the SNP markers herein, which are indicative of the presence of the introgression fragment (and the Nr:1 QTL present on the introgression fragment), it is understood that the SNP genotype which is indicative of the introgression fragment is referred to, i.e. the SNP genotype as provided in Table 1, 2 and 3, or in Table 4, 5, 6 and 7, and herein below. It is noted that the SNP marker genotype can distinguish between the introgression fragment being in homozygous or heterozygous form, as shown in these Tables. In homozygous form the nucleotide is identical, while in heterozygous form the nucleotide is not identical. The SNP genotype of the 'wild type' chromosome lacking the introgression fragment is the other genotype, also listed in Tables 1-3 and Tables 4-7 (under genotype of *L. sativa* parent). So, e.g. the genotype of SNP_01 indicative of the introgression fragment comprising QTL6.1 is 'AT' (QTL6.1/wt, i.e. heterozygous for the resistance conferring QTL) or 'AA' (QTL6.1/QTL6.1, i.e. homozygous for the resistance conferring QTL) while the SNP genotype indicative of the wild type/genetic control (lacking the introgression fragment) is 'TT' (wt/wt). Thus, when referring to a plant or plant part (e.g. cell) comprising the introgression fragment in homozygous or heterozygous form, it is understood that the SNP markers linked to the introgression fragment have the corresponding SNP genotype. For example, a plant according to the invention which is homozygous for the introgression fragment comprising QTL6.1 comprises the SNP markers in homozygous form.

So in one aspect, a cultivated *L. sativa* plant is provided comprising an introgression fragment on chromosome 6 and/or on chromosome 7 in homozygous or heterozygous form, wherein said introgression fragment confers resistance against biotype Nr: 1. In a preferred aspect, one, two or all three of the introgression fragments are in homozygous form (and the SNP marker(s) indicative of the QTL are homozygous for the mentioned nucleotide).

The resistance against Nr:1 is phenotypically expressed as a (statistically) significantly lower average number of aphids of biotype Nr:1 on the plants of the cultivated lettuce plant line or variety comprising the introgression fragment(s) on chromosome 6 (comprising QTL6.1) and/or 7 (comprising QTL7.1 and/or 7.2) in homozygous or heterozygous form compared to the control line or variety lacking the introgression fragment on chromosome 6 and 7 when grown under the same environment. The control line or variety is a cultivated lettuce line or variety which is susceptible against Nr: 1. In one aspect is it selected from a variety which is susceptible against Nr:0 and Nr:1 (i.e. lacking *N. ribisnigri* resistance). In another preferred aspect it is a line or variety comprising Nr:0 resistance conferred by the dominant Nr gene, such as variety Mafalda (or others, such as Susana, Sylvesta, Veronique, and many others, see the world wide web at nunhems.nl, where varieties with Nr:0 resistance are indicated as 'HR'). In yet another aspect it is the genetic control line or variety.

Thus, different cultivated lettuce plants are provided herein, which either comprise an introgression fragment on chromosome 6 (comprising QTL6.1 or a variant thereof) in homozygous or heterozygous form; or which comprise an introgression fragment on chromosome 7 (comprising QTL7.1 or a variant thereof) in homozygous or heterozygous form; or which comprise an introgression fragment on chromosome 7 (comprising QTL7.2 or a variant thereof) in homozygous or heterozygous form; or which comprise two introgression fragments (QTL6.1 and QTL7.1 or variants of either of these; or QTL6.1 and QTL7.2 or variants of either of these; or QTL7.1 and QTL7.2 or variants of either of these; wherein the two QTLs can independently from each other be in homozygous or heterozygous form) or all three introgression fragments (QTL6.1, QTL7.1 and QTL7.2 or variants of any of these), any one of these three QTLs independently being in homozygous or in heterozygous form.

The plants of the invention therefore comprise a genome of cultivated lettuce, with one or two recombinant chromosomes 6 and/or with one or two recombinant chromosomes 7. The recombinant chromosomes comprise a fragment of a wild lettuce (especially of *L. virosa*; in one aspect of *L. virosa* accession NCIMB42086 or progeny thereof, or from another *L. virosa*, such as an accession comprising VSP1 and VSP2 or comprising VSP3 and VSP4), which is easily distinguishable from the cultivated lettuce genome by molecular marker analysis (using e.g. the markers provided herein), whole genome sequencing, chromosome painting and similar techniques.

In one aspect the presence of the introgression fragment(s) on chromosomes 6 and/or 7 in the genome of the plant or plant cell or plant tissue (or in the DNA extracted therefrom) is detectable by a molecular marker assay which detects one or more molecular markers of the introgression fragment(s). However, as mentioned, other techniques may be used, e.g. the SNP genotype of the markers may also be determined by sequencing or by using alternative markers located in-between the SNP markers provided herein or within 7 cM, or within 5 cM, of a marker provided herein; or within 10 Mb, 5 Mb, 3 Mb, 2.5 Mb, 2 Mb, 1 Mb, 0.5 Mb, 0.4 Mb, 0.3 Mb, 0.2 Mb, 0.1 Mb, 50 kb, 20 kb, 10 kb, 5 kb or less of a marker provided herein.

Lettuce Plants Comprising an Introgression Fragment on Chromosome 6 (Comprising QTL 6.1 or a Variant Thereof)

Based on the first QTL mapping results, the following cultivated lettuce plants are encompassed herein.

In one aspect the introgression fragment on chromosome 6 is detectable by a molecular marker assay which detects at least 1, preferably at least 2 or 3, or at least 4, 5, 6, or 7 of the markers selected from the group consisting of:
  a) the AA or AT genotype for the Single Nucleotide Polymorphism marker SNP_01 in SEQ ID NO: 1 (or in a sequence comprising substantial sequence identity to SEQ ID NO:1);
  b) the CC or CT genotype for the Single Nucleotide Polymorphism marker SNP_02 in SEQ ID NO: 2 (or in a sequence comprising substantial sequence identity to SEQ ID NO:2);
  c) the AA or AC genotype for the Single Nucleotide Polymorphism marker SNP_03 in SEQ ID NO: 3 (or in a sequence comprising substantial sequence identity to SEQ ID NO:3);
  d) the GG or GA genotype for the Single Nucleotide Polymorphism marker SNP_04 in SEQ ID NO: 4 (or in a sequence comprising substantial sequence identity to SEQ ID NO:4);
  e) the TT or TC genotype for the Single Nucleotide Polymorphism marker SNP_05 in SEQ ID NO: 5 (or in a sequence comprising substantial sequence identity to SEQ ID NO:5);
  f) the CC or CA genotype for the Single Nucleotide Polymorphism marker SNP_06 in SEQ ID NO: 6 (or in a sequence comprising substantial sequence identity to SEQ ID NO:6);
  g) the GG or GT genotype for the Single Nucleotide Polymorphism marker SNP_07 in SEQ ID NO: 7 (or in a sequence comprising substantial sequence identity to SEQ ID NO:7);
  h) any wild lettuce genome specific marker, especially *L. virosa*-genome specific marker, located physically in-between SNP_01 and SNP_07 (e.g. in-between SNP_01 and SNP_06, SNP_01 and SNP_05, SNP_01 and SNP_04, SNP_01 and SNP_03, SNP_01 and SNP_02); or in between SNP_02 and SNP_07 (e.g. in-between SNP_02 and SNP_06, SNP_02 and SNP_05, SNP_02 and SNP_04, SNP_02 and SNP_03); or in between SNP_03 and SNP_07 (e.g. in-between SNP_03 and SNP_06, SNP_03 and SNP_05, SNP_03 and SNP_04); or in between SNP_04 and SNP_7 (e.g. in-between SNP_04 and SNP_06, SNP_04 and SNP_05); or in between SNP_05 and SNP_07 (e.g. in-between SNP_05 and SNP_06); or in between SNP_06 and SNP_07.

As mentioned, the skilled person can also develop other molecular markers, e.g. a wild *L. virosa* genome specific marker in-between marker SNP_01 and SNP_07 and/or within 7 cM or within 5 cM of any one of SNP_01 to SNP_07, and/or within 5 Mb, 3 Mb, 2.5 Mb, 2 Mb, 1 Mb, 0.5 Mb, 0.4 Mb, 0.3 Mb, 0.2 Mb, 0.1 Mb, 50 kb, 20 kb, 10 kb, 5 kb or less of any one of SNP_01 to SNP_07. Such markers may also be a stretch of nucleotide, CAPS markers, INDELs, etc. The skilled person can, for example, sequence the introgression fragment or the QTL region and use the sequence information to develop new markers and marker assays.

In another aspect the introgression fragment on chromosome 6 (comprising QTL6.1 or a variant) is detectable by a molecular marker assay which detects at least 1, preferably at least 2 or 3, or at least 4, 5, 6, or all 7 of the markers selected from the group consisting of:
  a) the AA or AT genotype for the Single Nucleotide Polymorphism marker SNP_01 in SEQ ID NO: 1 (or in a sequence comprising substantial sequence identity to SEQ ID NO:1);
  b) the CC or CT genotype for the Single Nucleotide Polymorphism marker SNP_02 in SEQ ID NO: 2 (or in a sequence comprising substantial sequence identity to SEQ ID NO:2);
  c) the AA or AC genotype for the Single Nucleotide Polymorphism marker SNP_03 in SEQ ID NO: 3 (or in a sequence comprising substantial sequence identity to SEQ ID NO:3);
  d) the GG or GA genotype for the Single Nucleotide Polymorphism marker SNP_04 in SEQ ID NO: 4 (or in a sequence comprising substantial sequence identity to SEQ ID NO:4);
  e) the TT or TC genotype for the Single Nucleotide Polymorphism marker SNP_05 in SEQ ID NO: 5 (or in a sequence comprising substantial sequence identity to SEQ ID NO:5);
  f) the CC or CA genotype for the Single Nucleotide Polymorphism marker SNP_06 in SEQ ID NO: 6 (or in a sequence comprising substantial sequence identity to SEQ ID NO:6);
  g) the GG or GT genotype for the Single Nucleotide Polymorphism marker SNP_07 in SEQ ID NO: 7 (or in a sequence comprising substantial sequence identity to SEQ ID NO:7).

In another aspect a cultivated *L. saliva* plant is provided comprising an introgression fragment on chromosome 6 in homozygous or heterozygous form, wherein said introgression fragment confers Nr: 1 resistance and wherein said introgression fragment is detectable by a molecular marker assay which detects at least 2, 3 or 4 (or at least 5, 6 or all 7) consecutive markers selected from the group consisting of:
  a) the AA or AT genotype for the Single Nucleotide Polymorphism marker SNP_01 in SEQ ID NO: 1 (or in a sequence comprising substantial sequence identity to SEQ ID NO:1);
  b) the CC or CT genotype for the Single Nucleotide Polymorphism marker SNP_02 in SEQ ID NO: 2 (or in a sequence comprising substantial sequence identity to SEQ ID NO:2);
  c) the AA or AC genotype for the Single Nucleotide Polymorphism marker SNP_03 in SEQ ID NO: 3 (or in a sequence comprising substantial sequence identity to SEQ ID NO:3);

d) the GG or GA genotype for the Single Nucleotide Polymorphism marker SNP_04 in SEQ ID NO: 4 (or in a sequence comprising substantial sequence identity to SEQ ID NO:4);
e) the TT or TC genotype for the Single Nucleotide Polymorphism marker SNP_05 in SEQ ID NO: 5 (or in a sequence comprising substantial sequence identity to SEQ ID NO:5);
f) the CC or CA genotype for the Single Nucleotide Polymorphism marker SNP_06 in SEQ ID NO: 6 (or in a sequence comprising substantial sequence identity to SEQ ID NO:6);
g) the GG or GT genotype for the Single Nucleotide Polymorphism marker SNP_07 in SEQ ID NO: 7 (or in a sequence comprising substantial sequence identity to SEQ ID NO:7).

The SNP markers SNP_01 to SNP_07 are located in the given order on the introgression fragment. Consecutive markers refers to markers in the same consecutive order, so e.g. two consecutive markers may be SNP_01 and SNP_02; SNP_02 and SNP_03; SNP_03 and SNP_04, etc. and three consecutive markers may be SNP_01 and SNP_02 and SNP_03; SNP_02 and SNP_03 and SNP_04; etc.

The fragment may, thus, be smaller and lack 1, 2, 3, 4, 5 or even 6 of the markers, but it may still confer Nr:1 resistance on the cultivated lettuce plant, i.e. it can still comprise the Nr:1 allele. Such smaller introgression fragments are an embodiment of the invention.

Plants having smaller introgression fragments can be generated e.g. by starting with a plant comprising a large introgression fragment and crossing such a plant with another cultivated lettuce plant and selfing the progeny of said cross to generate a population of plants which may contain recombinants having a smaller introgression fragment on chromosome 6. Marker assays can be used to determine the size of the smaller introgression fragment. One or more of SNP markers SNP_01 to SNP_07 may be missing (i.e. the plant may only comprise 1, 2, 3, 4, 5, 6 of the SNP markers). The Nr:1 resistance phenotype of plants comprising such a smaller introgression fragment can then be determined as described herein, i.e. growing a plurality of plants comprising the smaller introgression fragment in a controlled environment or field experiments together with suitable control plants, lacking the introgression fragment. The assay may be a free choice or non-choice assay, as the resistance identified herein confers both types of resistance. The control plants are preferably a genetic control or a susceptible variety, such as Mafalda. If the Nr:1 resistance remains significantly higher than in the control, then the smaller introgression fragment has retained the QTL6.1 (or a variant thereof).

Alternatively, the same or variant QTL (QTL6.1 or variant QTL6.1) may be introgressed from a different wild source, whereby optionally not all SNP markers disclosed herein may be present. Such alternative wild sources are preferably *L. virosa* accessions. They can be identified using the SNP markers provided herein, by screening wild germplasm (e.g. *L. virosa* accessions) using a marker assay to detect the genotype of markers SNP_01 to SNP_07 or any marker in-between SNP_01 and SNP_07. Alternatively such wild sources can be identified phenotypically and optionally screened at a later stage for the presence of one or more of the markers described, or optionally progeny from crosses with such accessions can be screened for the markers. Plants comprising the same or variant QTL6.1 from other sources are also an embodiment of the invention. As long as at least 1, 2, 3, 4, 5, 6 or more of the SNPs, preferably at least 2, 3, 4, 5, 6 or more consecutive SNP markers of SNP_01 to SNP_07 also have the SNP genotype indicative of the QTL, the plant comprises QTL6.1 (or a variant thereof). The skilled person can introgress the QTL6.1 (or a variant thereof) into cultivated lettuce in order confer Nr:1 resistance as described herein.

In a specific embodiment the plant of the invention comprises an introgression fragment comprising at least a subset of SNP markers, i.e. at least 1, 2, 3, 4, or all 5 of the following markers selected from the group consisting of:
a) the CC or CT genotype for the Single Nucleotide Polymorphism marker SNP_02 in SEQ ID NO: 2 (or in a sequence comprising substantial sequence identity to SEQ ID NO:2);
b) the AA or AC genotype for the Single Nucleotide Polymorphism marker SNP_03 in SEQ ID NO: 3 (or in a sequence comprising substantial sequence identity to SEQ ID NO:3);
c) the GG or GA genotype for the Single Nucleotide Polymorphism marker SNP_04 in SEQ ID NO: 4 (or in a sequence comprising substantial sequence identity to SEQ ID NO:4);
d) the TT or TC genotype for the Single Nucleotide Polymorphism marker SNP_05 in SEQ ID NO: 5 (or in a sequence comprising substantial sequence identity to SEQ ID NO:5);
e) the CC or CA genotype for the Single Nucleotide Polymorphism marker SNP_06 in SEQ ID NO: 6 (or in a sequence comprising substantial sequence identity to SEQ ID NO:6); and optionally
f) any wild lettuce, especially *L. virosa*, genome-specific marker between SNP_02 and SNP_06.

Preferably, the plant of the invention comprises an introgression fragment comprising at least SNP markers SNP_03, SNP_04, SNP_05 and/or SNP_06 (or any marker in-between any of these), especially at least SNP_04, SNP_05 and/or SNP_06 (or any marker in-between any of these).

Thus, the introgression fragment (and a cultivated lettuce plant or plant part, e.g., a cell, comprising the introgression fragment) can be detected in a marker assay by detecting the SNP genotype of the introgression fragment (i.e. of the wild lettuce, e.g. *L. virosa* germplasm) of one or more or all of the markers above.

In yet another aspect, the plant of the invention comprises an introgression fragment comprising at least SNP_04, i.e. the introgression fragment is detected in a marker assay detecting the GG or GA genotype for the Single Nucleotide Polymorphism marker SNP_04 in SEQ ID NO: 4. Optionally also the flanking markers, SNP_03 and/or SNP_05 are detected, i.e. the introgression fragment is detected in a marker assay detecting at least SNP_04 and optionally also at least one of the following markers:
the TT or TC genotype for the Single Nucleotide Polymorphism marker SNP_05 in SEQ ID NO: 5 (or in a sequence comprising substantial sequence identity to SEQ ID NO:5); and/or
the AA or AC genotype for the Single Nucleotide Polymorphism marker SNP_03 in SEQ ID NO: 3 (or in a sequence comprising substantial sequence identity to SEQ ID NO:3); and optionally
any wild lettuce, especially *L. virosa*, genome-specific marker between SNP_03 and SNP_05.

Lettuce Plants Comprising an Introgression Fragment on Chromosome 6 (Comprising QTL 6.1 or a Variant Thereof)

Based on the later QTL mapping data the QTL region could be specified and cultivated lettuce plants comprising an introgression fragment from *Lactuca virosa*, wherein the introgression fragment comprises QTL6.1 (or a variant thereof) are provided, whereby the introgression fragment comprises all or part of the region starting at 77 Mb on chromosome 6 and ending at 161 Mb on chromosome 6.

Thus, in one aspect a *Lactuca sativa* plant comprising an introgression fragment from *Lactuca virosa* on chromosome 6 is provided which comprises a Quantitative Trait Locus that confers resistance against *Nasonovia ribisnigri* biotype 1 (Nr:1), and wherein the introgression fragment on chromosome 6 comprises all or part of the region starting at 77 Mb and ending at 161 Mb of chromosome 6.

It is understood that a smaller introgression fragment (i.e. comprising a resistance conferring part of the above mentioned region spanning 77 Mb to 161 Mb of chromosome 6) which retains the QTL6.1 (or variant) may be a fragment having a size of 80 Mb, 70 Mb, 60 Mb, 50 Mb, 40 Mb, 30 Mb, 20 Mb, 10 Mb, 5 Mb, 2.5 Mb, 2 Mb, 1 Mb, 0.5 Mb, 100 kb, 50 kb or less and comprise the QTL6.1 or a variant thereof. In one aspect the part is at least 5 kb, 10 kb, 20 kb in size, or more.

In one aspect, the introgression fragment on chromosome 6 is comprises and is detectable by a molecular marker assay which detects at least one, preferably at least 2 or 3 or 4 or 5 (or more) of the markers selected from the group consisting of:
 a) The CC or CT genotype for the Single Nucleotide Polymorphism marker SNP1.23 in SEQ ID NO: 23 (or in a sequence comprising substantial sequence identity to SEQ ID NO: 23);
 b) the CC or CT genotype for the Single Nucleotide Polymorphism marker SNP_02 in SEQ ID NO: 2 (or in a sequence comprising substantial sequence identity to SEQ ID NO: 2);
 c) the TT or CT genotype for the Single Nucleotide Polymorphism marker SNP2.24 in SEQ ID NO: 24 (or in a sequence comprising substantial sequence identity to SEQ ID NO: 24);
 the AA or AC genotype for the Single Nucleotide Polymorphism marker SNP_03 in SEQ ID NO: 3 (or in a sequence comprising substantial sequence identity to SEQ ID NO: 3);
 d) any wild lettuce genome specific marker, especially *L. virosa*-genome specific marker, located physically in-between SNP1.23 and SNP_03 (e.g. in-between SNP1.23 and SNP2.24, SNP1.23 and SNP_02); or in between SNP_02 and SNP_03 (e.g. in-between SNP_02 and SNP2.24); or in between SNP2.24 and SNP_03;
 e) any wild lettuce genome specific marker especially *L. virosa*-genome specific marker, located within a distance of 10 Mb, preferably within 5 Mb, of any marker selected from SNP1.23, SNP_02, SNP2.24, or SNP_03.

Optionally, in one aspect, the introgression fragment comprises (and is detectable by) a *L. virosa* accession specific marker selected from the GG or GT genotype for the Single Nucleotide Polymorphism marker VSP1 in SEQ ID NO: 26 (or in a sequence comprising substantial sequence identity to SEQ ID NO: 26) and the AA or AC genotype for the Single Nucleotide Polymorphism marker VSP3 in SEQ ID NO: 27 (or in a sequence comprising substantial sequence identity to SEQ ID NO: 27). Using the SNP markers VSP1 and VSP3 the introgression fragments comprising QTL6.1 from different *L. virosa* type accessions can be distinguished.

The introgression fragment may be in heterozygous or homozygous form, as indicated by the SNP genotype. So in one aspect the introgression fragment is in homozygous form and the SNP marker genotype is the homozygous genotype.

As mentioned, variants of QTL6.1 may be identified and introgressed from various Nr:1 resistant *Lactuca virosa* accessions. Such variants may comprise a genomic sequence which is not 100% identical to the sequences provided herein, but may still have substantial sequence identity (such as at least 85%, 90% or more) when genomic sequences of the same lengths are aligned. That there is variation in the QTL region where QTL6.1 is located can be seen due to the fact that accession specific SNP markers could be identified in introgressions of QTL6.1 from two different *L. virosa* accessions, which introgressions however both comprise the resistance conferring QTL6.1. So the introgression fragment comprising VSP1 is a different introgression fragment than the one comprising VSP3, but both comprise QTL6.1. Within wild *L. virosa* accessions, which comprise QTL6.1, there may, thus, be genomic variation in the region spanning 77 Mb to 161 Mb on chromosome 6. However, such accessions may equally be used to introgress all or part of the region starting at 77 Mb and ending at 161 Mb of chromosome 6 into Nr: 1 susceptible cultivated lettuce, in order to generate plants of the invention. With the knowledge of the instant invention, that the region comprises a QTL, the skilled person can introgress the same region or a smaller resistance conferring part into cultivated lettuce.

In one aspect the introgression fragment on chromosome 6 is comprises, and is detectable by a molecular marker assay which detects, at least one, preferably at least 2 or 3 or 4 of the markers selected from the group consisting of:
 a) The CC or CT genotype for the Single Nucleotide Polymorphism marker SNP1.23 in SEQ ID NO: 23 or in a sequence comprising substantial sequence identity to SEQ ID NO: 23;
 b) the CC or CT genotype for the Single Nucleotide Polymorphism marker SNP_02 in SEQ ID NO: 2 or in a sequence comprising substantial sequence identity to SEQ ID NO: 2;
 c) the TT or CT genotype for the Single Nucleotide Polymorphism marker SNP2.24 in SEQ ID NO: 24 or in a sequence comprising substantial sequence identity to SEQ ID NO: 24;
 d) the AA or AC genotype for the Single Nucleotide Polymorphism marker SNP_03 in SEQ ID NO: 3 or in a sequence comprising substantial sequence identity to SEQ ID NO: 3.

In one aspect the introgression fragment is derivable from seeds deposited under NCIMB42086 or progeny thereof.

In one aspect the introgression fragment is from another Nr:1 resistant *L. virosa* accession, such as an accession comprising the AA or AC genotype for the Single Nucleotide Polymorphism marker VSP3 in SEQ ID NO: 27 (or in a sequence comprising substantial sequence identity to SEQ ID NO: 27).

In another aspect the introgression fragment is from another Nr:1 resistant *L. virosa* accession, such as an accession comprising the GG or GT genotype for the Single Nucleotide Polymorphism marker VSP1 in SEQ ID NO: 26 (or in a sequence comprising substantial sequence identity to SEQ ID NO: 26).

Other aspects, described elsewhere based on the first QTL analysis and markers SNP_01 to SNP_07 equally apply to the markers and introgression identified in this later analysis. So, for example, QTL6.1 can be introgressed into any cultivated lettuce, especially Nr:1 susceptible lines or varieties by e.g. backcrossing. It can also be combined in cultivated lettuce with a recombinant chromosome 7, comprising QTL7.1 and/or QTL7.2.

Lettuce Plants Comprising an Introgression Fragment on Chromosome 7 (QTL 7.1 and/or QTL7.2 or Variants of these)

Based on the first QTL mapping results, the following cultivated lettuce plants are encompassed herein.

In one aspect the introgression fragment comprising QTL 7.2 or a variant thereof (and the cultivated lettuce plant or plant part comprising the introgression fragment) on chromosome 7 is detectable by a molecular marker assay which detects at least 1, preferably at least 2 or 3, or at least 4, 5, 6, or 7 of the markers selected from the group consisting of:
  a) the TT or TC genotype for the Single Nucleotide Polymorphism marker SNP_08 in SEQ ID NO: 8 (or in a sequence comprising substantial sequence identity to SEQ ID NO:8);
  b) the CC or CT genotype for the Single Nucleotide Polymorphism marker SNP_09 in SEQ ID NO: 9 (or in a sequence comprising substantial sequence identity to SEQ ID NO:9);
  c) the AA or AG genotype for the Single Nucleotide Polymorphism marker SNP_10 in SEQ ID NO: 10 (or in a sequence comprising substantial sequence identity to SEQ ID NO:10);
  d) the CC or CA genotype for the Single Nucleotide Polymorphism marker SNP_11 in SEQ ID NO: 11 (or in a sequence comprising substantial sequence identity to SEQ ID NO: 11);
  e) the CC or CT genotype for the Single Nucleotide Polymorphism marker SNP_12 in SEQ ID NO: 12 (or in a sequence comprising substantial sequence identity to SEQ ID NO:12);
  f) the GG or GA genotype for the Single Nucleotide Polymorphism marker SNP_13 in SEQ ID NO: 13 (or in a sequence comprising substantial sequence identity to SEQ ID NO:13);
  g) the CC or CT genotype for the Single Nucleotide Polymorphism marker SNP_14 in SEQ ID NO: 14 (or in a sequence comprising substantial sequence identity to SEQ ID NO:14);
  h) any wild lettuce genome specific marker, especially *L. virosa*-genome specific marker, located physically in-between SNP_08 and SNP_14 (e.g. in-between SNP_08 and SNP_13, SNP_08 and SNP_12, SNP_08 and SNP_11, SNP_08 and SNP_10, SNP_08 and SNP_09); or in between SNP_09 and SNP_14 (e.g. in-between SNP_09 and SNP_13, SNP_09 and SNP_12, SNP_09 and SNP_11, SNP_09 and SNP_10); or in between SNP_10 and SNP_14 (e.g. in-between SNP_10 and SNP_13, SNP_10 and SNP_12, SNP_10 and SNP_11); or in between SNP_11 and SNP_14 (e.g. in-between SNP_11 and SNP_13, SNP_11 and SNP_12); or in between SNP_12 and SNP_14 (e.g. in-between SNP_12 and SNP_13); or in between SNP_13 and SNP_14.

As mentioned, the skilled person can also develop other molecular markers, e.g. a wild lettuce genome specific marker, e.g. *L. virosa* genome-specific markers in between marker SNP_08 and SNP_14 and/or within 7 cM or within 5 cM of any one of SNP_08 to SNP_14, and/or within 5 Mb, 3 Mb, 2.5 Mb, 2 Mb, 1 Mb, 0.5 Mb, 0.4 Mb, 0.3 Mb, 0.2 Mb, 0.1 Mb, 50 kb, 20 kb, 10 kb, 5 kb or less of any one of SNP_08 to SNP_14. Such markers may also be a stretch of nucleotide, CAPS markers, INDELs, etc.

In another aspect the introgression fragment on chromosome 7 (comprising QTL 7.2 or a variant) is detectable by a molecular marker assay which detects at least 1, preferably at least 2 or 3, or at least 4, 5, 6, or all 7 of the markers selected from the group consisting of:
  a) the TT or TC genotype for the Single Nucleotide Polymorphism marker SNP_08 in SEQ ID NO: 8 (or in a sequence comprising substantial sequence identity to SEQ ID NO:8);
  b) the CC or CT genotype for the Single Nucleotide Polymorphism marker SNP_09 in SEQ ID NO: 9 (or in a sequence comprising substantial sequence identity to SEQ ID NO:9);
  c) the AA or AG genotype for the Single Nucleotide Polymorphism marker SNP_10 in SEQ ID NO: 10 (or in a sequence comprising substantial sequence identity to SEQ ID NO:10);
  d) the CC or CA genotype for the Single Nucleotide Polymorphism marker SNP_11 in SEQ ID NO: 11 (or in a sequence comprising substantial sequence identity to SEQ ID NO: 11);
  e) the CC or CT genotype for the Single Nucleotide Polymorphism marker SNP_12 in SEQ ID NO: 12 (or in a sequence comprising substantial sequence identity to SEQ ID NO:12);
  f) the GG or GA genotype for the Single Nucleotide Polymorphism marker SNP_13 in SEQ ID NO: 13 (or in a sequence comprising substantial sequence identity to SEQ ID NO:13);
  g) the CC or CT genotype for the Single Nucleotide Polymorphism marker SNP_14 in SEQ ID NO: 14 (or in a sequence comprising substantial sequence identity to SEQ ID NO: 14).

In another aspect a cultivated lettuce plant is provided comprising an introgression fragment on chromosome 7 in homozygous or heterozygous form, wherein said introgression fragment comprises QTL7.2 conferring Nr:1 resistance and wherein said introgression fragment is detectable by a molecular marker assay which detects at least 2, 3 or 4 (or at least 5, 6, 7) consecutive markers selected from the group consisting of:
  a) the TT or TC genotype for the Single Nucleotide Polymorphism marker SNP_08 in SEQ ID NO: 8 (or in a sequence comprising substantial sequence identity to SEQ ID NO:8);
  b) the CC or CT genotype for the Single Nucleotide Polymorphism marker SNP_09 in SEQ ID NO: 9 (or in a sequence comprising substantial sequence identity to SEQ ID NO:9);
  c) the AA or AG genotype for the Single Nucleotide Polymorphism marker SNP_10 in SEQ ID NO: 10 (or in a sequence comprising substantial sequence identity to SEQ ID NO:10);
  d) the CC or CA genotype for the Single Nucleotide Polymorphism marker SNP_11 in SEQ ID NO: 11 (or in a sequence comprising substantial sequence identity to SEQ ID NO: 11);
  e) the CC or CT genotype for the Single Nucleotide Polymorphism marker SNP_12 in SEQ ID NO: 12 (or in a sequence comprising substantial sequence identity to SEQ ID NO:12);
  f) the GG or GA genotype for the Single Nucleotide Polymorphism marker SNP_13 in SEQ ID NO: 13 (or in a sequence comprising substantial sequence identity to SEQ ID NO:13);
  g) the CC or CT genotype for the Single Nucleotide Polymorphism marker SNP_14 in SEQ ID NO: 14 (or in a sequence comprising substantial sequence identity to SEQ ID NO:14).

The SNP markers SNP_08 to SNP_14 are located in the given order on the introgression fragment. Consecutive markers refers to markers in the same consecutive order, so e.g. two consecutive markers may be SNP_08 and SNP_09; SNP_09 and SNP_10; SNP_10 and SNP_11, etc. and three consecutive markers may be SNP_08 and SNP_09 and SNP_10; SNP_09 and SNP_10 and SNP_11; etc.

The fragment may, thus, be smaller and lack 1, 2, 3, 4, 5, 6 of the markers, but it may still confer Nr:1 resistance on the cultivated lettuce plant, i.e. it can still comprise the Nr:1 allele. Such smaller introgression fragments are an embodiment of the invention. Plants having smaller introgression fragments can be generated e.g. by starting with a plant comprising a large introgression fragment and crossing such a plant with another cultivated lettuce plant and selfing the progeny of said cross to generate a population of plants which may contain recombinants having a smaller introgression fragment on chromosome 7. Marker assays can be used to determine the size of the smaller introgression fragment. One or more of SNP markers SNP_08 to SNP_14 may be missing (i.e. the plant may only comprise 1, 2, 3, 4, 5, or 6 of the SNP markers). The Nr:1 resistance of plants comprising such a smaller introgression fragment can then be compared in Nr: 1 assays as described herein, i.e. growing a plurality of plants comprising the smaller introgression fragment in field experiments together with suitable control plants, lacking the introgression fragment. The control plants are preferably a genetic control or a susceptible control such as Mafalda. If the Nr:1 resistance remains significantly higher than in the control, then the smaller introgression fragment has retained the QTL7.2 (or variant).

Alternatively, the same or variant QTL (QTL7.2 or variant QTL7.2) may be introgressed from a different wild source, such as different *L. virosa* accessions, whereby optionally not all SNP markers disclosed herein may be present. Such alternative wild sources can be identified using the SNP markers provided herein, by screening wild germplasm, e.g. *L. virosa* accessions using a marker assay to detect the genotype of markers SNP_08 to SNP_14, or a marker in between these. Alternatively such wild sources can be identified phenotypically and optionally screened at a later stage for the presence of one or more of the markers described, or optionally progeny from crosses with such accessions can be screened for the markers. Plants comprising the QTL7.2 or variant QTL7.2 from other sources are also an embodiment of the invention. As long as at least 1, 2, 3, 4, 5, 6, or 7 or more of the SNPs, preferably at least 2, 3, 4, 5, 6, or 7 consecutive SNP markers of SNP_08 to SNP_14 also have SNP genotype indicative of the QTL, the plant comprises QTL7.2 (or a variant thereof). The skilled person can introgress the QTL7.2 (or a variant thereof) into cultivated lettuce in order to generate Nr: 1 resistance as described herein.

In a specific embodiment the plant of the invention comprises an introgression fragment comprising at least a subset of SNP markers, i.e. at least 1, 2, 3, 4 or all 5 of the following markers selected from the group consisting of:
  a) the TT or TC genotype for the Single Nucleotide Polymorphism marker SNP_08 in SEQ ID NO: 8 (or in a sequence comprising substantial sequence identity to SEQ ID NO:8);
  b) the CC or CT genotype for the Single Nucleotide Polymorphism marker SNP_09 in SEQ ID NO: 9 (or in a sequence comprising substantial sequence identity to SEQ ID NO:9);
  c) the AA or AG genotype for the Single Nucleotide Polymorphism marker SNP_10 in SEQ ID NO: 10 (or in a sequence comprising substantial sequence identity to SEQ ID NO:10);
  d) the CC or CA genotype for the Single Nucleotide Polymorphism marker SNP_11 in SEQ ID NO: 11 (or in a sequence comprising substantial sequence identity to SEQ ID NO: 11);
  e) the CC or CT genotype for the Single Nucleotide Polymorphism marker SNP_12 in SEQ ID NO: 12 (or in a sequence comprising substantial sequence identity to SEQ ID NO:12); and optionally
  f) any wild lettuce genome-specific marker, such as a *L. virosa* genome specific marker, in between marker SNP_08 and SNP_12.

Especially, in one aspect the cultivated lettuce plant of the invention comprises at least 1, 2 or 3 markers selected from the group consisting of:
  a) the CC or CT genotype for the Single Nucleotide Polymorphism marker SNP_09 in SEQ ID NO: 9 (or in a sequence comprising substantial sequence identity to SEQ ID NO:9);
  b) the AA or AG genotype for the Single Nucleotide Polymorphism marker SNP_10 in SEQ ID NO: 10 (or in a sequence comprising substantial sequence identity to SEQ ID NO:10);
  c) the CC or CA genotype for the Single Nucleotide Polymorphism marker SNP_11 in SEQ ID NO: 11 (or in a sequence comprising substantial sequence identity to SEQ ID NO:11); and optionally
  d) any wild lettuce genome-specific marker, such as a *L. virosa* genome specific marker, in between marker SNP_09 and SNP_11.

Thus, the introgression fragment (and a cultivated lettuce plant or plant part, e.g., a cell, comprising the introgression fragment) can be detected in a marker assay by detecting the SNP genotype of the introgression fragment (i.e. of the wild lettuce germplasm) of one or more or all of the markers above.

In one aspect the introgression fragment comprising QTL 7.1 (and the cultivated lettuce plant or plant part comprising the introgression fragment) on chromosome 7 is detectable by a molecular marker assay which detects at least 1, preferably at least 2 or 3, or at least 4, 5, 6, 7 or 8 of the markers selected from the group consisting of:
  a) the TT or TA genotype for the Single Nucleotide Polymorphism marker SNP_15 in SEQ ID NO: 15 (or in a sequence comprising substantial sequence identity to SEQ ID NO: 15);
  b) the GG or GA genotype for the Single Nucleotide Polymorphism marker SNP_16 in SEQ ID NO: 16 (or in a sequence comprising substantial sequence identity to SEQ ID NO:16);
  c) the TT or TC genotype for the Single Nucleotide Polymorphism marker SNP_17 in SEQ ID NO: 17 (or in a sequence comprising substantial sequence identity to SEQ ID NO:17);
  d) the GG or GC genotype for the Single Nucleotide Polymorphism marker SNP_18 in SEQ ID NO: 18 (or in a sequence comprising substantial sequence identity to SEQ ID NO:18);
  e) the GG or GA genotype for the Single Nucleotide Polymorphism marker SNP_19 in SEQ ID NO: 19 (or in a sequence comprising substantial sequence identity to SEQ ID NO:19);

f) the TT or TC genotype for the Single Nucleotide Polymorphism marker SNP_20 in SEQ ID NO: 20 (or in a sequence comprising substantial sequence identity to SEQ ID NO:20);

g) the CC or CA genotype for the Single Nucleotide Polymorphism marker SNP_21 in SEQ ID NO: 21 (or in a sequence comprising substantial sequence identity to SEQ ID NO:21);

h) the CC or CT genotype for the Single Nucleotide Polymorphism marker SNP_22 in SEQ ID NO: 22 (or in a sequence comprising substantial sequence identity to SEQ ID NO:22);

i) any wild lettuce genome specific marker, especially *L. virosa*-genome specific marker, located physically in-between SNP_15 and SNP_22 (e.g. in-between SNP_15 and SNP_21, SNP_15 and SNP_20, SNP_15 and SNP_19, SNP_15 and SNP_18, SNP_15 and SNP_17, SNP_15 and SNP_16); or in between SNP_16 and SNP_22 (e.g. in-between SNP_16 and SNP_21, SNP_16 and SNP_20, SNP_16 and SNP_19, SNP_16 and SNP_18, SNP_16 and SNP_17); or in between SNP_17 and SNP_22 (e.g. in-between SNP_17 and SNP_21, SNP_17 and SNP_20, SNP_17 and SNP_19, SNP_17 and SNP_18); or in between SNP_18 and SNP_22 (e.g. in-between SNP_18 and SNP_21, SNP_18 and SNP_20, SNP_18 and SNP_19); or in between SNP_19 and SNP_22 (e.g. in-between SNP_19 and SNP_21, SNP_19 and SNP_20); or in between SNP_20 and SNP_22; or in between SNP_21 and SNP_22.

As mentioned, the skilled person can also develop other molecular markers, e.g. a wild lettuce genome specific marker, e.g. *L. virosa* genome-specific markers, in between marker SNP_15 and SNP_22 and/or within 7 cM or within 5 cM of any one of SNP_15 to SNP_22, and/or within 5 Mb, 3 Mb, 2.5 Mb, 2 Mb, 1 Mb, 0.5 Mb, 0.4 Mb, 0.3 Mb, 0.2 Mb, 0.1 Mb, 50 kb, 20 kb, 10 kb, 5 kb or less of any one of SNP_15 to SNP_22. Such markers may also be a stretch of nucleotide, CAPS markers, INDELs, etc.

In another aspect the introgression fragment on chromosome 7 (comprising QTL 7.1 or a variant) is detectable by a molecular marker assay which detects at least 1, preferably at least 2 or 3, or at least 4, 5, 6, 7 or all 8 of the markers selected from the group consisting of:

a) the TT or TA genotype for the Single Nucleotide Polymorphism marker SNP_15 in SEQ ID NO: 15 (or in a sequence comprising substantial sequence identity to SEQ ID NO:15);

b) the GG or GA genotype for the Single Nucleotide Polymorphism marker SNP_16 in SEQ ID NO: 16 (or in a sequence comprising substantial sequence identity to SEQ ID NO:16);

c) the TT or TC genotype for the Single Nucleotide Polymorphism marker SNP_17 in SEQ ID NO: 17 (or in a sequence comprising substantial sequence identity to SEQ ID NO:17);

d) the GG or GC genotype for the Single Nucleotide Polymorphism marker SNP_18 in SEQ ID NO: 18 (or in a sequence comprising substantial sequence identity to SEQ ID NO:18);

e) the GG or GA genotype for the Single Nucleotide Polymorphism marker SNP_19 in SEQ ID NO: 19 (or in a sequence comprising substantial sequence identity to SEQ ID NO:19);

f) the TT or TC genotype for the Single Nucleotide Polymorphism marker SNP_20 in SEQ ID NO: 20 (or in a sequence comprising substantial sequence identity to SEQ ID NO:20);

g) the CC or CA genotype for the Single Nucleotide Polymorphism marker SNP_21 in SEQ ID NO: 21 (or in a sequence comprising substantial sequence identity to SEQ ID NO:21);

h) the CC or CT genotype for the Single Nucleotide Polymorphism marker SNP_22 in SEQ ID NO: 22 (or in a sequence comprising substantial sequence identity to SEQ ID NO:22).

In another aspect a cultivated lettuce plant is provided comprising an introgression fragment on chromosome 7 in homozygous or heterozygous form, wherein said introgression fragment comprises QTL7.1 conferring Nr: 1 resistance and wherein said introgression fragment is detectable by a molecular marker assay which detects at least 2, 3 or 4 (or at least 5, 6, 7, 8) consecutive markers selected from the group consisting of:

a) the TT or TA genotype for the Single Nucleotide Polymorphism marker SNP_15 in SEQ ID NO: 15 (or in a sequence comprising substantial sequence identity to SEQ ID NO:15);

b) the GG or GA genotype for the Single Nucleotide Polymorphism marker SNP_16 in SEQ ID NO: 16 (or in a sequence comprising substantial sequence identity to SEQ ID NO:16);

c) the TT or TC genotype for the Single Nucleotide Polymorphism marker SNP_17 in SEQ ID NO: 17 (or in a sequence comprising substantial sequence identity to SEQ ID NO:17);

d) the GG or GC genotype for the Single Nucleotide Polymorphism marker SNP_18 in SEQ ID NO: 18 (or in a sequence comprising substantial sequence identity to SEQ ID NO:18);

e) the GG or GA genotype for the Single Nucleotide Polymorphism marker SNP_19 in SEQ ID NO: 19 (or in a sequence comprising substantial sequence identity to SEQ ID NO:19);

f) the TT or TC genotype for the Single Nucleotide Polymorphism marker SNP_20 in SEQ ID NO: 20 (or in a sequence comprising substantial sequence identity to SEQ ID NO:20);

g) the CC or CA genotype for the Single Nucleotide Polymorphism marker SNP_21 in SEQ ID NO: 21 (or in a sequence comprising substantial sequence identity to SEQ ID NO:21);

h) the CC or CT genotype for the Single Nucleotide Polymorphism marker SNP_22 in SEQ ID NO: 22 (or in a sequence comprising substantial sequence identity to SEQ ID NO:22).

The SNP markers SNP_15 to SNP_22 are located in the given order on the introgression fragment. Consecutive markers refers to markers in the same consecutive order, so e.g. two consecutive markers may be SNP_12 and SNP_13; SNP_13 and SNP_14; SNP_14 and SNP_15, etc. and three consecutive markers may be SNP_12 and SNP_13 and SNP_14; SNP_13 and SNP_14 and SNP_15; etc.

The fragment may, thus, be smaller and lack 1, 2, 3, 4, 5, 6 or 7 of the markers, but it may still confer Nr:1 resistance on the cultivated lettuce plant, i.e. it can still comprise the Nr:1 allele. Such smaller introgression fragments are an embodiment of the invention. Plants having smaller introgression fragments can be generated e.g. by starting with a plant comprising a large introgression fragment and crossing such a plant with another cultivated lettuce plant and selfing the progeny of said cross to generate a population of plants which may contain recombinants having a smaller introgression fragment on chromosome 7 (comprising QTL 7.1 or a variant). Marker assays can be used to determine the size of the smaller introgression fragment. One or more of SNP markers SNP_15 to SNP_22 may be missing (i.e. the plant may only comprise 1, 2, 3, 4, 5, 6 or 7 of the SNP markers). The Nr:1 resistance of plants comprising such a smaller introgression fragment can then be compared in Nr:1 assays as described herein, i.e. growing a plurality of plants comprising the smaller introgression fragment in field experiments together with suitable control plants, lacking the introgression fragment. The control plants are preferably a genetic control or a susceptible control such as Mafalda. If the Nr: 1 resistance remains significantly higher than in the control, then the smaller introgression fragment has retained the QTL7.1 (or a variant).

Alternatively, the same or variant QTL (QTL7.1 or variant QTL7.1) may be introgressed from a different wild source, such as different *L. virosa* accessions, whereby optionally not all SNP markers disclosed herein may be present. Such alternative wild sources can be identified using the SNP markers provided herein, by screening wild germplasm, e.g. *L. virosa* accessions using a marker assay to detect the genotype of markers SNP_15 to SNP_22, or a marker in-between these. Alternatively such wild sources can be identified phenotypically and optionally screened at a later stage for the presence of one or more of the markers described, or optionally progeny from crosses with such accessions can be screened for the markers. Plants comprising the QTL7.1 or variant QTL7.1 from other sources are also an embodiment of the invention. As long as at least 1, 2, 3, 4, 5, 6, 7 or 8 or more of the SNPs, preferably at least 2, 3, 4, 5, 6, 7 or 8 consecutive SNP markers of SNP_15 to SNP_22 also have SNP genotype indicative of the QTL, the plant comprises QTL7.1 (or a variant thereof). The skilled person can introgress the QTL7.1 (or a variant thereof) into cultivated lettuce in order to generate Nr:1 resistance as described herein.

In a specific embodiment the plant of the invention comprises an introgression fragment comprising at least a subset of SNP markers, i.e. at least 1, 2, 3, 4 or all 5 of the following markers selected from the group consisting of:
a) the TT or TC genotype for the Single Nucleotide Polymorphism marker SNP_17 in SEQ ID NO: 17 (or in a sequence comprising substantial sequence identity to SEQ ID NO:17);
b) the GG or GC genotype for the Single Nucleotide Polymorphism marker SNP_18 in SEQ ID NO: 18 (or in a sequence comprising substantial sequence identity to SEQ ID NO: 18);
c) the GG or GA genotype for the Single Nucleotide Polymorphism marker SNP_19 in SEQ ID NO: 19 (or in a sequence comprising substantial sequence identity to SEQ ID NO:19);
d) the TT or TC genotype for the Single Nucleotide Polymorphism marker SNP_20 in SEQ ID NO: 20 (or in a sequence comprising substantial sequence identity to SEQ ID NO:20);
e) the CC or CA genotype for the Single Nucleotide Polymorphism marker SNP_21 in SEQ ID NO: 21 (or in a sequence comprising substantial sequence identity to SEQ ID NO:21); and optionally
f) any wild lettuce genome-specific marker, such as a *L. virosa* genome specific marker, in between marker SNP_19 and SNP_21.

Especially, in one aspect the cultivated lettuce plant of the invention comprises at least 1, 2 or 3 markers selected from the group consisting of:
a) the GG or GA genotype for the Single Nucleotide Polymorphism marker SNP_19 in SEQ ID NO: 19 (or in a sequence comprising substantial sequence identity to SEQ ID NO:19);
b) the TT or TC genotype for the Single Nucleotide Polymorphism marker SNP_20 in SEQ ID NO: 20 (or in a sequence comprising substantial sequence identity to SEQ ID NO:20);
c) the CC or CA genotype for the Single Nucleotide Polymorphism marker SNP_21 in SEQ ID NO: 21 (or in a sequence comprising substantial sequence identity to SEQ ID NO:21); and optionally
d) any wild lettuce genome-specific marker, such as a *L. virosa* genome specific marker, in between marker SNP_19 and SNP_21.

Thus, the introgression fragment (and a cultivated lettuce plant or plant part, e.g., a cell, comprising the introgression fragment) can be detected in a marker assay by detecting the SNP genotype of the introgression fragment (i.e. of the wild lettuce germplasm) of one or more or all of the markers above.

Lettuce Plants Comprising an Introgression Fragment on Chromosome 7 (QTL 7.1 or a Variant Thereof)

Based on the later QTL mapping data the QTL7.1 region could be specified and cultivated lettuce plants comprising an introgression fragment from *Lactuca virosa*, wherein the introgression fragment comprises QTL7.1 (or a variant thereof) are provided, whereby the introgression fragment comprises all or part of the region starting at 203 Mb on chromosome 7 and ending at 219 Mb on chromosome 7.

Thus, in one aspect a *Lactuca sativa* plant comprising an introgression fragment from *Lactuca virosa* on chromosome 7 is provided which comprises a Quantitative Trait Locus that confers resistance against *Nasonovia ribisnigri* biotype 1 (Nr:1), and wherein the introgression fragment on chromosome 7 comprises all or part of the region starting at 203 Mb on chromosome 7 and ending at 219 Mb of chromosome 7.

It is understood that a smaller introgression fragment (i.e. comprising a resistance conferring part of the above mentioned region spanning 203 Mb to 219 Mb of chromosome 7) which retains the QTL7.1 (or variant) may be a fragment having a size of 15 Mb, 10 Mb, 5 Mb, 2.5 Mb, 2 Mb, 1 Mb, 0.5 Mb, 100 kb, 50 kb or less and comprise the QTL7.1 or a variant thereof. In one aspect the part is at least 5 kb, 10 kb, 20 kb in size, or more.

In one aspect, the introgression fragment on chromosome 7 is comprises and is detectable by a molecular marker assay which detects at least one, preferably at least 2 or 3 or 4 or 5 (or more) of the markers selected from the group consisting of:
a) the TT or TC genotype for the Single Nucleotide Polymorphism marker SNP_17 in SEQ ID NO: 17 (or in a sequence comprising substantial sequence identity to SEQ ID NO: 17);
b) the TT or TC genotype for the Single Nucleotide Polymorphism marker SNP17.25 in SEQ ID NO: 25 (or in a sequence comprising substantial sequence identity to SEQ ID NO: 25);
c) the GG or GC genotype for the Single Nucleotide Polymorphism marker SNP_18 in SEQ ID NO: 18 (or in a sequence comprising substantial sequence identity to SEQ ID NO: 18);

d) the GG or GA genotype for the Single Nucleotide Polymorphism marker SNP_19 in SEQ ID NO: 19 (or in a sequence comprising substantial sequence identity to SEQ ID NO: 19);
e) any wild lettuce genome specific marker, especially *L. virosa*-genome specific marker, located physically in-between SNP_17 and SNP_19 (e.g. in-between SNP_17 and SNP_18, in between SNP_17 and SNP17.25; or in between SNP17.25 and SNP_19, or in between SNP17.25 and SNP_18, or in between SNP_18 and SNP_19);
f) any wild lettuce genome specific marker especially *L. virosa*-genome specific marker, located within a distance of 12 Mb or of 10 Mb, preferably within 5 Mb, of any marker selected from SNP_17, SNP_17.25, SNP_18 and SNP_19.

Optionally, in one aspect, the introgression fragment comprises (and is detectable by) a *L. virosa* accession specific marker selected from the CC or AC genotype for the Single Nucleotide Polymorphism marker VSP2 in SEQ ID NO: 28 (or in a sequence comprising substantial sequence identity to SEQ ID NO: 28) and the GG or GA genotype for the Single Nucleotide Polymorphism marker VSP4 in SEQ ID NO: 29 (or in a sequence comprising substantial sequence identity to SEQ ID NO: 29). Using the SNP markers VSP2 and VSP4 the introgression fragments comprising QTL7.1 from two different types *L. virosa* accessions can be distinguished.

The introgression fragment may be in heterozygous or homozygous form, as indicated by the SNP genotype. So in one aspect the introgression fragment is in homozygous form and the SNP marker genotype is the homozygous genotype.

As mentioned, variants of QTL7.1 may be identified and introgressed from various Nr:1 resistant *Lactuca virosa* accessions. Such variants may comprise a genomic sequence which is not 100% identical to the sequences provided herein, but may still have substantial sequence identity (such as at least 85%, 900 or more) when genomic sequences of the same lengths are aligned. That there is variation in the QTL region where QTL7.1 is located can be seen due to the fact that accession specific SNP markers could be identified in introgressions of QTL7.1 from two different *L. virosa* accessions, which introgressions however both comprise the resistance conferring QTL7.1. So the introgression fragment comprising VSP2 is a different introgression fragment than the one comprising VSP4, but both comprise QTL7.1. Within wild *L. virosa* accessions, which comprise QTL7.1, there may, thus, be genomic variation in the region spanning 203 Mb to 219 Mb on chromosome 7. However, such accessions may equally be used to introgress all or part of the region starting at 203 Mb and ending at 219 Mb of chromosome 7 into Nr: 1 susceptible cultivated lettuce, in order to generate plants of the invention. With the knowledge of the instant invention, that the region comprises a QTL, the skilled person can introgress the same region or a smaller resistance conferring part into cultivated lettuce.

In one aspect the introgression fragment on chromosome 7 is comprises, and is detectable by a molecular marker assay which detects, at least one, preferably at least 2 or 3 or 4 of the markers selected from the group consisting of:
a) the TT or TC genotype for the Single Nucleotide Polymorphism marker SNP_17 in SEQ ID NO: 17 (or in a sequence comprising substantial sequence identity to SEQ ID NO: 17);
b) the TT or TC genotype for the Single Nucleotide Polymorphism marker SNP17.25 in SEQ ID NO: 25 (or in a sequence comprising substantial sequence identity to SEQ ID NO: 25);
c) the GG or GC genotype for the Single Nucleotide Polymorphism marker SNP_18 in SEQ ID NO: 18 (or in a sequence comprising substantial sequence identity to SEQ ID NO: 18);
d) the GG or GA genotype for the Single Nucleotide Polymorphism marker SNP_19 in SEQ ID NO: 19 (or in a sequence comprising substantial sequence identity to SEQ ID NO: 19);

In one aspect the introgression fragment is derivable from seeds deposited under NCIMB42086 or progeny thereof.

In one aspect the introgression fragment is from another Nr:1 resistant *L. virosa* accession, such as an accession comprising the GG or GA genotype for the Single Nucleotide Polymorphism marker VSP4 in SEQ ID NO: 29 (or in a sequence comprising substantial sequence identity to SEQ ID NO:29).

In another aspect the introgression fragment is from another Nr:1 resistant *L. virosa* accession, such as an accession comprising the CC or CA genotype for the Single Nucleotide Polymorphism marker VSP2 in SEQ ID NO: 28 (or in a sequence comprising substantial sequence identity to SEQ ID NO:28).

Other aspects, described elsewhere based on the first QTL analysis of QTL7.1 and markers SNP_15 to SNP_22 equally apply to the markers and introgression identified in this later analysis. So, for example, QTL7.1 can be introgressed into any cultivated lettuce, especially Nr:1 susceptible lines or varieties by e.g. backcrossing. It can also be combined in cultivated lettuce with a recombinant chromosome 6 comprising QTL6.1 and/or with a second QTL on chromosome 7, namely QTL7.2.

Thus, in one aspect three Quantitative Trait Loci (QTL6.1 and/or QTL7.1 and/or QTL7.2) were found to be present on chromosome 6 and 7 of wild lettuce (especially *L. virosa*, such as accession NCIMB42086) which, when transferred (introgressed) into a cultivated lettuce variety or breeding line separately or in combination, and when present in heterozygous or homozygous form, confer Nr:1 resistance onto the cultivated lettuce plant. In one aspect the cultivated lettuce plant comprises the introgression fragment(s) on only one of the chromosome 6 and/or 7, while the homologous chromosomes 6 and 7 of the pair may be a non-recombinant chromosome 6 and/or 7 of cultivate lettuce lacking the introgression fragment(s). In another aspect the cultivated lettuce plant comprises the introgression fragment(s) on both of the chromosome 6 and/or 7 of the homologous pair (the introgression is in homozygous form). Genotypes of the cultivated lettuce plants may thus be for plants comprising a single introgression fragment: QTL6.1/wt, QTL6.1/QTL6.1, QTL7.1/wt, QTL7.1/QTL7.1, QTL7.2/wt, QTL7.2/QTL7.2; for plants comprising two introgression fragments, one on chromosome 6 and one on chromosome 7: QTL6.1/wt plus QTL7.1/wt, QTL6.1/QTL6.1 plus QTL7.1/wt, QTL6.1/QTL6.1 plus QTL7.1/QTL7.1, QTL6.1/wt plus QTL7.1/QTL7.1; QTL6.1/wt plus QTL7.2/wt, QTL6.1/QTL6.1 plus QTL7.2/wt, QTL6.1/QTL6.1 plus QTL7.2/QTL7.2, QTL6.1/wt plus QTL7.2/QTL7.2; for plants comprising two introgression fragments on chromosome 7: QTL7.2/wt plus QTL7.1/wt, QTL7.2/QTL7.2 plus QTL7.1/wt, QTL7.2/QTL7.2 plus QTL7.1/QTL7.1, QTL7.2/wt plus QTL7.1/QTL7.1. The plants comprising two introgression fragments, one on chromosome 6 and one on chromosome 7, as described above, may additionally comprise the third QTL on chromosome 7 in heterozygous or homozygous form.

The introgression fragments may be from the same accession, but they may also be from different accessions. In one aspect, the introgression fragments on chromosome 6 are from the same accession as the introgressions fragments on chromosome 7. However, one can also combine introgression fragments from different accessions, e.g. those on chromosome 6 may be from one accession and those on chromosome 7 may be from another accession. E.g. markers VSP1 and VSP2 are from one accession, while markers VSP3 and VSP4 are from a different accession. In one aspect the introgression fragment on chromosome 6 comprises the VSP1 marker and the introgession fragment on chromosome 7 comprises the VSP2 marker. In another aspect the introgression fragment on chromosome 6 comprises the VSP3 marker and the introgression fragment on chromosome 7 comprises the VSP4 marker. But the introgression fragment on chromosome 6 and 7 may also be from different accessions, so e.g. that on chromosome 6 may comprises VSP1, while that on chromosome 7 may comprise VSP4, or the fragment on chromosome 6 may comprise the VSP3 marker and that on chromosome 7 the VSP2 marker. Likewise, a plant homozygous for an introgression fragment, e.g. comprising QTL6.1, may contain the same fragment in homozygous form, but may also contain two different introgression fragments.

Although the present sources of the three QTLs are specific wild sources, there are likely other wild lettuce accessions (especially *L. virosa* accessions) which comprise QTL6.1 and/or QTL7.1 and/or QTL7.2 at the same locus/loci on chromosome 6 and/or 7. Such loci may comprise Nr:1 alleles which have slightly different nucleotide sequences, i.e. variants of the alleles (QTLs) found herein. Such variant QTLs can also be identified and introgressed into cultivated lettuce as described herein, to generate a cultivated lettuce plant comprising a genome of cultivated *L. sativa* and a recombinant chromosome 6 and/or 7, whereby the recombinant chromosome 6 and/or 7 comprises a wild *Lactuca* species introgression fragment (especially *L. virosa*), which confers Nr: 1 resistance onto the cultivated lettuce plant when present in homozygous or heterozygous form.

To identify such wild lettuce plants comprising QTL6.1 and/or QTL7.1 and/or QTL7.2 (or variant QTLs), wild accessions can be screened, e.g. in a marker assay or by sequence comparison or other methods, for the presence of one or more of the SNP markers provided herein. The putative Nr:1 resistance conferring QTLs (or variant QTLs) can then be introgressed into cultivated lettuce, e.g. optionally using MAS (marker assisted selection), i.e. using one or more (or all) of the SNP markers provided herein (or markers in between these) to detect and/or select progeny plants (e.g. backcross plants) comprising a recombinant chromosome 6 and/or 7. The selected plants, i.e. the cultivated lettuce plants comprising an introgression fragment on chromosome 6 and/or 7 wherein the introgression fragment on chromosome 6 is detectable by one or more of the SNP markers SNP_01 to SNP_07 or alternatively one or more of SNP markers SNP1.23, SNP_02, SNP2.24 or SNP_03, or markers in between any of these, (as described elsewhere herein), and/or wherein the introgression fragment on chromosome 7 is detectable by one or more of the SNP markers SNP_08 to SNP_14, or markers in between these, (as described elsewhere herein) detecting QTL7.2 or a variant thereof and/or one or more of the SNP markers SNP_15 to SNP_22 or alternatively SNP_17, SNP17.25, SNP_18 or SNP_19, or markers in between any of these, (as described elsewhere herein) detecting QTL7.1 or a variant thereof, can then be phenotyped for Nr:1 resistance together with the suitable control plants, preferably at least the genetic control and/or a Nr:1 susceptible plant such as Mafalda, in order to determine whether the introgression fragment indeed confers Nr:1 resistance. One or more Nr:1 resistance assays as described can be used.

Accessions of wild lettuce, such as *L. virosa*, are obtainable from the USDA National Plant Germplasm System collection or other seed collections, such as the CGN in Wageningen, and can thus be screened for the presence of QTL6.1 (or a variant) and/or QTL7.1 (or a variant) and/or QTL7.2 (or a variant) using e.g. a marker assay as described herein, and accessions comprising one or more of the SNP markers indicative of QTL 6.1 or a variant; and/or comprising one or more of the SNP markers indicative of QTL7.2 or variant; and/or comprising one or more of the SNP markers indicative of QTL7.1 or variant can be crossed with a cultivated lettuce plant having normal wild-type, non-recombinant chromosomes 6 and 7. The F2 generation (or further generation, such as the F3 or preferably a backcross generation such as the BC1, BC2, BC3 or BC1S1, etc.) can then be screened for recombinant plants having the introgression fragment or a resistance-conferring part thereof, using the molecular marker assays described herein. Alternatively, wild accessions can be screened phenotypically using a Nr:1 resistance assay and only progeny plants obtained from crosses with such wild accessions may be screened for the presence of the markers (and introgression fragments). Such progeny plants also fall within the scope of the invention.

In a specific embodiment, the introgression fragment comprising the Nr:1 resistance conferring QTL6.1 and/or the Nr:1 resistance conferring QTL7.1 and/or Nr:1 resistance conferring QTL7.2 is derivable from (or derived from) or obtainable from (or obtained from; or as present in) seeds, a representative sample of which has been deposited under accession number NCIMB42086, or from progeny thereof. The progeny may be any progeny which retain the one or more (or all) SNP markers indicative of the QTLs, as described. Thus, progeny are not limited to F1 or F2 progeny of the deposit, but can be any progeny, whether obtained by selfing and/or by crossing with another lettuce plant.

In one embodiment the introgression fragment is identifiable by one or more of the markers described elsewhere herein, especially markers SNP_01 to SNP_07 (or any marker in between these) for the introgression fragment on chromosome 6 (QTL6.1 or variant) or alternatively SNP1.23, SNP_02, SNP2.24 and/or SNP_03 (or any marker in between these), optionally also VSP1 or VSP3; and SNP_08 to SNP_14 (or any marker in between these) for the introgression fragment on chromosome 7 referred to as QTL7.2 (or variant) and SNP_15 to SNP_22 (or any marker in between these) or alternatively SNP_17, SNP17.25, SNP_18 and/or SNP_19 (or any marker in between these), optionally VSP2 or VSP4, for the introgression fragment on chromosome 7 referred to as QTL7.1 (or variant).

In one aspect the invention provides a cultivated lettuce plant line or variety, having a genome of *L. sativa* which line or variety comprises Nr:1 resistance, wherein the Nr:1 resistance is conferred by an introgression fragment on the cultivated lettuce chromosome 6 and/or chromosome 7, wherein said introgression fragment is obtained by (or obtainable by) crossing a Nr: 1 resistant *L. virosa* plant (which comprises one or more of the markers disclosed herein linked to the QTLs) with a cultivated lettuce plant.

In a further aspect the invention provides a cultivated lettuce plant line or variety, having a genome of *L. sativa* which line or variety comprises Nr:1 resistance, wherein the Nr:1 resistance is conferred by an introgression fragment on the cultivated lettuce chromosome 6 and/or chromosome 7, wherein said introgression fragment is obtained by (or obtainable by) crossing a plant grown from seeds deposited under NCIMB 42086 or progeny of this plant (which comprises one or more the markers disclosed herein linked to the QTLs) with a cultivated lettuce plant.

In yet another embodiment the invention relates to a plant of the invention i.e. a cultivated *L. sativa* plant comprising an introgression fragment from a wild lettuce on chromosome 6 and/or 7 in homozygous or heterozygous form and wherein said introgression fragment is a variant of the genomic sequence comprising the QTL(s) as found in seeds deposited under number NCIMB 42086, i.e. it comprises the Nr:1 QTL(s), but the genomic sequence may be different. As wild accessions will be genetically divergent, the genomic sequence of an introgression fragment comprising QTL6.1 or QTL7.1 or QTL7.2 (these QTLs are herein also referred to as variants or orthologs of QTL6.1, QTL7.1 and QTL7.2) from other wild lettuce accessions (e.g. other *L. virosa* accessions than the one deposited under accession number NCIMB42086) will most likely not be identical to the genomic sequence, and even the Nr: 1 resistance conferring gene (comprising a promoter, introns and exons) may be divergent in nucleotide sequence, but the function can be the same, i.e. conferring Nr: 1 resistance. The divergence can be seen in that certain SNP markers linked to (variant) QTL6.1 and/or (variant) QTL7.1 and/or (variant) QTL7.2 may be commonly found in various accessions, while other SNP markers may only be found in specific accessions. So for example not all of SNP_01 to SNP_7, or not all of SNP1.23, SNP_02, SNP2.24 or SNP_03, and/or SNP_08 to SNP_14 and/or SNP_15 to SNP_22, or SNP_17, SNP17.25, SNP_18 or SNP_19, may be found in other Nr:1 resistant wild lettuces (e.g. *L. virosa* accessions), while these accessions may still comprise QTL variants in the same region. Likewise, the genomic sequence comprising each of the SNP markers may not be 100% identical to the sequence provided herein, but may only have a sequence identity of (at least) 85%, 900, 95%, 98%, or 99%/0 to sequence provided herein, i.e. to any one of SEQ ID NO: 1 to SEQ ID NO: 22 and SEQ ID NO: 23 to 29. However, the Nr: 1 resistance conferring QTL6.1 (or variant) and QTL7.1 (or variant) and QTL7.2 (or variant, comprising e.g. a variant or ortholog of the Nr:1 allele) may still be present in such wild accessions. The skilled person is capable of identifying and introgressing the (variant) QTLs 6.1 and/or (variant) QTL 7.1 and/or (variant) QTL7.2 comprising region found in other wild lettuce accessions (especially *L. virosa* accessions; in particular *L. virosa* accessions comprising both free-choice and non-choice resistance against Nr: 1) into cultivated lettuce without undue burden.

In one embodiment the presence of the introgression fragment, or the chromosome 6 region (or variant or orthologous chromosome 6 region), comprising QTL6.1 (or variant), is detectable by a molecular marker assay which detects at least 1, preferably at least 2, 3, 4, 5, 6, or more (or all 7) Single Nucleotide Polymorphism (SNP) markers selected from the group consisting of:

a) the AA or AT genotype for the Single Nucleotide Polymorphism marker SNP_01 in SEQ ID NO: 1 (or in a sequence comprising substantial sequence identity to SEQ ID NO:1);

b) the CC or CT genotype for the Single Nucleotide Polymorphism marker SNP_02 in SEQ ID NO: 2 (or in a sequence comprising substantial sequence identity to SEQ ID NO:2);

c) the AA or AC genotype for the Single Nucleotide Polymorphism marker SNP_03 in SEQ ID NO: 3 (or in a sequence comprising substantial sequence identity to SEQ ID NO:3);

d) the GG or GA genotype for the Single Nucleotide Polymorphism marker SNP_04 in SEQ ID NO: 4 (or in a sequence comprising substantial sequence identity to SEQ ID NO:4);

e) the TT or TC genotype for the Single Nucleotide Polymorphism marker SNP_05 in SEQ ID NO: 5 (or in a sequence comprising substantial sequence identity to SEQ ID NO:5);

f) the CC or CA genotype for the Single Nucleotide Polymorphism marker SNP_06 in SEQ ID NO: 6 (or in a sequence comprising substantial sequence identity to SEQ ID NO:6);

g) the GG or GT genotype for the Single Nucleotide Polymorphism marker SNP_07 in SEQ ID NO: 7 (or in a sequence comprising substantial sequence identity to SEQ ID NO:7);

h) any wild lettuce genome-specific marker, such as a *L. virosa* genome specific marker, in between marker SNP_01 and SNP_07.

Thus, in one embodiment the plants according to the invention comprise at least a Adenine (A) (i.e. the AA or AT genotype) instead of two Thymines (TI) at nucleotide 71 of SEQ ID NO: 1 (referred to as SNP_01) or at the equivalent nucleotide of a genomic sequence comprising substantial sequence identity to SEQ ID NO: 1; and/or at least a Cytosine (C) (i.e. the CC or CT genotype) instead of two Thymines (TT) at nucleotide 71 of SEQ ID NO: 2 (referred to as SNP_02) or at the equivalent nucleotide of a genomic sequence comprising substantial sequence identity to SEQ ID NO:2; and/or at least a Adenine (A) (i.e. the AA or AC genotype) instead of two Cytosines (CC) at nucleotide 71 of SEQ ID NO: 3 (referred to as SNP_03) or at the equivalent nucleotide of a genomic sequence comprising substantial sequence identity to SEQ ID NO:3; and/or at least a Guanine (G) (i.e. the GG or GA genotype) instead of two Adenines (AA) at nucleotide 71 of SEQ ID NO: 4 (referred to as SNP_04) or at the equivalent nucleotide of a genomic sequence comprising substantial sequence identity to SEQ ID NO:4; and/or at least a Thymine (T) (i.e. the TT or TC genotype) instead of two Cytosines (CC) at nucleotide 71 of SEQ ID NO: 5 (referred to as SNP_05) or at the equivalent nucleotide of a genomic sequence comprising substantial sequence identity to SEQ ID NO:5; and/or at least a Cytosine (C) (i.e. the CC or CA genotype) instead of two Adenines (AA) at nucleotide 71 of SEQ ID NO: 6 (referred to as SNP_06) or at the equivalent nucleotide of a genomic sequence comprising substantial sequence identity to SEQ ID NO:6; and/or at least a Guanine (G) (i.e. the GG or GT genotype) instead of two Thymines (TI) at nucleotide 71 of SEQ ID NO: 7 (referred to as SNP_07) or at the equivalent nucleotide of a genomic sequence comprising substantial sequence identity to SEQ ID NO:7.

In another embodiment the presence of the introgression fragment, or the chromosome 6 region (or variant or orthologous chromosome 6 region), comprising QTL6.1 (or variant), is detectable by a molecular marker assay which detects at least 1, preferably at least 2, 3 or 4 of the Single Nucleotide Polymorphism (SNP) markers selected from the group consisting of:

a) The CC or CT genotype for the Single Nucleotide Polymorphism marker SNP1.23 in SEQ ID NO: 23 or in a sequence comprising substantial sequence identity to SEQ ID NO: 23;
b) the CC or CT genotype for the Single Nucleotide Polymorphism marker SNP_02 in SEQ ID NO: 2 or in a sequence comprising substantial sequence identity to SEQ ID NO: 2;
c) the TT or CT genotype for the Single Nucleotide Polymorphism marker SNP2.24 in SEQ ID NO: 24 or in a sequence comprising substantial sequence identity to SEQ ID NO: 24;
d) the AA or AC genotype for the Single Nucleotide Polymorphism marker SNP_03 in SEQ ID NO: 3 or in a sequence comprising substantial sequence identity to SEQ ID NO: 3;
e) any a L. virosa genome specific marker, in between marker SNP1.23 and SNP_03.

Thus, in one embodiment the plants according to the invention comprise at least a Cytosine (C) (i.e. the CC or CT genotype) instead of two Thymines (TT) at nucleotide 71 of SEQ ID NO: 23 (referred to as SNP1.23) or at the equivalent nucleotide of a genomic sequence comprising substantial sequence identity to SEQ ID NO:23; and/or at least a Cytosine (C) (i.e. the CC or CT genotype) instead of two Thymines (TI) at nucleotide 71 of SEQ ID NO: 2 (referred to as SNP_02) or at the equivalent nucleotide of a genomic sequence comprising substantial sequence identity to SEQ ID NO:2; and/or at least a Thymine (T) (i.e. the TT or CT genotype) instead of two Cytosines (CC) at nucleotide 71 of SEQ ID NO: 24 (referred to as SNP2.24) or at the equivalent nucleotide of a genomic sequence comprising substantial sequence identity to SEQ ID NO:24; and/or at least a Adenine (A) (i.e. the AA or AC genotype) instead of two Cytosines (CC) at nucleotide 71 of SEQ ID NO: 3 (referred to as SNP_03) or at the equivalent nucleotide of a genomic sequence comprising substantial sequence identity to SEQ ID NO:3.

In one embodiment the presence of the introgression fragment, or the chromosome 7 region (or variant or orthologous chromosome 7 region), comprising QTL7.2 (or variant), is detectable by a molecular marker assay which detects at least 1, preferably at least 2, 3, 4, 5, 6, or more (or all 7) Single Nucleotide Polymorphism (SNP) markers selected from the group consisting of:
  a) the TT or TC genotype for the Single Nucleotide Polymorphism marker SNP_08 in SEQ ID NO: 8 (or in a sequence comprising substantial sequence identity to SEQ ID NO:8);
  b) the CC or CT genotype for the Single Nucleotide Polymorphism marker SNP_09 in SEQ ID NO: 9 (or in a sequence comprising substantial sequence identity to SEQ ID NO:9);
  c) the AA or AG genotype for the Single Nucleotide Polymorphism marker SNP_10 in SEQ ID NO: 10 (or in a sequence comprising substantial sequence identity to SEQ ID NO:10);
  d) the CC or CA genotype for the Single Nucleotide Polymorphism marker SNP_11 in SEQ ID NO: 11 (or in a sequence comprising substantial sequence identity to SEQ ID NO: 11);
  e) the CC or CT genotype for the Single Nucleotide Polymorphism marker SNP_12 in SEQ ID NO: 12 (or in a sequence comprising substantial sequence identity to SEQ ID NO: 12);
  f) the GG or GA genotype for the Single Nucleotide Polymorphism marker SNP_13 in SEQ ID NO: 13 (or in a sequence comprising substantial sequence identity to SEQ ID NO:13);
  g) the CC or CT genotype for the Single Nucleotide Polymorphism marker SNP_14 in SEQ ID NO: 14 (or in a sequence comprising substantial sequence identity to SEQ ID NO:14);
  h) any wild lettuce genome-specific marker, such as a L. virosa genome specific marker, in between marker SNP_08 and SNP_14.

Thus, in one embodiment the plants according to the invention comprise at least a Thymine (T) (i.e. the TT or TC genotype) instead of two Cytosines (CC) at nucleotide 71 of SEQ ID NO: 8 (referred to as SNP_08) or at the equivalent nucleotide of a genomic sequence comprising substantial sequence identity to SEQ ID NO:8; and/or at least a Cytosine (C) (i.e. the CC or CT genotype) instead of two Thymines (TT) at nucleotide 71 of SEQ ID NO: 9 (referred to as SNP_09) or at the equivalent nucleotide of a genomic sequence comprising substantial sequence identity to SEQ ID NO:9; and/or at least a Adenine (A) (i.e. the AA or AG genotype) instead of two Guanines (GG) at nucleotide 71 of SEQ ID NO: 10 (referred to as SNP_10) or at the equivalent nucleotide of a genomic sequence comprising substantial sequence identity to SEQ ID NO:10; and/or at least a Cytosine (C) (i.e. the CC or CA genotype) instead of two Adenines (AA) at nucleotide 71 of SEQ ID NO: 11 (referred to as SNP_11) or at the equivalent nucleotide of a genomic sequence comprising substantial sequence identity to SEQ ID NO: 11; and/or at least a Cytosine (C) (i.e. the CC or CT genotype) instead of two Thymines (TT) at nucleotide 71 of SEQ ID NO: 12 (referred to as SNP_12) or at the equivalent nucleotide of a genomic sequence comprising substantial sequence identity to SEQ ID NO:12; and/or at least a Guanine (G) (i.e. the GG or GA genotype) instead of two Adenines (AA) at nucleotide 136 of SEQ ID NO: 13 (referred to as SNP_13) or at the equivalent nucleotide of a genomic sequence comprising substantial sequence identity to SEQ ID NO: 13; and/or at least a Cytosine (C) (i.e. the CC or CT genotype) instead of two Thymines (T) at nucleotide 71 of SEQ ID NO: 14 (referred to as SNP_14) or at the equivalent nucleotide of a genomic sequence comprising substantial sequence identity to SEQ ID NO: 14.

In one embodiment the presence of the introgression fragment, or the chromosome 7 region (or variant or orthologous chromosome 7 region), comprising QTL7.1 (or variant), is detectable by a molecular marker assay which detects at least 1, preferably at least 2, 3, 4, 5, 6, 7 or more (or all 8) Single Nucleotide Polymorphism (SNP) markers selected from the group consisting of:
  a) the TT or TA genotype for the Single Nucleotide Polymorphism marker SNP_15 in SEQ ID NO: 15 (or in a sequence comprising substantial sequence identity to SEQ ID NO:15);
  b) the GG or GA genotype for the Single Nucleotide Polymorphism marker SNP_16 in SEQ ID NO: 16 (or in a sequence comprising substantial sequence identity to SEQ ID NO:16);
  c) the TT or TC genotype for the Single Nucleotide Polymorphism marker SNP_17 in SEQ ID NO: 17 (or in a sequence comprising substantial sequence identity to SEQ ID NO:17);
  d) the GG or GC genotype for the Single Nucleotide Polymorphism marker SNP_18 in SEQ ID NO: 18 (or in a sequence comprising substantial sequence identity to SEQ ID NO:18);

e) the GG or GA genotype for the Single Nucleotide Polymorphism marker SNP_19 in SEQ ID NO: 19 (or in a sequence comprising substantial sequence identity to SEQ ID NO:19);

f) the TT or TC genotype for the Single Nucleotide Polymorphism marker SNP_20 in SEQ ID NO: 20 (or in a sequence comprising substantial sequence identity to SEQ ID NO:20);

g) the CC or CA genotype for the Single Nucleotide Polymorphism marker SNP_21 in SEQ ID NO: 21 (or in a sequence comprising substantial sequence identity to SEQ ID NO:21);

h) the CC or CT genotype for the Single Nucleotide Polymorphism marker SNP_22 in SEQ ID NO: 22 (or in a sequence comprising substantial sequence identity to SEQ ID NO:22);

i) any wild lettuce genome-specific marker, such as a *L. virosa* genome specific marker, in between marker SNP_15 and SNP_22.

Thus, in one embodiment the plants according to the invention comprise at least a Thymine (T) (i.e. the TT or TA genotype) instead of two Adenines (CC) at nucleotide 71 of SEQ ID NO: 15 (referred to as SNP_15) or at the equivalent nucleotide of a genomic sequence comprising substantial sequence identity to SEQ ID NO:15; and/or at least a Guanine (G) (i.e. the GG or GA genotype) instead of two Adenines (AA) at nucleotide 71 of SEQ ID NO: 16 (referred to as SNP_16) or at the equivalent nucleotide of a genomic sequence comprising substantial sequence identity to SEQ ID NO:16; and/or at least a Thymine (T) (i.e. the TT or TC genotype) instead of two Cytosines (CC) at nucleotide 71 of SEQ ID NO: 17 (referred to as SNP_17) or at the equivalent nucleotide of a genomic sequence comprising substantial sequence identity to SEQ ID NO: 17; and/or at least a Guanine (G) (i.e. the GG or GC genotype) instead of two Cytosines (CC) at nucleotide 71 of SEQ ID NO: 18 (referred to as SNP_18) or at the equivalent nucleotide of a genomic sequence comprising substantial sequence identity to SEQ ID NO: 18; and/or at least a Guanine (G) (i.e. the GG or GA genotype) instead of two Adenines (AA) at nucleotide 71 of SEQ ID NO: 19 (referred to as SNP_19) or at the equivalent nucleotide of a genomic sequence comprising substantial sequence identity to SEQ ID NO:19; and/or at least a Thymine (T) (i.e. the TT or TC genotype) instead of two Cytosines (CC) at nucleotide 72 of SEQ ID NO: 20 (referred to as SNP_20) or at the equivalent nucleotide of a genomic sequence comprising substantial sequence identity to SEQ ID NO:20; and/or at least a Cytosine (C) (i.e. the CC or CA genotype) instead of two Adenines (AA) at nucleotide 41 of SEQ ID NO: 21 (referred to as SNP_21) or at the equivalent nucleotide of a genomic sequence comprising substantial sequence identity to SEQ ID NO:21; and/or at least a Cytosine (C) (i.e. the CC or CT genotype) instead of two Thymines (TT) at nucleotide 71 of SEQ ID NO: 22 (referred to as SNP_22) or at the equivalent nucleotide of a genomic sequence comprising substantial sequence identity to SEQ ID NO:22.

In a further embodiment the presence of the introgression fragment, or the chromosome 7 region (or variant or orthologous chromosome 7 region), comprising QTL7.1 (or variant), is detectable by a molecular marker assay which detects at least 1, preferably at least 2, 3, 4 of the Single Nucleotide Polymorphism (SNP) markers selected from the group consisting of:

a) the TT or TC genotype for the Single Nucleotide Polymorphism marker SNP_17 in SEQ ID NO: 17 (or in a sequence comprising substantial sequence identity to SEQ ID NO: 17);

b) the TT or TC genotype for the Single Nucleotide Polymorphism marker SNP17.25 in SEQ ID NO: 25 (or in a sequence comprising substantial sequence identity to SEQ ID NO: 25);

c) the GG or GC genotype for the Single Nucleotide Polymorphism marker SNP_18 in SEQ ID NO: 18 (or in a sequence comprising substantial sequence identity to SEQ ID NO: 18);

d) the GG or GA genotype for the Single Nucleotide Polymorphism marker SNP_19 in SEQ ID NO: 19 (or in a sequence comprising substantial sequence identity to SEQ ID NO: 19);

e) any wild lettuce genome specific marker, especially *L. virosa*-genome specific marker, located physically in-between SNP_17 and SNP_19.

Thus, in one embodiment the plants according to the invention comprise at least a Thymine (T) (i.e. the TT or TC genotype) instead of two Cytosines (CC) at nucleotide 71 of SEQ ID NO: 17 (referred to as SNP_17) or at the equivalent nucleotide of a genomic sequence comprising substantial sequence identity to SEQ ID NO:17; at least a Thymine (T) (i.e. the TT or TC genotype) instead of two Cytosines (CC) at nucleotide 71 of SEQ ID NO: 25 (referred to as SNP17.25) or at the equivalent nucleotide of a genomic sequence comprising substantial sequence identity to SEQ ID NO:25; and/or at least a Guanine (G) (i.e. the GG or GC genotype) instead of two Cytosines (CC) at nucleotide 71 of SEQ ID NO: 18 (referred to as SNP_18) or at the equivalent nucleotide of a genomic sequence comprising substantial sequence identity to SEQ ID NO:18; and/or at least a Guanine (G) (i.e. the GG or GA genotype) instead of two Adenines (AA) at nucleotide 71 of SEQ ID NO: 19 (referred to as SNP_19) or at the equivalent nucleotide of a genomic sequence comprising substantial sequence identity to SEQ ID NO:19.

The SNP genotype refers to two nucleotides, and genomic sequences comprising one of these two nucleotides, one on each chromosome 6 (for SNP_01 to SNP_07 or for SNP1.23, SNP_02, SNP2.24 or SNP_03) or 7 (for SNP_08 to SNP_14 and SNP_15 to SNP_22 or for SNP_17, SNP17.25, SNP_18 or SNP_19). So a plant having a CC genotype for SNP_22 has an identical nucleotide (C) on both chromosomes, while a plant having an CT genotype for SNP_22 has one chromosome with an C at nucleotide 71 of SEQ ID NO: 22 (or at the equivalent nucleotide of a genomic sequence comprising substantial sequence identity to SEQ ID NO:22) and one chromosome with a T at nucleotide 71 of SEQ ID NO: 22 (or at the equivalent nucleotide of a genomic sequence comprising substantial sequence identity to SEQ ID NO:22). As the genomic sequences around the SNP markers provided herein may vary slightly in introgression fragments from other wild lettuce accessions (i.e. variants or orthologous chromosome 6 or 7 regions) it is clear that the nucleotide sequences before and after the SNP may not be 100% identical to the sequences provided herein. Therefore sequences having substantial sequence identity to the sequences provided herein, but which comprise the same SNP, are encompassed herein. It is also clear that in certain aspects the introgression is in homozygous form, and the SNP marker genotype is then the genotype homozygous for the QTL.

The introgression fragment may be large, even half of a chromosome, or small, as long as the Nr: 1 resistance conferring part is retained. In one aspect the introgression fragment on chromosome 6 and/or 7 is equal to or less than 120 Mb, 100 Mb, 84 Mb, 80 Mb, 75 Mb, 74 Mb, 73 Mb, 60 Mb, 50 Mb, 40 Mb, 30 Mb, 20 Mb, 16 Mb, 15 Mb, 10 Mb in size, preferably equal to or less than 8 Mb in size, more preferably equal to or less than 6, 5, 4, 3 or 2.5 Mb in size, e.g. equal to or less than 2 Mb. In one aspect the introgression fragment is at least 0.2 Mb, 0.5 Mb, 1.0 Mb, 1.5 Mb, 1.9 Mb, 2.0 Mb, 2.5 Mb or 3 Mb in size. Thus, various ranges of introgression sizes are encompassed herein. The size can be easily determined by e.g. whole genome sequencing or Next Generation Sequencing, e.g. as described in Qi et al. 2013 (Nature Genetics December 2013, Vol 45, No. 12, pages 1510-1518) or in Huang et al. 2009 (Nature Genetics, Volume 41, Number 12, p 1275-1283). Especially introgression regions can be easily distinguished from cultivated genomic regions due to the larger amount of genetic variation (SNPs, INDELs, etc.) in the introgression region.

The skilled person knows how to screen and identify wild lettuce, e.g. L. virosa, for the presence of any one of the QTLs or orthologs or variants as described herein. E.g. various L. virosa accessions can first be selected phenotypically by assaying their Nr:1 resistance, especially free-choice and/or non-choice resistance and in one aspect select those accessions which comprise both free-choice and non-choice resistance. Alternatively, various L. virosa accessions may be screened directly for the presence of one or more of the SNP markers (or markers in between the SNP markers) described herein. Once a candidate wild lettuce, e.g. L. virosa, has been identified, the skilled person knows how to transfer one, two or all three of the QTLs of the invention from the wild lettuce into cultivated lettuce using traditional breeding techniques. For example, plants grown from the wild accessions, such as plants grown from deposited seeds (NCIMB42086), can be crossed with a cultivated lettuce plant to obtain F1 seeds. The F1 plants can be selfed one or more times to produce F2 or F3 plants (or further selfing generations), and/or F1, F2 plants or F3 plants, etc., can be backcrossed to a cultivated lettuce parent. Progeny plants which comprise the QTL6.1 (or variant) and/or QTL7.1 (or variant) and/or QTL7.2 (or variant) can be screened for, and selected for, by the presence of one or more or all of the above SNP markers (or markers in between any of those markers) in order to identify plants comprising a recombinant chromosome 6 and/or 7, comprising the QTL(s). Techniques such as embryo rescue may need to used to obtain progeny from interspecific crosses (e.g. between L. sativa and L. virosa).

In yet another embodiment of the invention the presence of the introgression fragment in a cultivated lettuce plant, or the chromosome 6 region (or orthologous chromosome 6 region), comprising QTL6.1 (or variant), is detectable by a molecular marker assay which detects at least one of the markers selected from the group consisting of:
 a) the AA or AT genotype for the Single Nucleotide Polymorphism marker SNP_01 in SEQ ID NO: 1 (or in a sequence comprising substantial sequence identity to SEQ ID NO: 1);
 b) the GG or GT genotype for the Single Nucleotide Polymorphism marker SNP_07 in SEQ ID NO: 7 (or in a sequence comprising substantial sequence identity to SEQ ID NO:7);
 c) any wild lettuce genome-specific marker in between marker SNP_01 and SNP_07;
 d) any wild lettuce genome-specific marker which is genetically linked within 7 cM, 5 cM, 3 cM or less of any one of markers SNP_01 to SNP_07; and
 e) any wild lettuce genome-specific marker which is physically linked within 5 Mb, 3 Mb, 2 Mb, 1 Mb, 0.5 Mb or 0.2 Mb or less of any one of markers SNP_01 to SNP_07.

In one aspect the markers of c) are one or more of SNP_02 to SNP_06.

In one aspect, at least one, two, at least three, at least four or more markers are detected from the markers of a), b) and/or c) above. In another aspect, at least one, two, at least three, at least four or more markers are detected from the markers of a), b), c), d) and/or e) above. In one embodiment at least the marker of a) and/or b) is detected and optionally at least one, two, three or more markers of c), d) and/or e) are detected. In one aspect at least 1, 2, or 3 markers of c) are detected, especially at least SNP_04, SNP_05 and/or SNP_06.

Any wild lettuce genome-specific marker (e.g. L. virosa genome specific) in-between the marker of a) and b) refers to any molecular marker which maps genetically to the chromosome 6 region in-between marker SNP_01 and SNP_07 and/or which lies physically in-between marker SNP_01 and SNP_07, and which is indicative of the wild lettuce chromosome 6 region. This means that the marker is polymorphic between the cultivated lettuce genome and the wild lettuce genome. In one aspect, the marker is a Single Nucleotide Polymorphism (SNP), but other molecular markers such as RFLP, AFLP, RAPD, DNA sequencing, etc. may equally be used.

In an alternative embodiment of the invention the presence of the introgression fragment in a cultivated lettuce plant, or the chromosome 6 region (or orthologous chromosome 6 region), comprising QTL6.1 (or variant), is detectable by a molecular marker assay which detects at least one of the markers selected from the group consisting of:
 a) the CC or CT genotype for the Single Nucleotide Polymorphism marker SNP1.23 in SEQ ID NO: 23 (or in a sequence comprising substantial sequence identity to SEQ ID NO:23);
 b) the AA or AC genotype for the Single Nucleotide Polymorphism marker SNP_03 in SEQ ID NO: 3 or in a sequence comprising substantial sequence identity to SEQ ID NO: 3;
 c) any L. virosa genome specific marker, physically located in between marker SNP1.23 and SNP_03.
 d) any L. virosa genome specific marker which is physically linked within 10 Mb, 5 Mb, 3 Mb, 2 Mb, 1 Mb, 0.5 Mb or 0.2 Mb or less of any one of markers SNP1.23 to SNP_03.

In one aspect the markers of c) are one or more of SNP_02, SNP2.24, optionally VSP1 and/or VSP3.

In one aspect, at least one, two, at least three, at least four or more markers are detected from the markers of a), b) and/or c) above. In another aspect, at least one, two, at least three, at least four or more markers are detected from the markers of a), b), c), and/or d) above. In one embodiment at least the marker of a) and/or b) is detected and optionally at least one, two, three or more markers of c) and/or d) are detected. In one aspect at least 1, 2, or 3 markers of c) are detected, especially at least SNP_02 and/or SNP2.24.

Any L. virosa genome specific marker means that the marker is indicative of the introgression fragment and the presence of the L. virosa genome, i.e. the marker is polymorphic between the cultivated lettuce genome and the wild L. virosa lettuce genome. In one aspect, the marker is a Single Nucleotide Polymorphism (SNP), but other molecular markers such as RFLP, AFLP, RAPD, DNA sequencing, etc. may equally be used.

Likewise in one embodiment of the invention the presence of the introgression fragment in a cultivated lettuce plant, or the chromosome 7 region (or orthologous chromosome 7 region), comprising QTL7.2 (or variant), is detectable by a molecular marker assay which detects at least one of the markers selected from the group consisting of:
a) the TT or TC genotype for the Single Nucleotide Polymorphism marker SNP_08 in SEQ ID NO: 8 (or in a sequence comprising substantial sequence identity to SEQ ID NO:8);
b) the CC or CT genotype for the Single Nucleotide Polymorphism marker SNP_14 in SEQ ID NO: 14 (or in a sequence comprising substantial sequence identity to SEQ ID NO:8);
c) any wild lettuce genome-specific marker in between marker SNP_08 and SNP_14;
d) any wild lettuce genome-specific marker which is genetically linked within 7 cM, 5 cM, 3 cM or less of any one of markers SNP_08 to SNP_14; and
e) any wild lettuce genome-specific marker which is physically linked within 5 Mb, 3 Mb, 2 Mb, 1 Mb, 0.5 Mb or 0.2 Mb or less of any one of markers SNP_08 to SNP_14.

In one aspect the markers of c) are one or more of SNP_09 to SNP_13.

In one aspect, at least one, two, at least three, at least four or more markers are detected from the markers of a), b) and/or c) above. In another aspect, at least one, two, at least three, at least four or more markers are detected from the markers of a), b), c), d) and/or e) above. In one embodiment at least the marker of a) and/or b) is detected and optionally at least one, two, three or more markers of c), d) and/or e) are detected. In one aspect at least 1, 2 or 3 markers of c) are detected, especially SNP_09, SNP_10 and/or SNP_11.

Any wild lettuce genome-specific marker (e.g. *L. virosa* genome specific) in-between the marker of a) and b) refers to any molecular marker which maps genetically to the chromosome 6 region in-between marker SNP_08 and SNP_14 and/or which lies physically in-between marker SNP_08 and SNP_14, and which is indicative of the wild lettuce chromosome 7 region. This means that the marker is polymorphic between the cultivated lettuce genome and the wild lettuce genome. In one aspect, the marker is a Single Nucleotide Polymorphism (SNP), but other molecular markers such as RFLP, AFLP, RAPD, DNA sequencing, etc. may equally be used.

Likewise in one embodiment of the invention the presence of the introgression fragment in a cultivated lettuce plant, or the chromosome 7 region (or orthologous chromosome 7 region), comprising QTL7.1 (or variant), is detectable by a molecular marker assay which detects at least one of the markers selected from the group consisting of:
a) the TT or TA genotype for the Single Nucleotide Polymorphism marker SNP_08 in SEQ ID NO: 15 (or in a sequence comprising substantial sequence identity to SEQ ID NO:15);
b) the CC or CT genotype for the Single Nucleotide Polymorphism marker SNP_14 in SEQ ID NO: 22 (or in a sequence comprising substantial sequence identity to SEQ ID NO:22);
c) any wild lettuce genome-specific marker in between marker SNP_15 and SNP_22;
d) any wild lettuce genome-specific marker which is genetically linked within 7 cM, 5 cM, 3 cM or less of any one of markers SNP_15 to SNP_22; and
e) any wild lettuce genome-specific marker which is physically linked within 5 Mb, 3 Mb, 2 Mb, 1 Mb, 0.5 Mb or 0.2 Mb or less of any one of markers SNP_15 to SNP_22.

In one aspect the markers of c) are one or more of SNP_16 to SNP_21.

In one aspect, at least one, two, at least three, at least four or more markers are detected from the markers of a), b) and/or c) above. In another aspect, at least one, two, at least three, at least four or more markers are detected from the markers of a), b), c), d) and/or e) above. In one embodiment at least the marker of a) and/or b) is detected and optionally at least one, two, three or more markers of c), d) and/or e) are detected. In one aspect at least 1, 2 or 3 markers of c) are detected, especially SNP_19, SNP_20 and/or SNP_21.

Any wild lettuce genome-specific marker (e.g. *L. virosa* genome specific) in-between the marker of a) and b) refers to any molecular marker which maps genetically to the chromosome 6 region in-between marker SNP_15 and SNP_22 and/or which lies physically in-between marker SNP_15 and SNP_22, and which is indicative of the wild lettuce chromosome 7 region. This means that the marker is polymorphic between the cultivated lettuce genome and the wild lettuce genome. In one aspect, the marker is a Single Nucleotide Polymorphism (SNP), but other molecular markers such as RFLP, AFLP, RAPD, DNA sequencing, etc. may equally be used.

In an alternative embodiment of the invention the presence of the introgression fragment in a cultivated lettuce plant, or the chromosome 7 region (or orthologous chromosome 7 region), comprising QTL7.1 (or variant), is detectable by a molecular marker assay which detects at least one of the markers selected from the group consisting of:
a) the TT or TC genotype for the Single Nucleotide Polymorphism marker SNP_17 in SEQ ID NO: 17 (or in a sequence comprising substantial sequence identity to SEQ ID NO: 17);
b) the GG or GA genotype for the Single Nucleotide Polymorphism marker SNP_19 in SEQ ID NO: 19 (or in a sequence comprising substantial sequence identity to SEQ ID NO: 19);
c) any a *L. virosa* genome specific marker, physically located in between marker SNP_17 and SNP_19.
d) any *L. virosa* genome specific marker which is physically linked within 12 Mb, 10 Mb, 5 Mb, 3 Mb, 2 Mb, 1 Mb, 0.5 Mb or 0.2 Mb or less of any one of markers SNP_17 to SNP_19.

In one aspect the markers of c) are one or more of SNP17.25, SNP_18, optionally VSP4.

In one aspect the marker of d) is VSP2 or SNP_16.

In one aspect, at least one, two, at least three, at least four or more markers are detected from the markers of a), b) and/or c) above. In another aspect, at least one, two, at least three, at least four or more markers are detected from the markers of a), b), c), and/or d) above. In one embodiment at least the marker of a) and/or b) is detected and optionally at least one, two, three or more markers of c) and/or d) are detected. In one aspect at least 1, 2, or 3 markers of c) are detected, especially at least SNP17.25 and/or SNP_18.

Any *L. virosa* genome specific marker means that the marker is indicative of the introgression fragment and the presence of the *L. virosa* genome, i.e. the marker is polymorphic between the cultivated lettuce genome and the wild *L. virosa* lettuce genome. In one aspect, the marker is a Single Nucleotide Polymorphism (SNP), but other molecular markers such as RFLP, AFLP, RAPD, DNA sequencing, etc. may equally be used.

Also provided are seeds from which a plant of the invention can be grown, as are lettuce leaves (or parts thereof) and heads harvested from a plant of the invention and comprising the recombinant chromosome 6 and/or 7 in their genome. Likewise a plant cell, tissue or plant part of a plant or of a seed is provided comprising at least one recombinant chromosome 6 and/or 7, wherein said recombinant chromosome 6 and/or 7 comprises an introgression fragment from a wild lettuce and wherein said introgression fragment comprises a QTL conferring Nr:1 resistance.

The molecular markers described herein may be detected according to standard method. For example SNP markers can easily be detected using a KASP-assay (see www.kpbioscience.co.uk) or other assays. For developing a KASP-assay, for example 70 base pairs upstream and 70 base pairs downstream of the SNP can be selected and two allele-specific forward primers and one allele specific reverse primer can be designed. See e.g. Allen et al. 2011, Plant Biotechnology J. 9, 1086-1099, especially p 097-1098 for KASP assay method.

Thus, in one aspect, the SNP markers and the presence/absence of the marker associated with the QTL(s) is determined using a KASP assay, but equally other assays can be used. For example, optionally DNA sequencing may also be used.

The physical size of an introgression fragment can be determined by various methods, such as physical mapping, sequencing or by visualization of the introgression using Fluorescent in situ hybridization (FISH) images (Verlaan et al. 2011, Plant Journal 68: 1093-1103).

Plants with various sizes introgression fragments on chromosome 6 and/or 7 can be generated by generating recombinant plants from a population of plants derived from a cross between a cultivated lettuce plant (lacking the introgressions) and a Nr:1 resistant *L. virosa* plant or between cultivated lettuce and a plant of the invention (a cultivated lettuce comprising a recombinant chromosome 6 and/or 7) and selecting progeny having different introgression sizes.

Methods

The markers and genomic regions identified herein can be used in various methods, and this applies to the first regions and markers identified (see e.g. FIG. 3A) as well as to the later regions and markers identified (see e.g. FIG. 3B), because the QTLs are the same. The invention provides a number of methods, namely:

1) a method for identifying wild lettuce plant, especially a *L. virosa* accession, comprising one or more of QTL6.1, QTL7.1 and/or QTL7.2 (or variants of any of these);

2) a method for transferring one or more of the QTLs selected from QTL6.1, QTL7.1 and/or QTL7.2 (or variants of any of these) from a wild lettuce plant (e.g. *L. virosa*) into cultivated lettuce (*L. sativa*) to generate a Nr: 1 resistant cultivated lettuce;

3) a method for screening cultivated lettuce lines or varieties for the presence of one or more of the QTLs selected from QTL6.1, QTL7.1 and/or QTL7.2 (or variants of any of these); and 4) a method for transferring one or more of the QTLs selected from QTL6.1, QTL7.1 and/or QTL7.2 (or variants of any of these) from a cultivated lettuce (*L. sativa*) into another cultivated lettuce, e.g. into a Nr: 1 susceptible lettuce plant line or variety;

5) a method for using seeds deposited under accession number NCIMB42086, or descendants thereof, for generating Nr:1 resistant cultivated lettuce;

6) a method for cultivating plants of the invention, i.e. Nr:1 resistant *L. sativa* plants comprising one or more of the QTLs selected from QTL6.1, QTL7.1 and/or QTL7.2 (or variants of any of these), in areas where *N. ribisnigri* biotype Nr: 1 is present.

Method for Identifying Wild Lettuce Comprising One or More of QTL6.1. QTL7.1 and/or QTL7.2 (or Variants of any of these)

In one aspect a method for identifying wild lettuce plants comprising one or more of QTL6.1, QTL7.1 and/or QTL7.2 (or variants thereof) is provided, comprising the steps of:

a) providing a wild lettuce plant or a plurality of wild lettuce plants;

b) optionally testing the wild lettuce plant or plurality of plants for Nr:1 resistance in an Nr:1 resistance assay;

c) screening the genomic DNA of the plant or plurality of plants of a), or optionally only of the Nr:1 resistant plant or plants identified in b), for the presence of one or more markers indicative of QTL6.1 or a variant thereof and/or indicative of QTL7.1 or a variant thereof and/or indicative of QTL7.2 or a variant thereof; and d) identifying a plant comprising one or more of said markers of c);

e) optionally testing the plant of d) for Nr:1 resistance in an Nr: 1 resistance assay;

f) optionally crossing the wild lettuce plant of d) with a cultivated lettuce plant.

Optionally the method further comprises introgressing the QTL6.1, QTL7.1 and/or QTL7.2 (or variants thereof) into cultivated lettuce, especially Nr:1 susceptible lettuce, and generating a *L. sativa* plant comprising Nr:1 resistance conferred by one or more of the introgression fragments. This can e.g. be done by backcrossing. Optionally marker assisted selection may be used.

The plant or plants in step a) are preferably *L. virosa*, e.g. originating from different geographic regions.

In step b) or e) a phenotypic Nr: resistance assay (e.g. field test or controlled environment test) can be carried out in order to select plants which are resistant against Nr:1 and therefore putatively comprise one or more of the QTLs. The Nr: 1 resistance assay may be a free choice and/or non-choice assay.

A Nr: 1 resistant *L. sativa* plant obtained by the method is also an embodiment of the invention.

The genomic DNA in step c) can be screened for the presence of one or more markers indicative of QTL6.1 or a variant thereof, as described further above, e.g. by determining the presence of one or more markers selected from the group consisting of:

a) the AA or AT genotype for the Single Nucleotide Polymorphism marker SNP_01 in SEQ ID NO: 1 or in a sequence comprising substantial sequence identity to SEQ ID NO: 1; and/or b) the CC or CT genotype for the Single Nucleotide Polymorphism marker SNP_02 in SEQ ID NO: 2 or in a sequence comprising substantial sequence identity to SEQ ID NO: 2; and/or c) the AA or AC genotype for the Single Nucleotide Polymorphism marker SNP_03 in SEQ ID NO: 3 or in a sequence comprising substantial sequence identity to SEQ ID NO: 3; and/or d) the GG or GA genotype for the Single Nucleotide Polymorphism marker SNP_04 in SEQ ID NO: 4 or in a sequence comprising substantial sequence identity to SEQ ID NO: 4; and/or
e) the TT or TC genotype for the Single Nucleotide Polymorphism marker SNP_05 in SEQ ID NO: 5 or in a sequence comprising substantial sequence identity to SEQ ID NO: 5; and/or
f) the CC or CA genotype for the Single Nucleotide Polymorphism marker SNP_06 in SEQ ID NO: 6 or in a sequence comprising substantial sequence identity to SEQ ID NO: 6; and/or
g) the GG or GT genotype for the Single Nucleotide Polymorphism marker SNP_07 in SEQ ID NO: 7 or in a sequence comprising substantial sequence identity to SEQ ID NO: 7; and/or
h) any wild lettuce genome specific marker, especially *L. virosa*-genome specific marker, located physically in-between SNP_01 and SNP_07, e.g. in between any two markers of SNP_01 to SNP_07.

Alternatively, the genomic DNA in step c) can be screened for the presence of one or more markers indicative of QTL6.1 or a variant thereof, as described further above, e.g. by determining the presence of one or more markers selected from the group consisting of:
a) The CC or CT genotype for the Single Nucleotide Polymorphism marker SNP1.23 in SEQ ID NO: 23 (or in a sequence comprising substantial sequence identity to SEQ ID NO: 23);
b) the CC or CT genotype for the Single Nucleotide Polymorphism marker SNP_02 in SEQ ID NO: 2 (or in a sequence comprising substantial sequence identity to SEQ ID NO: 2);
c) the TT or CT genotype for the Single Nucleotide Polymorphism marker SNP2.24 in SEQ ID NO: 24 (or in a sequence comprising substantial sequence identity to SEQ ID NO: 24);
   the AA or AC genotype for the Single Nucleotide Polymorphism marker SNP_03 in SEQ ID NO: 3 (or in a sequence comprising substantial sequence identity to SEQ ID NO: 3);
d) any wild lettuce genome specific marker, especially *L. virosa*-genome specific marker, located physically in-between SNP1.23 and SNP_03 (e.g. in-between SNP1.23 and SNP2.24, SNP1.23 and SNP_02); or in between SNP_02 and SNP_03 (e.g. in-between SNP_02 and SNP2.24); or in between SNP2.24 and SNP_03;
e) any wild lettuce genome specific marker especially *L. virosa*-genome specific marker, located within a distance of 10 Mb, preferably within 5 Mb, of any marker selected from SNP1.23, SNP_02, SNP2.24, or SNP_03.

Optionally also *L. virosa* specific markers (VSP1 or VSP3) can be screened to identify and/or distinguish accession types comprising the QTL.

The genomic DNA in step c) can be screened for the presence of one or more markers indicative of QTL7.2 or a variant thereof, as described further above, e.g. by determining the presence of one or more markers selected from the group consisting of:
a) the TT or TC genotype for the Single Nucleotide Polymorphism marker SNP_08 in SEQ ID NO: 8 or in a sequence comprising substantial sequence identity to SEQ ID NO: 8;
b) the CC or CT genotype for the Single Nucleotide Polymorphism marker SNP_09 in SEQ ID NO: 9 or in a sequence comprising substantial sequence identity to SEQ ID NO: 9;
c) the AA or AG genotype for the Single Nucleotide Polymorphism marker SNP_10 in SEQ ID NO: 10 or in a sequence comprising substantial sequence identity to SEQ ID NO: 10;
d) the CC or CA genotype for the Single Nucleotide Polymorphism marker SNP_11 in SEQ ID NO: 11 or in a sequence comprising substantial sequence identity to SEQ ID NO: 11;
e) the CC or CT genotype for the Single Nucleotide Polymorphism marker SNP_12 in SEQ ID NO: 12 or in a sequence comprising substantial sequence identity to SEQ ID NO: 12;
f) the GG or GA genotype for the Single Nucleotide Polymorphism marker SNP_13 in SEQ ID NO: 13 or in a sequence comprising substantial sequence identity to SEQ ID NO: 13;
g) the CC or CT genotype for the Single Nucleotide Polymorphism marker SNP_14 in SEQ ID NO: 14 or in a sequence comprising substantial sequence identity to SEQ ID NO: 14;
h) any wild lettuce genome specific marker, especially *L. virosa*-genome specific marker, located physically in-between SNP_08 and SNP_14, e.g. in between any two markers of SNP_08 to SNP_14.

The genomic DNA in step c) can be screened for the presence of one or more markers indicative of QTL7.1 or a variant thereof, as described further above, e.g. by determining the presence of one or more markers selected from the group consisting of:
i. the TT or TA genotype for the Single Nucleotide Polymorphism marker SNP_15 in SEQ ID NO: 15 or in a sequence comprising substantial sequence identity to SEQ ID NO: 15;
ii. the GG or GA genotype for the Single Nucleotide Polymorphism marker SNP_16 in SEQ ID NO: 16 or in a sequence comprising substantial sequence identity to SEQ ID NO: 16;
iii. the TT or TC genotype for the Single Nucleotide Polymorphism marker SNP_17 in SEQ ID NO: 17 or in a sequence comprising substantial sequence identity to SEQ ID NO: 17;
iv. the GG or GC genotype for the Single Nucleotide Polymorphism marker SNP_18 in SEQ ID NO: 18 or in a sequence comprising substantial sequence identity to SEQ ID NO: 18;
v. the GG or GA genotype for the Single Nucleotide Polymorphism marker SNP_19 in SEQ ID NO: 19 or in a sequence comprising substantial sequence identity to SEQ ID NO: 19;
vi. the TT or TC genotype for the Single Nucleotide Polymorphism marker SNP_20 in SEQ ID NO: 20 or in a sequence comprising substantial sequence identity to SEQ ID NO: 20;
vii. the CC or CA genotype for the Single Nucleotide Polymorphism marker SNP_21 in SEQ ID NO: 21 or in a sequence comprising substantial sequence identity to SEQ ID NO: 21;
viii. the CC or CT genotype for the Single Nucleotide Polymorphism marker SNP_22 in SEQ ID NO: 22 or in a sequence comprising substantial sequence identity to SEQ ID NO: 22;
ix. any wild lettuce genome specific marker, especially *L. virosa*-genome specific marker, located physically in-between SNP_15 and SNP_22, e.g. in between any two markers of SNP_15 to SNP_22.

Alternatively, the genomic DNA in step c) can be screened for the presence of one or more markers indicative of QTL7.1 or a variant thereof, as described further above, e.g. by determining the presence of one or more markers selected from the group consisting of:

- the TT or TC genotype for the Single Nucleotide Polymorphism marker SNP_17 in SEQ ID NO: 17 (or in a sequence comprising substantial sequence identity to SEQ ID NO: 17);
- the TT or TC genotype for the Single Nucleotide Polymorphism marker SNP17.25 in SEQ ID NO: 25 (or in a sequence comprising substantial sequence identity to SEQ ID NO: 25);
- the GG or GC genotype for the Single Nucleotide Polymorphism marker SNP_18 in SEQ ID NO: 18 (or in a sequence comprising substantial sequence identity to SEQ ID NO: 18);
- the GG or GA genotype for the Single Nucleotide Polymorphism marker SNP_19 in SEQ ID NO: 19 (or in a sequence comprising substantial sequence identity to SEQ ID NO: 19);
- any wild lettuce genome specific marker, especially *L. virosa*-genome specific marker, located physically in-between SNP_17 and SNP_19 (e.g. in-between SNP_17 and SNP_18, in between SNP_17 and SNP17.25; or in between SNP17.25 and SNP_19, or in between SNP17.25 and SNP_18, or in between SNP_18 and SNP_19);
- any wild lettuce genome specific marker especially *L. virosa*-genome specific marker, located within a distance of 12 Mb, 10 Mb, preferably within 5 Mb, of any marker selected from SNP_17, SNP_17.25, SNP_18 and SNP_19.

Optionally also *L. virosa* accession specific markers can be screened (VSP2 or VSP4) to distinguish accession types comprising the QTL.

The marker screening can be done by any suitable technique or combination of techniques known to the skilled person, e.g. PCR-based, sequencing based, etc. It is understood that screening of the genomic DNA can be done on plants, plant parts, seeds or on genomic DNA isolated therefrom.

In step d) of the method a plant is identified comprising one or more of the markers, e.g. at least 1, 2, 3, 4, 5, 6 or all 7 of SNP_01 to SNP_07 and/or any marker in-between SNP_01 and SNP_07; or alternatively one or more of the markers of SNP1.23, SNP_02, SNP2.24 or SNP_03 (and optionally VSP1 or VSP3) and/or any marker in-between SNP1.23 and SNP_03; at least at least 1, 2, 3, 4, 5, 6 or all 7 of SNP_08 to SNP_14 and/or any marker in-between SNP_08 and SNP_14; at least 1, 2, 3, 4, 5, 6, 7 or all 8 of SNP_15 to SNP_22 and/or any marker in-between SNP_15 and SNP_22; or alternatively SNP_17, SNP17.25, SNP_18 or SNP_19 (and optionally VSP2 or VSP4) or any marker in between SNP_17 and SNP_19.

Thus, in one aspect a method for generating a cultivated lettuce plant comprising Nr:1 resistance is provided comprising the steps of:

a) Providing a wild lettuce, especially a *Lactuca virosa* plant comprising 1, 2, 3, 4, 5, or more SNP markers indicative of QTL6.1 (or variant); and/or 1, 2, 3, 4, 5, or more SNP markers indicative of QTL7.2 (or variant) and/or 1, 2, 3, 4, 5, or more SNP markers indicative of QTL7.1 (or variant);

b) Crossing said wild lettuce, especially said *Lactuca virosa* plant with a cultivated lettuce plant, which is susceptible against lettuce aphid Nr: 1, to produce F1 seeds;

c) Optionally selfing the plants grown from F1 seeds one or more times to produce F2, F3 or further generation selfing progeny;

d) Crossing said F1 or further generation selfing progeny to the cultivated lettuce plant of step b), to produce a backcross progeny;

e) Selecting backcross progeny which comprise resistance against biotype Nr: 1.

A lettuce plant produced by the method is also encompassed herein.

Method for Transferring One or More of the QTLs Selected from QTL6.1. QTL7.1 and/or QTL7.2 (or Variants Thereof) from a Wild Lettuce (e.g. *L. virosa*) into Cultivated Lettuce (*L. sativa*) to Generate a Nr:1 Resistant Cultivated Lettuce In another aspect a method for transferring one or more of the QTLs selected from QTL6.1, QTL7.1 and/or QTL7.2 (or variants thereof) from a wild lettuce (e.g. *L. virosa*) into cultivated lettuce (*L. sativa*) to generate a Nr:1 resistant cultivated lettuce is provided, comprising:

a) providing a wild lettuce plant comprising QTL6.1, QTL7.1 and/or QTL7.2 (or variants thereof);

b) crossing the wild lettuce plant of a) with a cultivated lettuce plant to generate an F1;

c) optionally selfing the F1 one or more times to generate further selfing progeny;

d) backcrossing the F1 or further selfing progeny one or more times to the cultivated lettuce plant of step b) (the recurrent parent);

e) identifying and/or selecting backcross progeny comprising a genome of the cultivated lettuce plant of step b) (the recurrent parent) comprising an introgression fragment from the wild lettuce plant of a) (donor parent) on chromosome 6 and/or on chromosome 7.

In one aspect the wild lettuce plant of a) is a *L. virosa*. In one aspect the *L. virosa* is Nr:1 resistant when tested in a Nr:1 resistance assay. In one aspect the *L. virosa* parent of a) is NCIMB42086, or progeny thereof obtained by selfing and/or crossing, wherein the progeny comprise QTL6.1, QTL7.1 and/or QTL7.2. In another aspect the plant of a) is a *L. virosa* accession comprising the *virosa* specific markers VSP1 and/or VSP2 or comprising the *virosa* specific markers VSP3 and/or VSP4 (as shown in Table 6 and 7).

The cultivated lettuce of step b) in the method above (and in any other method of the invention) may be any *L. sativa*, such as an inbred line or a variety. It may be of any type, such as leaf or looseleaf, butterhead or Bibb, Romaine or Cos, Crisphead or Iceberg, Celtuce or Stem lettuce. It is preferably a Nr: 1 susceptible plant, although it may also be a plant comprising Nr: 1 resistance conferred by different loci, in order to stack Nr:1 resistance loci in one plant line or variety. It may be an Nr:0 resistant plant. It may comprise the dominant Nr-gene.

When referring to backcrossing and backcross progeny, this may also include progeny obtained by backcrossing (BC) and selfing (S), e.g. BC1S1, BC1S2, BC2S1, etc.

In step e) any of the markers and marker assays described herein can be used.

Plants obtained by the method are also an embodiment of the invention, as described elsewhere herein. These plants are, thus, cultivated *L. sativa* plants (of any type) comprising one or more of the QTLs of the invention on chromosome 6 (QTL6.1 or variant) and/or 7 (QTL7.1 and/or QTL7.2 or variants) in homozygous or heterozygous form.

As sterility barriers may exist between *L. sativa* and wild lettuce plants, such as *L. virosa*, the *L. virosa* plant (e.g. plants grown from seeds having accession number NCIMB 42086 or other *L. virosa* accessions) may be crossed with a bridge species, such as *L. serriola* (Eenink et al. 1982, Euphytica 31:291-299), and/or other methods, such as tetraploidization, may be used to overcome sterility barriers. Thompson and Ryder (1961; US Department of Agriculture, Tech. Bulletin no. 1244), for example, crossed *L. virosa* with a (*L. serriola*×*L. sativa*) hybrid, which produced a sterile F1 interspecific hybrid. However, tetraploidisation of the F1 and subsequent crossing and diploidization enabled to introgress traits from *L. virosa* into *L. sativa*. Also embryo rescue may be used to recover viable embryos from interspecific crosses (Maisonneuve et al. 1995, Euphytica 85: 281-285). Thus, when referring anywhere in the specification to a cultivated lettuce plants (*L. sativa*) comprising one or more QTLs conferring Nr:1 resistance obtainable by crossing an *L. virosa* plant with a cultivated lettuce plant, this may comprise (but is not limited to) steps which overcome sterility barriers, such as the use of a bridge species, embryo rescue and/or colchicine treatment (chromosome doubling).

Method for Screening Cultivated Lettuce Lines or Varieties for the Presence of One or More of the QTLs Selected from QTL6.1, QTL7.1 and/or QTL7.2 (or Variants of any of these)

This method is similar to the method for identifying a wild lettuce plant comprising one or more of the QTLs, but herein cultivated lettuce plants, i.e. *L. sativa* plants, are screened.

The method thus comprises the following steps:
a) providing a cultivated lettuce plant or a plurality of cultivated lettuce plants;
b) optionally testing the cultivated lettuce plant or plurality of plants for Nr:1 resistance in an Nr: 1 resistance assay (e.g. free-choice and/or non-choice);
c) screening the genomic DNA of the plant or plurality of plants of a), or optionally only of the Nr:1 resistant plant or plants identified in b), for the presence of one or more markers indicative of QTL6.1 or a variant thereof and/or indicative of QTL7.1 or a variant thereof and/or indicative of QTL7.2 or a variant thereof; and
d) identifying a plant comprising one or more of said markers of c);
e) optionally testing the plant of d) for Nr:1 resistance in an Nr: 1 resistance assay.

Using this method for example commercial competitor varieties can be screened, in order to determine whether they contain one or more of the QTLs of the instant invention.

Method for Transferring One or More of the QTLs Selected from QTL6.1, QTL7.1 and/or QTL7.2 (or Variants Thereof) from a Cultivated Lettuce (*L. sativa*) into Another Cultivated Lettuce, e.g. into a Nr:1 Susceptible Lettuce Plant Line or Variety The QTLs of the present invention can off course also be transferred from one cultivated *L. sativa* plant to another cultivated *L. sativa* plant, in order to generate different types and different varieties of lettuce which are Nr: 1 resistant.

This method comprises the steps of:
a) providing a *L. sativa* plant comprising one or more or all of QTL6.1, QTL7.1 and/or QTL7.2 or a variant of any of these;
b) crossing the *L. sativa* plant of a) with a second *L. sativa* plant;
c) collecting F1 seeds from said cross and optionally selfing said F1 plants one or more times to produce an F2 or F3 or further selfing population,
d) optionally backcrossing the F1 plant or an F2 or F3 or further selfing plant to the second *L. sativa* plant of b) to produce a backcross population,
e) optionally selfing the backcross population one or more times,
f) identifying a F1, F2, F3, further selfing or backcross plant which comprises one or more or all of the SNP marker genotype indicative of the introgression fragment on chromosome 6 (QTL6.1) and/or indicative of the introgression fragment on chromosome 7 (QTL7.1 and/or QTL7.2).

Introgression fragments comprising QTL6.1, QTL7.1 and QTL7.2 (or variants of any of these) can be transferred all together or individually into another cultivated lettuce plant.

In one aspect the second cultivated lettuce plant of b) is a Nr: 1 susceptible lettuce plant, or at least a plant lacking the QTL(s) which it is to receive from the donor of a).

The new lettuce plant produced may again be any type and any line or variety. Thus, the QTL(s) may be transferred by traditional breeding from one cultivated lettuce to another, e.g. from butterhead to romaine, from a stem lettuce to a Bibb, from a Romaine to a looseleaf, etc. In the course of the transfer the size of the introgression fragment may be reduced by recombination, and some of the markers may thereby not be present in the resulting plant.

Plants produced by this method are also an embodiment of the invention.

Thus, a method is provided for generating a cultivated lettuce plant comprising Nr:1 resistance comprises the steps of:
a) Providing a cultivated lettuce plant comprising 1, 2, 3, 4, 5, or more SNP markers indicative of QTL6.1 (or a variant); and/or 1, 2, 3, 4, 5, or more SNP markers indicative of QTL7.2 (or a variant) and/or 1, 2, 3, 4, 5, or more SNP markers indicative of QTL7.1 (or a variant);
b) Crossing said cultivated lettuce plant with another cultivated lettuce plant, which is susceptible against lettuce aphid Nr:1 to produce F1 seeds;
c) Optionally selfing the plants grown from F1 seeds one or more times to produce F2, F3 or further generation selfing progeny;
d) Identifying lettuce plants grown from F1, F2, F3 or further generation selfing progeny which have a Nr: 1 resistance phenotype and/or which comprise the introgression fragment or a resistance-conferring part of the introgression fragment;
e) Optionally crossing said identified F1 progeny or selfing progeny to the cultivated lettuce plant of step b), to produce a backcross progeny;
f) Optionally selecting backcross progeny which comprises resistance against biotype Nr:1 and/or which comprise the introgression fragment or a resistance-conferring part of the introgression fragment.

In step d) and/or f) markers described herein can be used.

A lettuce plant produced by the method is also encompassed herein.

Method for Using Seeds Deposited Under Accession Number NCIMB42086. Or Descendants Thereof. For Generating Nr:1 Resistant Cultivated Lettuce NCIMB42086 comprises all three QTLs in homozygous form and can thus be used to generate cultivated lettuce lines or varieties comprising one or more of the QTLs, as already described. Likewise descendants of NCIMB42086 which retain one or more of the QTLs can be used to generate cultivated lettuce lines or varieties comprising one or more of the QTLs.

Method for Cultivating Plants of the Invention. i.e. Nr:1 Resistant *L. sativa* Plants Comprising One or More of the QTLs Selected from QTL6.1, QTL7.1 and/or QTL7.2 (or Variants Thereof). In Areas where *N. Ribisnigri* Biotype Nr:1 is Present The plants of the invention can be cultivated in areas of natural Nr:1 infestation. As the QTLs identified herein provide resistance against *N. ribisnigri* biotype Nr:1 not only under free-choice conditions, but also as under non-choice conditions, the resistance is very effective in the field, because one can expect good yields even in situations where the insects have no alternative choice for feeding and reproduction. Resistance which is present under only free-choice conditions is risky to use, as aphids may still choose the plants for feeding and reproduction in situations where no other preferred choice is available.

Further, the QTLs of the invention were shown to provide resistance against different isolates of biotype Nr:1, originating from different countries, such as Germany, France and Spain. The resistance is therefore expected to be effective and durable in Germany, France, Spain, UK and other European countries, as well as other countries of the world where biotype Nr:1 may be found.

In one aspect the QTLs of the invention also provide resistance against biotype Nr:0, at least against European biotypes Nr:0 (i.e. at least against German, French and Spanish biotypes Nr:1). Thus, in one aspect the cultivated lettuce plants of the invention (comprising one or more of the QTLs) are resistant against Nr:1 and at least also against European biotypes of Nr:0. In one aspect the plants are susceptible against US or Californian biotypes of Nr:0, although this has yet to be tested.

The field resistance of plants of the invention (comprising one or more of the QTLs) against biotype Nr:1, is significantly higher (i.e. as measurable by significantly lower average numbers of aphids) than for susceptible controls, such as Mafalda. This can, for example, be tested in open-field tests in areas of natural Nr:1 infestation (e.g. in Murcia, Spain) by seeding or planting lettuce plants of the line or variety comprising one or more of the introgression fragments in their genome in the field, together with suitable controls, such as susceptible variety Mafalda and/or a genetic control line. Preferably at least about 10, 15, 20 or more plants per line or variety are included, as well as at least two or preferably three replicates. The plants can be monitored weekly and once sufficient infestation is seen on the susceptible control (e.g. at least 100 or more aphids), the numbers of lettuce aphids on a representative number of plants of each line or variety can be counted. Preferably, in field conditions, the average number of aphids of biotype Nr:1 is significantly lower on plants of the invention compared to susceptible controls, such as Mafalda. The average number of aphids is preferably not determined on young seedlings (below the 3-4 true leaf stage), as it was found in the Examples that on such young plants the resistance is not fully expressed yet.

Although plants of NCIMB42086 (comprising all three QTLs in homozygous form) were found to be completely free of Nr:1 aphids in free-choice and non-choice field tests carried out in Spain, it may be (without being limited by speculation) that a cultivated lettuce plant comprising only one or two of the QTLs (or variants), or not all three introgressions comprising the QTLs (or variants) in homozygous form, may not be completely resistant against Nr:1. Therefore, in one aspect, cultivated lettuce plants of the invention, comprising one or more of the QTLs (QTL6.1, QTL7.1 and/or QTL7.2 or variants of any of these) in homozygous or heterozygous form, comprise an average number of aphids of biotype Nr:1 is equal to or less than 50%, 49%, 48%, 47%, 46%, 45%, 44%, 43% 40%, 30%, 20%, 10%, 5%, 3%, 2% or 1%, of the average number of aphids found on variety Mafalda (or a different Nr:1 susceptible variety, preferably comprising the Nr gene), or on the genetic control, when grown under the same conditions. For example a free choice or a non-choice trial can be done in the field as described in the Examples in order to determine the average number of Nr:1 aphids on plants of the invention and on the control plants.

In one aspect the cultivated lettuce plants of the invention comprise equal to or less than an average of 50 *N. ribisnigri* biotype Nr:1 aphids, or equal to or less than an average of 40, 30, 20, or 10 Nr:1 aphids. In another aspect the cultivated lettuce plants of the invention comprise (on average) zero Nr:1 aphids or essentially zero Nr:1 aphids (equal to or less than 5 aphids on average) when grown in the field, while the control plant, such as Mafalda, comprises significant numbers of biotype Nr:1 aphids. A significant number is at least 100 aphids on average, 150, 200, 250 or more.

In another aspect the cultivated lettuce plants of the invention comprise equal to or less than an average of 50 *N. ribisnigri* aphids (of any biotype, i.e. biotype Nr:0 and biotype Nr:1), or equal to or less than an average of 40, 30, 20, or 10 aphids of *N. ribisnigri* aphids. In another aspect the cultivated lettuce plants of the invention comprise (on average) zero aphids *N. ribisnigri* aphids or essentially zero aphids (equal to or less than 5 aphids on average) when grown in the field in an area where both Nr:1 and Nr:0 are present, while the control plant, such as Mafalda, comprises significant numbers of biotype Nr:1 aphids and while a Nr:0 susceptible variety comprises significant numbers of biotype Nr:0. A significant number is at least 100 aphids on average, 150, 200, 250 or more.

Cultivated lettuce plants of the invention may be of any type. They may be green lettuce or red lettuce, green and red lettuce (e.g. spotted), babyleaf, little-gem type lettuce, loose-leaf lettuce (also referred to as cutting or bunching lettuce), butterhead lettuce, Bibb lettuce, Batavia (or Summercrisp) lettuce, heading lettuce, romaine (or cos) lettuce, crisphead (or iceberg) lettuce, multileaf lettuce, Great Lakes Group lettuce, Vanguard Group lettuce, Salinas Group lettuce, Eastern (Ithaca) Group lettuce, Celtuce or Stem or Latin lettuce types, etc. They may also be of inter-market type, e.g. a cos with iceberg features features, or a iceberg with cos features, etc. They may be inbred lines, F1 hybrids, double haploids, transgenic plants, mutant plants, etc.

In one aspect the introgression fragment(s) comprising one or more of QTLs 6.1, 7.1 and/or 7.2 (or variants) is in homozygous form in the cultivated lettuce plant of the invention. Selfing one or more times will ensure that the introgression fragments are in homozygous form and the SNP marker(s) then also show the homozygous genotype.

In a further aspect the cultivated lettuce plant of the invention has good fertility and is easily crossable with other cultivated lettuce lines or varieties. Preferably any wild genome fragments (e.g. *L. virosa*) which are co-introduced with the QTL(s) and which confer any negative characteristics in the cultivated plant, such as low fertility and/or dwarf growth, are removed. This can be done by selecting recombinants having a shorter introgression fragment, but which retain the Nr:1-resistance conferring part.

Plants of the invention can be used to generate progeny (or descendants), which have or retain the QTL(s) (or variants) and the Nr:1 resistance phenotype. To generate progeny, a cultivated lettuce according to the invention can be selfed and/or crossed one or more times with another lettuce plant and seeds can be collected.

Also seeds from which any of the plants of the invention can be grown are provided.

In one embodiment, the use of a lettuce plant, of which representative seeds have been deposited under accession number NCIMB 42086, or progeny thereof (e.g. obtained by selfing), for generating a Nr: 1 resistant cultivated lettuce plant is provided.

In another embodiment, the use of cultivated lettuce plant comprising a Nr:1 resistance phenotype conferred by one or more QTL(s) as found in/as obtainable from seeds deposited under accession number NCIMB 42086, or from progeny thereof (e.g. obtained by selfing), for generating a Nr:1 resistant cultivated lettuce plant is provided.

Seed

Also seeds from which any of the plants of the invention can be grown are provided, as are containers or packages containing or comprising such seeds. Seeds can be distinguished from other seeds due to the presence of the one or more QTLs (as can be tested using molecular marker tests described herein) and phenotypically.

In one aspect, seeds are packaged into small and/or large containers (e.g., bags, cartons, cans, etc.). The seeds may be pelleted prior to packing (to form pills or pellets) and/or treated with various compounds, such as seed coatings.

Seed pelleting can be combined with film coating (Halmer, P. 2000. Commercial seed treatment technology. In: Seed technology and its biological basis. Eds: Black, M. and Bewley, J. D., pages 257-286). Pelleting creates round or rounded shapes, which are easily sown with modern sowing machines. A pelleting mixture typically contains seeds and at least glue and filler material. The latter could be, for example, clay, mica, chalk or cellulose. In addition, certain additives can be included to improve particular properties of the pellet, e.g., a seed treatment formulation comprising at least one insecticidal, acaricidal, nematicidal or fungicidal compound can be added directly into the pelleting mixture or in separate layers. A seed treatment formulation can include one of these types of compounds only, a mixture of two or more of the same type of compounds or a mixture of one or more of the same type of compounds with at least one other insecticide, acaricide, nematicide or fungicide.

Formulations especially suitable for the application as a seed treatment can be added to the seed in the form of a film coating including also the possibility of using the coating in or on a pellet, as well as including the seed treatment formulation directly into the pellet mixture. Characteristically, a film coating is a uniform, dust-free, water permeable film, evenly covering the surface of all individual seeds (Halmer, P. 2000. Commercial seed treatment technology. In: Seed technology and its biological basis. Eds: Black, M. and Bewley, J. D., pages 257-286). Besides the formulation, the coating mixture generally also contains other ingredients such as water, glue (typically a polymer), filler materials, pigments and certain additives to improve particular properties of the coating. Several coatings can be combined on a single seed.

In addition, several combinations with film coating are possible: the film coating can be added on the outside of the pellet, in between two layers of pelleting material, and directly on the seed before the pelleting material is added. Also more than 1 film coating layer can be incorporated in a single pellet. A special type of pelleting is encrusting. This technique uses less filler material, and the result is a 'mini-pellet'.

Seeds may also be primed. Of all the commercially planted vegetable seeds, lettuce is most often primed. Priming is a water-based process that is performed on seeds to increase uniformity of germination and emergence from the soil, and thus enhance vegetable stand establishment. Priming decreases the time span between the emergence of the first and the last seedlings. Methods how to prime lettuce seeds are well known in the art (see, e.g., Hill et al HortScience 42(6): 1436, 2007).

Plant parts and Vegetative Reproductions

In a further aspect plant parts, obtained from (obtainable from) a plant of the invention are provided herein, and containers or packages comprising said plant parts. Any plant parts can be distinguished from other lettuce plant parts by the presence of a recombinant chromosome 6 and/or 7, i.e. by the presence of an introgression fragment from a wild lettuce, e.g. from *L. virosa*, on chromosome 6 and/or 7. This can be easily tested by the presence of one or more or all of the markers described herein.

In a preferred embodiment the plant parts are leaves or heads of cultivated lettuce plants of the invention, preferably harvested leaves or heads, or parts of these.

Other plant parts, of plants of the invention, include stems, cuttings, petioles, cotyledons, flowers, anthers, pollen, ovaries, roots, root tips, protoplasts, callus, microspores, stalks, ovules, shoots, seeds, embryos, embryo sacs, cells, meristems, buds etc. Seeds include for example seeds produced on the plant of the invention after self-pollination or after pollination with pollen from another lettuce plant.

In a further aspect, the plant part is a plant cell or a plant tissue. In still a further aspect, the plant part is a non-regenerable cell or a regenerable cell. In another aspect the plant cell is a somatic cell. In a further aspect the plant cell is a reproductive cell, such as an ovule or pollen. These cells are haploid. When they are regenerated into whole plants, they comprise the haploid genome of the starting plant. If chromosome doubling occurs (e.g. through chemical treatment), a double haploid plant can be regenerated. In one aspect the plant of the invention is a haploid or a double haploid lettuce plant.

Moreover, there is provided an in vitro cell culture or tissue culture of lettuce plants of the invention in which the cell- or tissue culture is derived from a plant parts described above, such as, for example and without limitation, leaves, pollen, embryos, cotyledon, hypocotyls, meristematic cells, roots, root tips, anthers, flowers, seeds or stems, somatic cells, reproductive cells. For example, leaf-, hypocotyl- or stem-cuttings may be used in tissue culture.

In a specific aspect an in vitro cell culture or tissue culture of lettuce plants of the invention is provided in which the cell- or tissue culture is derived from a plant parts described above, wherein such plant parts do not comprise reproductive cells. In another embodiment, the cell culture or tissue culture does not comprise regenerable cells. In one aspect non-propagating cells of the invention are provided and a cell culture or tissue culture comprising or consisting of non-propagating cells of the invention.

Also provided are lettuce plants regenerated from the above-described plant parts, or regenerated from the above-described cell or tissue cultures, said regenerated plant having Nr: 1 resistance, i.e. retains the introgression fragment(s) conferring Nr:1 resistance. These plants can also be referred to as vegetative propagations of plants of the invention.

Also provided are harvested leaves and/or heads of plants of the invention and packages comprising a plurality of leaves and/or heads of plants of the invention, such as 1, 2, 3, 4, 5, 10, 12, 20 heads.

The invention also provides for a food or feed product comprising or consisting of a plant part described herein. The food or feed product may be fresh or processed, e.g., canned, steamed, boiled, fried, blanched and/or frozen etc. Examples are salad or salad mixtures comprising leaves or parts of leaves of plants of the invention.

A lettuce plant of the invention or a progeny thereof retaining the Nr:1 resistance phenotype and the introgression fragment(s), and parts of the afore-mentioned plants, can be suitably packed for, e.g., transport, and/or sold fresh. Such parts encompass any cells, tissues and organs obtainable from the seedlings or plants, such as but not limited to: heads, cuttings, pollen, leaves, parts of leaves, and the like. Heads and leaves may be harvested as baby-leaf or later. A plant, plants or parts thereof may be packed in a container (e.g., bags, cartons, cans, etc.) alone or together with other plants or materials. Parts can be stored and/or processed further. Encompassed are therefore also food or feed products comprising one or more of such parts, such leaves or parts thereof obtainable from a plant of the invention, a progeny thereof and parts of the afore-mentioned plants. For example, containers such as cans, boxes, crates, bags, cartons, Modified Atmosphere Packagings, films (e.g. biodegradable films), etc. comprising plant parts of plants (fresh and/or processed) of the invention are also provided herein.

Plants and Progeny (Descendants)

In another embodiment, plants and parts of lettuce plants of the invention, and progeny of lettuce plants of the invention are provided, e.g., grown from seeds, produced by sexual or vegetative reproduction, regenerated from the above-described plant parts, or regenerated from cell or tissue culture, in which the reproduced (seed propagated or vegetatively propagated) plant comprises the Nr:1 resistance phenotype (and thus the introgression fragment(s) conferring Nr: 1 resistance).

As mentioned before, whether or not a plant, progeny or vegetative propagation comprises the Nr:1 resistance phenotype can be tested phenotypically using e.g. the choice-test and/or non-choice test, either field tests or controlled environment tests, as described above or in the Examples, and/or using molecular techniques such as molecular marker analysis (using one or more or all of the markers described herein), DNA sequencing (e.g. whole genome sequencing to identify the *L. virosa* introgression), chromosome painting, etc.

In one embodiment, the Nr: 1 resistance QTL(s) obtainable from (obtained from) NCIMB42086 or from other wild lettuces (e.g. other Nr: 1 resistant *L. virosa* accessions) can be combined with other genes, such as other Nr: 1 resistance genes (e.g. single genes or QTLs on different chromosomes), with Nr:0 resistance genes (e.g. the Nr gene) or with other traits, such resistance against downy mildew, *Sclerotinia* rot, *Botrytis*, powdery mildew, anthracnose, bottom rot, corky root rot, lettuce mosaic virus, big vein, lettuce aphid, beet western yellows and aster yellows. Resistance against one or more of the following pests may also be present or introduced into plants of the invention: *Sclerotinia* minor (leaf drop), *Sclerotinia sclerotiorum* (leaf drop), *Rhizoctonia solani* (bottom drop), *Erysiphe cichoracearum* (powdery mildew), *Fusarium oxysporum* f. sp. *lactucae* (*Fusarium* wilt) resistance. Other resistance genes, against pathogenic viruses (e.g. Lettuce infectious yellows virus (LIYV), lettuce mosaic virus (LMV), Cucumber mosaic virus (CMV), Beet western yellows virus (BWYV), Alfalfa mosaic virus (AMV)), fungi, bacteria or lettuce pests may also be introduced.

Furthermore, the invention provides for progeny (or descendants) comprising or retaining the Nr:1 resistance conferring QTL(s) of the invention, such as progeny obtained by, e.g., selfing one or more times and/or cross-pollinating a plant of the invention with another lettuce plant of a different variety or breeding line, or with a lettuce plant of the invention one or more times. In particular, the invention provides for progeny that retain QTL6.1, QTL7.1 and/or QTL7.2 as found in NCIMB 42086. In one aspect the invention provides for a progeny plant comprising the Nr:1 resistance, such as a progeny plant that is produced from a cultivated lettuce plant of the invention comprising the Nr: 1 resistance by one or more methods selected from the group consisting of: selfing, crossing, mutation, double haploid production or transformation.

Mutation may be spontaneous mutations or human induced mutations or somaclonal mutations. See e.g. Mou 2011, Mutations in lettuce improvement, International Journal of Plant Genomics Volume 2011, Article ID 723518.

In one embodiment, plants or seeds of the invention may also be mutated (by e.g. irradiation, chemical mutagenesis, heat treatment, TILLING, etc.) and/or mutated seeds or plants may be selected (e.g. natural variants, somaclonal variants, etc.) in order to change one or more characteristics of the plants. Similarly, plants of the invention may be transformed and regenerated, whereby one or more chimeric genes are introduced into the plants. Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into the plants, or progeny thereof, by transforming a plant of the invention or progeny thereof with a transgene that confers the desired trait, wherein the transformed plant retains the Nr:1 resistance conferring introgression(s) and contains the desired trait.

The Nr: 1 resistance conferring QTL(s) may be transferred to progeny by further breeding, especially to other cultivated lettuce plants. In one aspect progeny are $F_1$ progeny obtained by crossing a cultivated lettuce plant of the invention with another plant or S1 progeny obtained by selfing a plant of the invention. Also encompassed are F2 progeny obtained by selfing the $F_1$ plants, F3, F4 or further descendants obtained by selfing and/or backcrossing, which retain the one or more QTL(s). "Further breeding" encompasses traditional breeding techniques (e.g., selfing, crossing, backcrossing), marker assisted breeding, and/or mutation breeding. In one embodiment, the progeny comprise QTL6.1, QTL7.1 and/or QTL7.2 as present in NCIMB 42086.

In one aspect haploid plants and/or double haploid plants of plant of the invention are encompassed herein. Haploid and double haploid (DH) plants can for example be produced by anther or microspore culture and regeneration into a whole plant. For DH production chromosome doubling may be induced using known methods, such as colchicine treatment or the like. So, in one aspect a cultivated lettuce plant is provided, comprising one or more Nr:1 resistance conferring QTLs as describe, wherein the plant is a double haploid plant.

In another embodiment the invention relates to a method for producing lettuce seed, comprising crossing a cultivated lettuce plant of the invention with itself or a different lettuce plant and harvesting the resulting seed. In a further embodiment the invention relates to seed produced according to this method and/or a lettuce plant produced by growing such seed.

Thus, in one aspect progeny of a cultivated lettuce plant of the invention are provided, wherein the progeny plant is produced by selfing, crossing, mutation, double haploid production or transformation and wherein the progeny retain the Nr:1 resistance described herein In still yet another aspect, the invention provides a method of determining the genotype of a plant of the invention comprising detecting in the genome of the plant at least a first polymorphism (e.g. one or more of the markers described herein). The method may, in certain embodiments, comprise detecting a plurality of polymorphisms in the genome of the plant (e.g. two or more of the markers described herein, indicative of QTL6.1, QTL7.1, QTL7.2 or variants of any of these). For example, a sample of nucleic acid is obtained from a plant and a polymorphism or a plurality of polymorphisms is detected in said nucleic acids. The method may further comprise storing the results of the step of detecting the plurality of polymorphisms on a computer readable medium.

Apart from the SNP markers provided herein, also more molecular markers can be developed by the skilled person, e.g. in-between any of the markers provided herein, or other new markers, e.g. markers linked to variants of QTL6.1, QTL7.1 and/or QTL7.2. The skilled person knows how to develop molecular markers. For example, this can be done by crossing a Nr:1 resistant lettuce plant of the invention (either a cultivated lettuce or a wild lettuce, such as NCIMB42086) with a Nr:1 susceptible lettuce plant and developing a segregating population (e.g. F2 or backcross population) from that cross. The segregating population can then be phenotyped for Nr:1 resistance and genotyped using e.g. molecular markers such as SNPs (Single Nucleotide Polymorphisms), AFLPs (Amplified Fragment Length Polymorphisms; see, e.g., EP 534 858), or others, and by software analysis molecular markers which co-segregate with the Nr: 1 resistance phenotype in the segregating population can be identified.

In one aspect the wild *L. virosa* accession from which any of QTLs QTL6.1 or variant, QTL7.1 or variant and/or QTL7.2 or variant are introgressed into cultivated lettuce are not the following accessions: CGN13361, CGN16266, CGN16272, CGN04757, CGN04930, CGN04973, CGN16274, CGN21399 or CGN05148.

Deposit Information

The QTLs according to the invention were identified in, and derived from, progeny of a sample of a wild *L. virosa* accession, PI273597 (source US NGRP; National Genetic Resource Program, www.ars-grin.gov), originating from Germany (Baden Württemberg). A Nr:1 resistant plant identified in the Examples below was grown and multiplied, and a representative sample of seeds were deposited by Nunhems B.V. on 5 Dec. 2012 under accession number NCIMB 42086. Thus, a total of 2500 seeds of *L. virosa* NCIMB 42086 were deposited by Nunhems B.V. on 5 Dec. 2012, at the NCIMB Ltd., Ferguson Building, Craibstone Estate, Bucksburn, Aberdeen AB21 9YA, United Kingdom (NCIMB). Access to the deposit will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request or for the enforceable life of the patent whichever is longer, and will be replaced if it ever becomes nonviable during that period. Applicant does not waive any rights granted under this patent on this application or under the Plant Variety Protection Act (7 USC 2321 et seq.).

Various modifications and variations of the described products and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in plant breeding, chemistry, biology, plant pathology or related fields are intended to be within the scope of the following claims.

The present invention will be further illustrated in the following Examples which are given for illustration purposes only and are not intended to limit the invention in any way.

EXAMPLES

Example 1—Nr: 1 Resistance in the Free Choice Test 1.1 Plant Material

Seeds were sown in plastic trays (4×7 pots). The plastic trays were filled with a soil mixture composed of two different sources of peat. Once sown, the trays are placed in plastic boxes. These boxes were then placed on the shelves in climate cells (16/8 hours day/night cycle using fluorescent light tubes; light intensity was approximately 50 $\mu mol \cdot m^{-2} \cdot s^{-1}$ PAR (Photosynthetically Active Radiation); temperature for day/night periods was 20/16° C.; relative humidity was set to 80% constant). During sowing, one to two seeds were placed in each pot. Approximately one week after germination, the germinated plantlets were thinned as necessary, i.e., only one plantlet was kept per pot. The plants were kept in the climate cells (environmental conditions described above are kept throughout the whole trial) until the end of the experiment. Watering was done when required.

1.2 Multiplier Plant Material

Multiplier plants are the plants used to produce the aphid population required for the test. The multiplier plants were sown in week 1. Seeds were germinated and plants maintained in the same way as the tested plant material. The open-field butterhead variety Mafalda (Nunhems/Bayer-CropScience Vegetable Seeds) was used as the multiplier plant, but other Nr:0 resistant plants could equally be used.

1.3 Trial Design

The climate cell could accommodate up to six mobile shelving units (MSU). Each unit was composed of three shelves/plateaus. A maximum of three plastic boxes, each containing up to 28 plants, could be stored on a single shelf.

The wild accession NCIMB42086, together with 13 other wild accessions, were compared for their resistance levels against biotype Nr: 1. In the climate cell, 36 boxes were used. Each box contained two plants of each plant lines/ accession (the positions of the plants in each box were randomized). The 36 boxes were then placed on the lower two plateau of the six MSU. No known susceptible candidates were included.

1.4 Insect

One Nr: 1 aphid isolate originally came from a lettuce field in the Pfalz area in Germany. The other Nr: 1 aphid isolate originally came from a lettuce field near Perpignan, France.

When the aphid was not needed for trial purpose, a small colony of insects was retained on Mafalda "maintainer" plants (5 to 10 individual plants) in the climate cell. The plants were kept in a single box.

1.5 Inoculum Production

The rearing of the aphid population used for a trial (i.e., the "inoculum") was started in week 4 of the planning. The rearing was started by dropping nymphs and adults (wingless) aphids on the top of 3 week old Mafalda plants. Approximately 500 aphids were used on a box containing 28 plants. The plants and aphids were stored in boxes and kept open on shelves in the climate cell using the environmental conditions described above. Once inoculated, the aphid population was left to develop on the multiplier plants for three weeks, i.e., until required for the inoculation of the trial.

1.6 Trial Inoculation

The trialed plants were inoculated in week 7, i.e., when the plants were 3 weeks old.

Precisely 20 aphids were transferred on the top of each tested plant. This was achieved by using a paintbrush to pick up the insects from the multiplier plants and laying them onto the heart of the tested plants. Only indeterminate nymphs and adults were used. Aphids that were visibly winged were not included.

1.7 Trial Planning

| Week | Events |
|---|---|
| 1 | Sowing multiplier plants |
| 4 | (i) Infestation of multiplier plants with wingless adults |
|   | (ii) Sowing of tested plant material |
| 5 | Thinning |
| 7 | Tested plants inoculation |
| 8 | Trial scoring at 1 wpi (week post inoculation) |
| 9 | Trial scoring at 2 wpi (week post inoculation) |
| 10 | Trial scoring at 3 wpi (week post inoculation) |
| 11 | Trial scoring at 4 wpi (week post inoculation) |
| 12 | Trial scoring at 5 wpi (week post inoculation) |

1.8 Result Collection and Analysis

The number of aphids present on each individual plants was counted. The counting was done weekly for a period of 5 weeks post inoculation (see trial planning above).

1.9 Results of the Free Choice Test

Figure 2A:
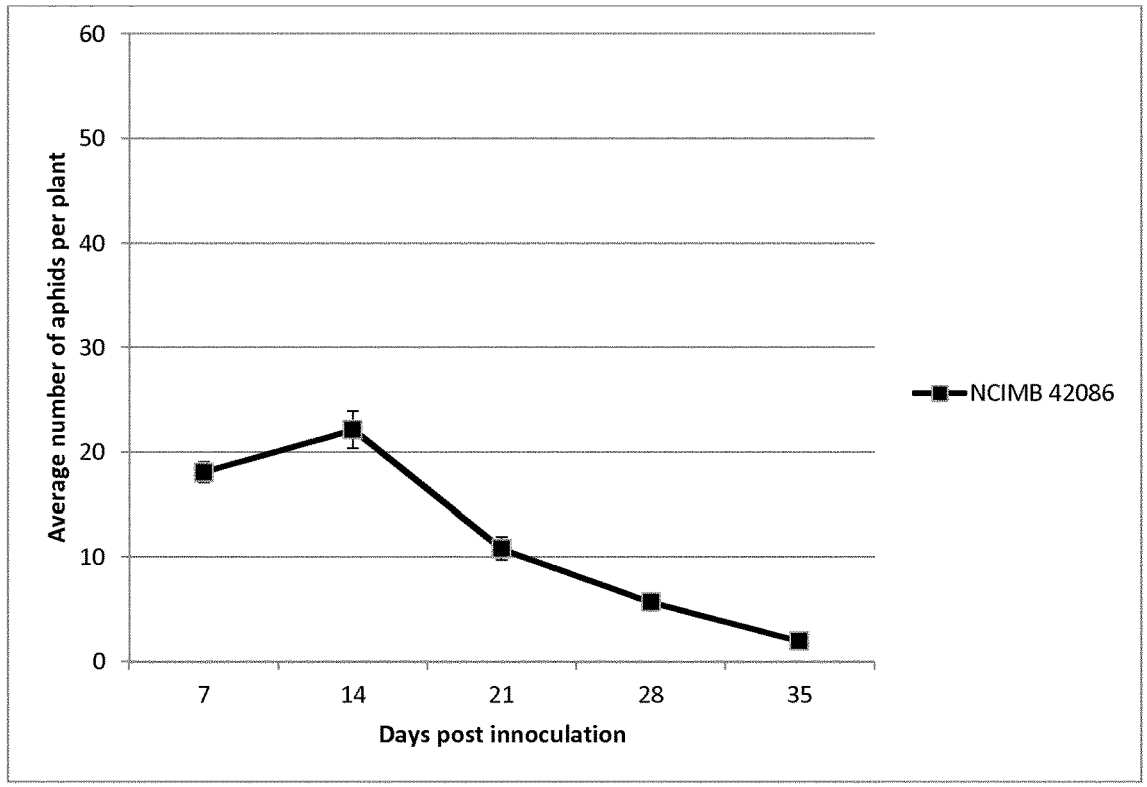
Figure 2B:
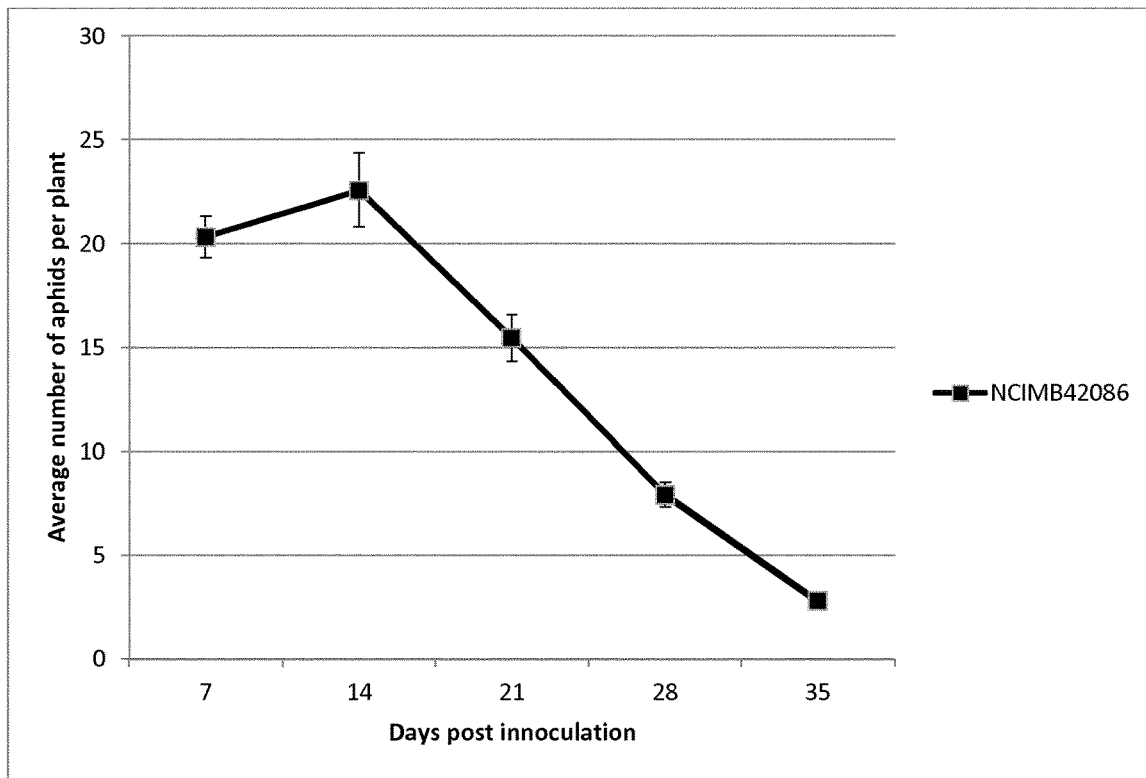

The results of the (free) choice-test are shown in FIGS. 2A and 2B. The results show that with both the German (FIG. 2A) and the French (FIG. 2B) Nr: 1 isolates plants of NCIMB 42086 had very few aphids and thus a higher level of Nr: 1 resistance. Average aphid numbers on NCIMB 42086 initially increased, but only to an average number of 22 (German isolate) and 22.5 (French isolate). After the initial increase in aphid numbers, numbers decreased steadily until they reached an average of 1.95 (German isolate) and 2.79 (French isolate) after 5 weeks on NCIMB 42086.

Thus in young plants of about 8 weeks old virtually no Nr: 1 aphids were found on NCIMB42086 under free-choice conditions.

Example 2—Nr:1 Resistance in a Non-Choice Test

2.1 Protocol Description of the Nr: 1 Non-Choice Test

The protocol used during non-choice tests was almost identical to the one of the choice test in Example 1. Still, differences were present in the setup of the tested plant material, in the climate cell and the design of the trial itself.

Contrary to the choice test, in the non-choice test the boxes were individually contained in plastic tents.

Additionally, a single plant genotype (single lines/accessions) was used in each box/cage unit: in other words, no boxes contained combinations of tested plant lines.

The resistance levels present in NCIMB 42086 and three other accessions were compared in a non-choice test. Variety Mafalda was used as a negative control.

For each plant line, four cages were used. A box containing 18 plants of a single line was placed in the cages. The cages were then placed in a climate cell in a semi-randomized manner. A total of 20 cages and 360 plants were used (72 plants per line or accession).

Aphid inoculation and collection of results was done as described in Example 1, except that only the German Nr: 1 isolate was tested.

2.2 Results of the Non-Choice Test

Figure 1B:
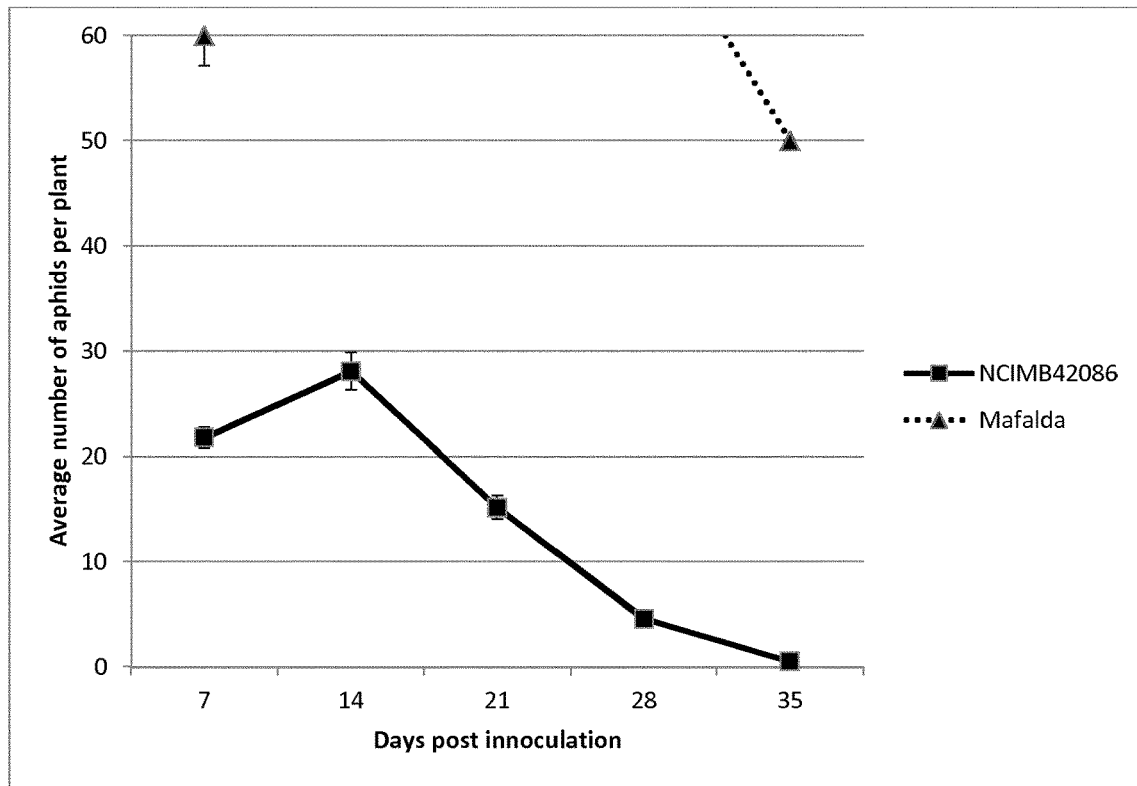

Results of the non-choice test are shown in FIG. 1A and FIG. 1B, which shows a larger scale.

As can be seen, NCIMB 42086 has resistance against biotype Nr: 1, i.e. the average number of aphids is significantly lower than in the susceptible control variety Mafalda. Initially the average aphid number increased slightly but not to above 30 (in NCIMB 42086 it was 28 after two weeks), after which it decreased continuously to zero.

Thus, in young plants of about 8 weeks old no Nr: 1 aphids were found on NCIMB 42086 under non-choice conditions.

Example 2—Field Tests of Semi-Adult and Adult Plants (Free Choice and Non-Choice)

2.1 Free-Choice Field Trial

2.1.1 Plant Growth

For each trial, seeds were sown in individual mixed compost/peat "plugs" and germinated in unheated greenhouses. Approximately 7 to 9 weeks after sowing, germinated plantlets were transplanted onto raised beds in the field. The field was located in the province of Murcia, Spain. Watering was done using watering tubing placed on the top of the raised beds, amongst the rows of plants. Plants were kept in this location until the end of the trials.

2.1.2 Trial Design

Two independent trials were run during two consecutive years, referred to as Year 1 and Year 2 ($Y_1$ and $Y_2$ respectively). The same trial design was used for both trials and his detailed below.

Five different plant lines were tested in the field, amongst them NCIMB 42086 and the control varieties Mafalda and Scala (both varieties of Nunhems/Bayer CropScience Vegetable Seeds). Both Mafalda and Scala are Nr:0 resistant, but Nr: 1 susceptible. Scala is a cos/Romaine type.

Raised beds were used for each trial. On each raised beds, plants were sown in replicates of 16 plants and 5 replicates were sown per raised bed. The test was partially randomized, i.e., the trials were transplanted to ensure that each of the plant lines was represented on each raised bed but for each raised bed, the order of the replicates was randomized.

2.1.3 Insect and Inoculation

The purpose of the trials was to investigate *N. ribisnigri* Nr:1 resistance in field conditions. The plants were not purposefully inoculated, but left to be infested with naturally occurring population of Nr:1 aphids. Samples of insects were collected at the end of the trials for identification under microscopes.

2.1.4 Result Collection and Analysis

The resistance of the different plant lines tested was assessed by counting the number of aphids present on each individual plants. The counting was done 14 weeks after transplanting during Trial $Y_1$ and 11 weeks after transplanting during Trial $Y_2$ 2.1.5—Results of the Free Choice Field Test Year 1 and Year 2

In both trials adult plants (18 to 20 weeks old) of NCIMB42086 had no aphids at all, while the control variety Mafalda and the Nr:1 susceptible variety Scala both had significant numbers of aphids of biotype Nr:1.

2.2 Non-Choice Field Trial 2.2.1—Plant Growth

During Year 2 a non-choice, cage trial was conducted in the field, alongside the free choice trial described above. As described above, plants were germinated in unheated greenhouse before being transferred onto raised beds in the fields about 7 to 9 weeks after sowing. Water was also provided via tubing placed amongst the plants on the top of the raised beds. However, in contrast to the free choice trials, plants were enclosed in cages (approximately 10 m³ each) constructed with insect-proof mesh (size of the mesh was sufficient to prevent Thrips entry).

2.2.2—Trial Design

Two individual cages were used in the field. In each cage two raised beds were used. 20 plants were used on each bed, i.e., 40 plants per cage.

A single plant line was transplanted in each cage, i.e., either NCIMB42086 or Mafalda.

2.2.3 Insect and Inoculation

*N. ribisnigri* aphids needed for the inoculation of the tested plant material were produced on plots of Mafalda plants growing in a nearby field. The plots were passively infested with a naturally occurring population of Nr: 1 aphids.

On the day of inoculation (plants were about 8 week old), apterous adults were collected from the Mafalda plants. The collected aphids were then transferred individually on the top of each tested plant with the help of a paintbrush. Precisely 10 insects were deposited onto each tested plant.

2.2.4—Data Collection and Analysis

The resistance of the different plant lines tested was assessed by counting the number of aphids present on each individual plant. The counting was done approximately 3 weeks after inoculating.

2.2.5 Results of Non-Choice Field Trial of Semi-Adult Plants (about 11 Week Old Plants)

The results are shown in FIG. 4. NCIMB42086 had no aphids at all, while the control variety Mafalda had significant numbers of aphids of biotype Nr: 1 (>300).

2.2.6 Conclusions of Free Choice and Non-Choice Field Trials of Semi-Adult and Adult Plants The results show that the Nr: 1 resistance found on young plants (Example 1, approximately 8 week old plants) of NCIMB 42086 in climate cells is highly effective in the field, both in free-choice and in non-choice trials of semi-adult and adult plants. Resistance in the field appears to be complete (no aphids at all), both under free-choice and non-choice conditions. NCIMB42086 is thus resistant against different Nr: 1 populations, German, French and Spanish.

Example 3—QTL Mapping of Nr:1 Resistance

In order to identify how many genetic loci and which genetic loci are responsible for the Nr:1 resistance of NCIMB42086, NCIMB42086 was crossed to a *N. ribisnigri* susceptible lettuce cultivar. The F1 was backcrossed to the *L. sativa* parent, to generate a BC1 population, which was used for QTL mapping.

Phenotyping data (total number of aphids of biotype Nr:1 per plant) was collected at two time-points post inoculation, two weeks and three weeks post inoculation with aphids of biotype Nr: 1.

Results

Three QTLs were identified, one on chromosome 6 and two on chromosome 7, as shown below and on FIG. 3. The physical position on the chromosomes is based on the published lettuce genome, lgr.genomecenter.ucdavis.edu.

TABLE 1

Chromosome 6-SNP markers linked to QTL6.1

| Marker name | Position in cM | Physical position of SNP (in bases) on chromosome 6 | Genotype of Nr:1 susceptible *L. sativa* parent (wild type genotype) | Genotype of NCIMB42086 (Nr:1 resistant genotype-homozygous) | Genotype heterozygous (Nr:1 resistant genotype heterozygous) | Genomic secquence comprising SNP |
|---|---|---|---|---|---|---|
| SNP_01 | 38.3 | 60688939 | TT | AA | AT | TCATATGGATTAACCATTGGTG CAAACATAGCTGCCCCTGTATA TAATCATCATCCATAAATCATT AAAT[A/T]TGTGAAGTTTTTATA AAGGTTTAGATTGTGAACAGTA AAGTTACCTGCGATTTTAGAAG GTATGTGCTTT (SEQ ID NO: 1) |
| SNP_02 | 115.1 | 117931305 | TT | CC | CT | AATCAACATCAAGCCTCTTCAA GCTAGCTTCACAACAAGCCCTC ACGTACTCAGGTTCCCCGTGGA CTTC[C/T]GATTGACCGATTGTT TCCCCAAATTTGATCCCAAATT TCGTGGCTAATTGAACATCCTC |

TABLE 1-continued

Chromosome 6-SNP markers linked to QTL6.1

| Marker name | Position in cM | Physical position of SNP (in bases) on chromosome 6 | Genotype of Nr:1 susceptible L. sativa parent (wild type genotype) | Genotype of NCIMB42086 (Nr:1 resistant genotype-homozygous | Genotype heterozygous (Nr:1 resistant genotype heterozygous | Genomic secquence comprising SNP |
| --- | --- | --- | --- | --- | --- | --- |
| | | | | | | TCTCTTCACTC (SEQ ID NO: 2) |
| SNP_03 | 188.5 | 161579227 | CC | AA | AC | TAGGGTTTGCGAACAAGATCGA GTTGCCGGAGATTCTCCAAGGA CTGCTCTTGGCATCTTCCGACG ACAG[A/C]GGTCTTGCTCTCACT GCGACGTTGATTCTCTCCATGG TTGCTCGGATTGGAGTAGGTGG AGAGAGGGTTT (SEQ ID NO: 3) |
| SNP_04 | 195.4 | 191681086 | AA | GG | GA | TAGAATAGATTTATTGATATGT TCCTTAATGTTGGCTTCCAAAT GTTAATCATAAGTTGTACCAAT ATGT[A/G]ATTAAATAAGTTTTA ATTTAAATGCATTGAAAGGTGA AAATTATACTGTAACAAGTTTG TGAATCTTCAA (SEQ ID NO: 4) |
| SNP_05 | 213.9 | 208949963 | CC | TT | TC | CACGACTTTGTGCAACAAAAAA CATTTTAACAGTAAATGGGCAA TTTCCAGGACCAACGTTGTATG TTCA[C/T]GAAGGAGATACAAT TTATGTCAAGGTCCATAACAAT GGAAGATACAACATCACCATTC ATTGGTATGAAA (SEQ ID NO: 5) |
| SNP_06 | 224.7 | 233786307 | AA | CC | CA | TTCTTAATTTGTCTGGGACATGA TGACATGTTCTGATCTTTGTCTT TTGACCTGTAGTCAACGGTCGA CC[A/C]CAACTACCACATGCGTT TGTTCTTAATCTTTTTCTGATCT GGTTTTTGTGTCGTTTTTTTTTC CTGAAG (SEQ ID NO: 6) |
| SNP_07 | 225.6 | 240318733 | TT | GG | GT | CGGAGCTACACGGTGTCGTTCT ACTATCTCAGCGTCAGCCCTCA GGAGTCAGGTCAGACCAACATC GCGC[G/T]TTTCTTCCCAAAAAC ATTCTTTCCTCGAAAGCCGCAA TCGATTAGGGATTCGCTCTGCT GTTTCTTCCTT (SEQ ID NO: 7) |

TABLE 2

Chromosome 6-SNP markers linked to QTL6.1

| Marker name | Position in cM | Physical position of SNP (in bases) on chromosome 7 | Genotype of Nr:1 susceptible L. sativa parent (wild type genotype) | Genotype of NCIMB42086 (Nr:1 resistant genotype-homozygous | Genotype heterozygous (Nr:1 resistant genotype heterozygous | Sequence comprising SNP |
| --- | --- | --- | --- | --- | --- | --- |
| SNP_08 | 94.2 | 72772104 | CC | TT | TC | ATGTAAACTGAACCAAAAAGG CTAATCTTCCGCTTAACAACTG TAAAGCTTCTAGTGTAAATAAA GATAC[C/T]AACCCCAATTTCTC CTGATTCCATTGTGCTTAGCTCG AAATCAACCAATTGCAAACTCA ACAATCTATCA (SEQ ID NO: 8) |

TABLE 2-continued

Chromosome 6-SNP markers linked to QTL6.1

| Marker name | Position in cM | Physical position of SNP (in bases) on chromosome 7 | Genotype of Nr:1 susceptible L. sativa parent (wild type genotype) | Genotype of NCIMB42086 (Nr:1 resistant genotype-homozygous | Genotype heterozygous (Nr:1 resistant genotype heterozygous | Sequence comprising SNP |
|---|---|---|---|---|---|---|
| SNP_09 | 83.3 | 93428084 | TT | CC | CT | TATATATTAAAATCAAAAAGT TATTGATTTGATATAGTTATTTG TTTTGGCTTTAAAGTACGTACA AAA[C/T]CAATTCATTGCCAATC AAAGACAATGGTGTTCTGGTTT TCATACTAGTGGGCACATACGA CTGCATGGAG (SEQ ID NO: 9) |
| SNP_10 | 77.6 | 107614854 | GG | AA | AG | ATTTGGTACCAAAACTTTACAA TTTATACATTTACAAATTGAAG AAACCTGCGTGTTGCATCAATT GATA[A/G]GAATTGGTAACAAA TTGAGCCATTTGTTTTATCTGCA TAACTCGGTAAAAACTTCTCTT GTTTGCATAAA (SEQ ID NO: 10) |
| SNP_11 | 75.7 | 109323191 | AA | CC | CA | TCACCTCTGAAAGAAATTCAGC TTCTCCTTGTTGTGATTTGTCAA GAGCCAATTTCTTTATAGCAAC TAG[A/C]AGCCCATCTTCTAATT TACCCTATTAAAAGCCCTTAAA AGTCATATATATCTCTCTACCTT GAACAGCGT (SEQ ID NO: 11) |
| SNP_12 | 48.4 | unknown | TT | CC | CT | GTATATATATATTATAACCCAG ACAAGTCTATTACAGCACCTCA ATAGAACGATAAAGACTCACAT AGTC[C/T]GTAAATGTTTCTCCC ACAATGCCTCCACCATCTTCCT CTCGTTCCACTTCAATTGCTACC TGAATAGGTTT (SEQ ID NO: 12) |
| SNP_13 | 48.4 | unknown | AA | GG | GA | GGAGATGGAGCTGGCCCTATGC ATTTCAAAACAAGCAACAAGTA TTATATAGCCTATCTCACTACC ATTTTATAACGATTCTGAATCTG AATGGGTTGATACACAAGCGTA AAAGAAGCCATTCAAGAGAAC ATT[A/G]AAATGATTATTACCTG CCGAAGGA (SEQ ID NO: 13) |
| SNP_14 | 45.1 | 146394823 | TT | CC | CT | CTTGCTCCTTTGCAGCTTTGTTA GCTTCCGCTTGCTTTTAGCCTT CTCTTTTTCCATCTCTCTCTTCG C[C/T]CGTTCTTTCTCTTTTGCA GCTTTATCCTCTTCCCTTTTCTT TTTTGCCTCTTCTTTTTCTTTTTC TTTAT (SEQ ID NO: 14) |

TABLE 3

Chromosome 7-SNP markers linked to QTL7.1

| Marker name | Position in cM | Physical position of SNP (in bases) on chromosome 7 | Genotype of Nr:1 susceptible L. sativa parent (wild type genotype) | Genotype of NCIMB42086 (Nr:1 resistant genotype-homozygous | Genotype heterozygous (Nr:1 resistant genotype heterozygous | Genomic secquence comprising SNP |
|---|---|---|---|---|---|---|
| SNP_15 | 41.5 | 170366427 | AA | TT | TA | AATTGTGAAATCTCCATAAATG TTTTAGGTGATGAAAAAGGAT TGAGTGAGGACCCCTGATCAAA TTGG[A/T]CAAAAATCCACTCG ATCTCTTTGAATATGTCAAAGA GTTTGTATGCCAAAAACCTGCA AATGGAAAATAA (SEQ ID NO: 15) |
| SNP_16 | 33.5 | 196777876 | AA | GG | GA | ATTTTCGTGGTATATTTCTATCA ATCAGTGCTATAAAATATCATC AGAAAATATGTGAATGATTTTA GAT[A/G]TTAAACATATATATGG TGGAGATTTTAGTGTTAGAGG AATAGAGATAAGGTGGTATTCT AACGAAAGCG (SEQ ID NO: 16) |
| SNP_17 | 29.6 | 208734444 | CC | TT | TC | GGGGCAAAAGTGTCCTTACGTA TTGAGCACGAAAGAGAATTCTC TGTTCGCTATTGCACAAGTCTA CAGC[C/T]AGCTGTTTAAGGAA CACTTTTCGGTTGAGTTGCTTTG GAGATGTTATATCCAAATCCAT TGATCCACTTG (SEQ ID NO: 17) |
| SNP_18 | 29.6 | 212123542 | CC | GG | GC | TTGTATATTTAATCGACTTTGTA AGACTTTATTTGCCTAGCTTCA AGCTTGCTTTTTATTTATAAAAC TT[C/G]CTGTCTTTTCGATTGGT TAAATCACAAACTTTGGCTGCT TCAAGTCTTTCATTTTAATCTCT AGTCTAAC (SEQ ID NO: 18) |
| SNP_19 | 27.3 | 218612262 | AA | GG | GA | ATGTTCATCCATGTATTACACT ATTATTGTTTGTTTATGCATTGA TTTTCACTGTTTGTAGTTCTTTT AT[A/G]TCACTAGAACAATGRM ATCCTTGAARGCTTTAGTGCAT CAGATCAAGCTTCAACACTCCA GTTCATTAAG (SEQ ID NO: 19) |
| SNP_20 | 22.9 | unknown | CC | TT | TC | CCATGWGTGTTTCTTCTTCCTCC TGCTGAAGATTTTCAGGAATTA CGCTCTCTTCAATTTTCTCTTCA TTC[C/T]TAAAAGATTCTTCATC TTCATCTTCTTCTTCCTCTTCGT TTTTCTCCRTATTTGGTTCCCAG AATCGATT (SEQ ID NO: 20) |
| SNP_21 | 16.7 | unknown | AA | CC | CA | CAACCACCCACMCCCAACGTTC TATCTGGCCAGATGAACT[A/C] ACGACAAGTCTTGAGATGACAG AAGAATTGATAAGAGAATAACT GTAAGACACCTCCGTTGCATTA ATAACCATGTCGGC (SEQ ID NO: 21) |
| SNP_22 | 13.8 | 232806419 | TT | CC | CT | CAGAGAGGGGTGTTTTGCTTCT TGAAAATGTCAGATTCTATAAG GAGGAAGAAAAGAACGATCCT GAATT[C/T]GCAAAGAAGCTTG CATCACTAGCAGACCTGTATGT |

TABLE 3-continued

Chromosome 7-SNP markers linked to QTL7.1

| Marker name | Position in cM | Physical position of SNP (in bases) on chromosome 7 | Genotype of Nr:1 susceptible L. sativa parent (wild type genotype) | Genotype of NCIMB42086 (Nr:1 resistant genotype-homozygous | Genotype heterozygous (Nr:1 resistant genotype heterozygous | Genomic secquence comprising SNP |
|---|---|---|---|---|---|---|
| | | | | | | TAATGATGCATTTGGCACTGCA CATAGAGCACATG (SEQ ID NO: 22) |

Example 4—QTL Mapping of Nr: 1 Resistance

New phenotyping and marker analysis was carried out in two backcross populations to map Nr:1 resistance. Phenotyping was carried out as described above.

Two QTLs with significant LOD score were mapped on chromosome 6 and chromosome 7, comprising QTL6.1 and QTL7.1. Results are also shown in FIG. 3B.

TABLE 4

Chromosome 6-SNP markers linked to QTL6.1

| Marker name | Physical position of SNP (in bases) on chromosome 6 | Genotype of Nr:1 susceptible L. sativa parent (wild type genotype) | Nr:1 resistant genotype (homozygous) | Nr:1 resistant genotype (heterozygous) | Genomic secquence comprising SNP |
|---|---|---|---|---|---|
| SNP1.23 | 77007835 | TT | CC | TC | CATAAATAATAATTCGCTAATA CCCCCTGCAGTGCAAACGGGA GGGGAATCCTGGATGTTCAAG CTGGAT[T/C]GAAACTCTAGAA AAAGAGGTGATGGAATACTTT AGTGAAAATKTTAACATATTG AGAAGATGATGGYACA (SEQ ID NO: 23) |
| SNP_02 | 117931305 | TT | CC | CT | AATCAACATCAAGCCTCTTCAA GCTAGCTTCACAACAAGCCCTC ACGTACTCAGGTTCCCCGTGGA CTTC[C/T]GATTGACCGATTGTT TCCCCAAATTTGATCCCAAATT TCGTGGCTAATTGAACATCCTC TCTCTTCACTC (SEQ ID NO: 2) |
| SNP2.24 | 145870505 | CC | TT | CT | TGCATACATACCTTAGGCAATT GGTAGCTGATGTTGAATTCTCA ATTGGTTGGAACTCTAAATGCT TCCT[C/T]AAAGTTCGTAAAAG AGAAACATGAATAGAATCAAT CAATAAGSTAGGAGACTTGCTT CTAATGGATGCCA (SEQ ID NO: 24) |
| SNP_03 | 161579227 | CC | AA | AC | TAGGGTTTGCGAACAAGATCG AGTTGCCGGAGATTCTCCAAG GACTGCTCTTGGCATCTTCCGA CGACAG[A/C]GGTCTTGCTCTC ACTGCGACGTTGATTCTCTCCA TGGTTGCTCGGATTGGAGTAG GTGGAGAGAGGGTTT (SEQ ID NO: 3) |

TABLE 5

Chromosome 7-SNP markers linked to QTL7.1

| Marker name | Physical position of SNP (in bases) on chromosome 6 | Genotype of Nr:1 susceptible L. sativa parent (wild type genotype) | Nr:1 resistant genotype (homozygous) | Nr:1 resistant genotype (heterozygous) | Genomic secquence comprising SNP |
|---|---|---|---|---|---|
| SNP_17 | 208734444 | CC | TT | TC | GGGGCAAAAGTGTCCTTAC GTATTGAGCACGAAAGAGA ATTCTCTGTTCGCTATTGCA CAAGTCTACAGC[C/T]AGCT GTTTAAGGAACACTTTTCG GTTGAGTTGCTTTGGAGAT GTTATATCCAAATCCATTG ATCCACTTG (SEQ ID NO: 17) |
| SNP17.25 | 211928662 | CC | TT | CT | CGCATCATCGACCTCTCAT TTAATTCATTTTCTGGTGAT CTGCCACATCAGTACTTCC AGGATTGGTCAG[C/T]AAT GAAGGAGACAAAACAAAA TGCAGCATATATGCAAKCA AATGTTGATATTTTGGGGG AAARGTACATC (SEQ ID NO: 25) |
| SNP_18 | 212123542 | CC | GG | GC | TTGTATATTTAATCGACTTT GTAAGACTTTATTTGCCTA GCTTCAAGCTTGCTTTTTAT TTATAAAACTT[C/G]CTGTC TTTTCGATTGGTTAAATCAC AAACTTTGGCTGCTTCAAG TCTTTCATTTTAATCTCTAG TCTAAC (SEQ ID NO: 18) |
| SNP_19 | 218612262 | AA | GG | GA | ATGTTCATCCATGTATTAC ACTATTATTGTTTGTTTATG CATTGATTTTCACTGTTTGT AGTTCTTTTAT[A/G]TCACT AGAACAATGRMATCCTTGA ARGCTTTAGTGCATCAGAT CAAGCTTCAACACTCCAGT TCATTAAG (SEQ ID NO: 19) |

QTL6.1 and QTL7.1 were identified in two different Nr:1 resistant *L. virosa* accession types and accession specific markers, which can distinguish introgressions and origin of the introgression were identified. Markers VSP1 and VSP2 are identified in one accession type, represented by NCIMB42086, and markers VSP3 and VSP4 in another accession type.

TABLE 6

L. virosa accession specific markers for QTL6.1

| Marker name | Physical position of SNP (in bases) on chromosome 6 | Genotype of Nr:1 susceptible L. sativa parent (wild type genotype) | Nr:1 resistant genotype (homozygous) | Nr:1 resistant genotype (heterozygous) | Genomic secquence comprising SNP |
|---|---|---|---|---|---|
| VSP1 | 79356899 | TT | GG | GT | TTCATGCTTCTCACTCCATGTGTAAGTA GCTCCTTTATGGGTAAATGGTGTCAAC GGAACAACAACTGAA[G/T]AAAATCCT TAGATAAACCTTTTGTAACATCCAACT AATCCTAGGATACTACAAGTCTCAGTG GGACTTTT (SEQ ID NO: 26) |
| VSP3 | 79357567 | CC | AA | AC | AAAGTGCATAGTCTTGTGAGCTTCTTC CATGAGAAGTTCTCTCATTCCTCCTAC |

TABLE 6-continued

*L. virosa* accession specific markers for QTL6.1

| Marker name | Physical position of SNP (in bases) on chromosome 6 | Genotype of Nr:1 suscept-ible *L. sativa* parent (wild type genotype) | Nr:1 resistant genotype (homozygous) | Nr:1 resistant genotype (heterozygous) | Genomic secquence comprising SNP |
|---|---|---|---|---|---|
| | | | | | CTTGGGCACCAAAATC[C/A]TATTTTGG AATTCGTTTAATCCTTTATTGTTTGTAC TAAATGCTAACATTTTGCCTAAACGTT CCACCTT (SEQ ID NO: 27) |

TABLE 7

*L. virosa* accession specific markers for QTL7.1

| Marker name | Physical position of SNP (in bases) on chromosome 6 | Genotype of Nr:1 suscept-ible *L. sativa* parent (wild type genotype) | Nr:1 resistant genotype (homozygous) | Nr:1 resistant genotype (heterozygous) | Genomic secquence comprising SNP |
|---|---|---|---|---|---|
| VSP2 | 203852532 | AA | CC | AC | TATAAATGTGTTGCAAGAAAACTGAAT TTCAAGAAAGCAAATGTAATCACTCTT TTTTAATTATTTGTAG[A/C]ACATCGTA CTGATCATTTTGAGAAGTTCGATCAAA AGTTTATCTATTATCCCAATTTGATCAC TTTGAAA (SEQ ID NO: 28) |
| VSP4 | 212050206 | AA | GG | AG | GTTCATCAATTTCCTTTAGCTCTTTATC AAGGAAATATTCTTTTTCCTCGTAGCG AAGGGCCATATGAAT[A/G]TTTCAGAT CCAATCGTTGAAGTTTGACCCATCGAA GATAATTCTCCCAACCAATTTCATGAG TGAGACCA (SEQ ID NO: 29) |

Example 5—Clip-on Cane Experiment

The two wild *L. virosa* accessions above comprise similarly high levels of Nr: 1 resistance, but NCIMB 42086 has an even better resistance, as development of nymphs of Nr: 1 is stopped earlier on plants of NCIMB 42086 compared to the other *L. virosa* accession, as found in a clip-on cage experiment.

The experiment was done using 1 day old nymphs. Per plant one cage containing at least 3 adult aphids was placed. One day after inoculation, all adults were removed leaving only 3 nymphs per cage. Twelve days after removal of the adult, the number of adults (survival), the number of new nymphs and skins was counted. The experiment was done in a complete randomized design with 28 replicas (1 cage/plant). The variables were transformed and analyzed with ANOVA followed by LSD test.

Survival and number of new nymphs was zero for both wild *L. virosa* accessions, while it was 0.86 (average survival) and 17.57 (average number of new nymphs) for the susceptible control. However, the wild accessions differed in the average number of shed skins (average number in NCIMB42086 was 0.85, while the average number in the other accession was 2.11, and in the susceptible control 5.85), with NCIMB42086 having a significantly lower average number of shed skins, showing that nymph development is stopped earlier in NCIMB42086.

The invention claimed is:

1. A *Lactuca sativa* plant comprising an introgression fragment from *Lactuca virosa* on chromosome 6 and/or on chromosome 7 which comprises a Quantitative Trait Locus (QTL) that confers resistance against *Nasonovia ribisnigri* biotype 1 (Nr:1), and wherein said introgression fragment on chromosome 6 comprises QTL6.1 in the region starting at 77 Mb and ending at 162 Mb of chromosome 6 and wherein said introgression fragment on chromosome 7 comprises QTL7.1 in the region starting at 203 Mb and ending at 219 Mb of chromosome 7,
   wherein said introgression fragment on chromosome 6 comprises at least 1 of the following markers:
   a) the CC or CT genotype for the Single Nucleotide Polymorphism marker SNP1.23 in SEQ ID NO: 23;
   b) the CC or CT genotype for the Single Nucleotide Polymorphism marker SNP 02 in SEQ ID NO: 2;
   c) the TT or CT genotype for the Single Nucleotide Polymorphism marker SNP2.24 in SEQ ID NO: 24; and/or
   d) the AA or AC genotype for the Single Nucleotide Polymorphism marker SNP 03 in SEQ ID NO: 3, and
   wherein the introgression fragment on chromosome 7 comprises at least 1 of the following markers:
   e) the TT or TC genotype for the Single Nucleotide Polymorphism marker SNP 17 in SEQ ID NO: 17;
   f) the TT or TC genotype for the Single Nucleotide Polymorphism marker SNP17.25 in SEQ ID NO: 25;
   g) the GG or GC genotype for the Single Nucleotide Polymorphism marker SNP 18 in SEQ ID NO: 18; and/or
   h) the GG or GA genotype for the Single Nucleotide Polymorphism marker SNP 19 in SEQ ID NO: 19.

2. The plant according to claim 1, comprising both the introgression fragment on chromosome 6 and on chromosome 7.

3. The plant according to claim 1, wherein said introgression fragment on chromosome 6 further comprises:
   i) the GG or GT genotype for the Single Nucleotide Polymorphism marker VSP1 in SEQ ID NO: 26; or
   j) the AA or AC genotype for the Single Nucleotide Polymorphism marker VSP3 in SEQ ID NO: 27.

4. The plant according to claim 1, wherein said introgression fragment on chromosome 7 further comprises:
   k) the CC or CA genotype for the Single Nucleotide Polymorphism marker VSP2 in SEQ ID NO: 28, or
   l) the GG or GA genotype for the Single Nucleotide Polymorphism marker VSP4 in SEQ ID NO: 29.

5. The plant according to claim 1, wherein the *Lactuca sativa* plant is loose-leaf lettuce, Romaine lettuce, Crisphead lettuce, Butterhead lettuce, Batavia lettuce or Stem lettuce.

6. The plant according to claim 1, wherein said introgression fragment is a fragment of chromosome 6 and/or 7 as found in *L. virosa* accession NCIMB42086.

7. A seed from which a plant according to claim 1 can be grown.

8. Leaves or heads of the plant according to claim 1.

9. A progeny plant of the lettuce plant according to claim 1, wherein said progeny plant retains the introgression fragment on chromosome 6 comprising QTL6.1 and/or chromosome 7 comprising QTL7.1.

10. The progeny plant according to claim 9, wherein the progeny plant is produced by one or more of: selfing, crossing, mutation, double haploid production or transformation.

11. A part of a lettuce plant according to claim 1, wherein the part is selected from the group consisting of: stems, cuttings, petioles, cotyledons, flowers, anthers, pollen, ovaries, roots, root tips, protoplasts, callus, microspores, stalks, ovules, shoots, seeds, embryos, embryo sacs, cells, buds, leaves, and meristems, and wherein said part comprises the introgression fragment on chromosome 6 comprising QTL6.1 and/or chromosome 7 comprising QTL7.1.

12. The plant according to claim 1, wherein said introgression fragment on chromosome 6 comprises the CC or CT genotype for the Single Nucleotide Polymorphism marker SNP_02 in SEQ ID NO: 2, and the AA or AC genotype for the Single Nucleotide Polymorphism marker for VSP3 in SEQ ID NO: 27.

13. The plant according to claim 1, wherein said introgression fragment on chromosome 7 comprises the GG or GC genotype for the Single Nucleotide Polymorphism marker for SNP_18 in SEQ ID 18, and the GG or GA genotype for the Single Nucleotide Polymorphism marker for VSP4 in SEQ ID NO: 29.

* * * * *

SEQUENCE LISTING

```
<160> NUMBER OF SEQ ID NOS: 29

<210> SEQ ID NO 1
<211> LENGTH: 141
<212> TYPE: DNA
<213> ORGANISM: Lettuce

<400> SEQUENCE: 1
tcatatggat taaccattgg tgcaaacata gctgcccctg tatataatca tcatccataa      60
atcattaaat atgtgaagtt tttataaagg tttagattgt gaacagtaaa gttacctgcg     120
```

```
attttagaag gtatgtgctt t                                              141

<210> SEQ ID NO 2
<211> LENGTH: 141
<212> TYPE: DNA
<213> ORGANISM: lettuce

<400> SEQUENCE: 2
aatcaacatc aagcctcttc aagctagctt cacaacaagc cctcacgtac tcaggttccc     60
cgtggacttc cgattgaccg attgtttccc caaatttgat cccaaatttc gtggctaatt    120
gaacatcctc tctcttcact c                                              141

<210> SEQ ID NO 3
<211> LENGTH: 141
<212> TYPE: DNA
<213> ORGANISM: lettuce

<400> SEQUENCE: 3
tagggtttgc gaacaagatc gagttgccgg agattctcca aggactgctc ttggcatctt     60
ccgacgacag aggtcttgct ctcactgcga cgttgattct ctccatggtt gctcggattg    120
gagtaggtgg agagagggtt t                                              141

<210> SEQ ID NO 4
<211> LENGTH: 141
<212> TYPE: DNA
<213> ORGANISM: lettuce

<400> SEQUENCE: 4
tagaatagat ttattgatat gttccttaat gttggcttcc aaatgttaat cataagttgt     60
accaatatgt gattaaataa gttttaattt aaatgcattg aaaggtgaaa attatactgt    120
aacaagtttg tgaatcttca a                                              141

<210> SEQ ID NO 5
<211> LENGTH: 141
<212> TYPE: DNA
<213> ORGANISM: lettuce

<400> SEQUENCE: 5
cacgactttg tgcaacaaaa aacattttaa cagtaaatgg gcaatttcca ggaccaacgt     60
tgtatgttca tgaaggagat acaatttatg tcaaggtcca taacaatgga agatacaaca    120
tcaccattca ttggtatgaa a                                              141

<210> SEQ ID NO 6
<211> LENGTH: 141
<212> TYPE: DNA
<213> ORGANISM: lettuce

<400> SEQUENCE: 6
ttcttaattt gtctgggaca tgatgacatg ttctgatctt tgtcttttga cctgtagtca     60
acggtcgacc ccaactacca catgcgtttg ttcttaatct ttttctgatc tggtttttgt    120
gtcgtttttt ttttcctgaa g                                              141

<210> SEQ ID NO 7
<211> LENGTH: 141
<212> TYPE: DNA
<213> ORGANISM: lettuce
```

<400> SEQUENCE: 7
cggagctaca cggtgtcgtt ctactatctc agcgtcagcc ctcaggagtc aggtcagacc    60
aacatcgcgc gtttcttccc aaaaacattc tttcctcgaa agccgcaatc gattagggat   120
tcgctctgct gtttcttcct t                                             141

<210> SEQ ID NO 8
<211> LENGTH: 141
<212> TYPE: DNA
<213> ORGANISM: lettuce

<400> SEQUENCE: 8
atgtaaactg aaccaaaaag gctaatcttc cgcttaacaa ctgtaaagct tctagtgtaa    60
ataaagatac taaccccaat ttctcctgat tccattgtgc ttagctcgaa atcaaccaat   120
tgcaaactca acaatctatc a                                             141

<210> SEQ ID NO 9
<211> LENGTH: 141
<212> TYPE: DNA
<213> ORGANISM: lettuce

<400> SEQUENCE: 9
tatatattaa aatcaaaaaa gttattgatt tgatatagtt atttgttttg gctttaaagt    60
acgtacaaaa ccaattcatt gccaatcaaa gacaatggtg ttctggtttt catactagtg   120
ggcacatacg actgcatgga g                                             141

<210> SEQ ID NO 10
<211> LENGTH: 141
<212> TYPE: DNA
<213> ORGANISM: lettuce

<400> SEQUENCE: 10
atttggtacc aaaactttac aatttataca tttacaaatt gaagaaacct gcgtgttgca    60
tcaattgata agaattggta acaaattgag ccatttgttt tatctgcata actcggtaaa   120
aacttctctt gtttgcataa a                                             141

<210> SEQ ID NO 11
<211> LENGTH: 141
<212> TYPE: DNA
<213> ORGANISM: lettuce

<400> SEQUENCE: 11
tcacctctga aagaaattca gcttctcctt gttgtgattt gtcaagagcc aatttcttta    60
tagcaactag cagcccatct tctaatttac cctattaaaa gcccttaaaa gtcatatata   120
tctctctacc ttgaacagcg t                                             141

<210> SEQ ID NO 12
<211> LENGTH: 142
<212> TYPE: DNA
<213> ORGANISM: lettuce

<400> SEQUENCE: 12
gtatatatat attataaccc agacaagtct attacagcac ctcaatagaa cgataaagac    60
tcacatagtc cgtaaatgtt tctcccacaa tgcctccacc atcttcctct cgttccactt   120
caattgctac ctgaataggt tt                                            142

```
<210> SEQ ID NO 13
<211> LENGTH: 160
<212> TYPE: DNA
<213> ORGANISM: lettuce

<400> SEQUENCE: 13
ggagatggag ctggccctat gcatttcaaa acaagcaaca agtattatat agcctatctc    60
actaccattt tataacgatt ctgaatctga atgggttgat acacaagcgt aaaagaagcc   120
attcaagaga acattgaaat gattattacc tgccgaagga                          160

<210> SEQ ID NO 14
<211> LENGTH: 141
<212> TYPE: DNA
<213> ORGANISM: lettuce

<400> SEQUENCE: 14
cttgctcctt tgcagctttg ttagcttccg cttgcttttt agccttctct ttttccatct    60
ctctcttcgc ccgttctttc tcttttgcag ctttatcctc ttcccttttc tttttttgcct  120 cttcttttc ttttctttta t                                              141

<210> SEQ ID NO 15
<211> LENGTH: 141
<212> TYPE: DNA
<213> ORGANISM: lettuce

<400> SEQUENCE: 15
aattgtgaaa tctccataaa tgttttaggt gatgaaaaaa ggattgagtg aggaccctg     60 atcaaattgg tcaaaatcc actcgatctc tttgaatatg tcaaagagtt tgtatgccaa   120
aaacctgcaa atggaaaata a                                             141

<210> SEQ ID NO 16
<211> LENGTH: 141
<212> TYPE: DNA
<213> ORGANISM: lettuce

<400> SEQUENCE: 16
attttcgtgg tatatttcta tcaatcagtg ctataaaata tcatcagaaa atatgtgaat    60
gattttagat gttaaacata tatatggtgg agattttag tgttagagga atagagataa   120
ggtggtattc taacgaaagc g                                             141

<210> SEQ ID NO 17
<211> LENGTH: 141
<212> TYPE: DNA
<213> ORGANISM: lettuce

<400> SEQUENCE: 17
ggggcaaaag tgtccttacg tattgagcac gaaagagaat tctctgttcg ctattgcaca    60
agtctacagc tagctgttta aggaacactt ttcggttgag ttgctttgga gatgttatat   120
ccaaatccat tgatccactt g                                             141

<210> SEQ ID NO 18
<211> LENGTH: 141
<212> TYPE: DNA
<213> ORGANISM: lettuce

<400> SEQUENCE: 18
ttgtatattt aatcgacttt gtaagacttt atttgcctag cttcaagctt gcttttatt     60
```

-continued tataaaactt gctgtctttt cgattggtta aatcacaaac tttggctgct tcaagtcttt    120
cattttaatc tctagtctaa c                                              141

<210> SEQ ID NO 19
<211> LENGTH: 141
<212> TYPE: DNA
<213> ORGANISM: lettuce

<400> SEQUENCE: 19
atgttcatcc atgtattaca ctattattgt tgtttatgc attgattttc actgtttgta    60
gttcttttat gtcactagaa caatgrmatc cttgaargct ttagtgcatc agatcaagct   120
tcaacactcc agttcattaa g                                              141

<210> SEQ ID NO 20
<211> LENGTH: 142
<212> TYPE: DNA
<213> ORGANISM: lettuce

<400> SEQUENCE: 20
ccatgwgtgt ttcttcttcc tcctgctgaa gattttcagg aattacgctc tcttcaattt    60
tctcttcatt cttaaaagat tcttcatctt catcttcttc ttcctcttcg tttttctccr   120
tatttggttc ccagaatcga tt                                             142

<210> SEQ ID NO 21
<211> LENGTH: 121
<212> TYPE: DNA
<213> ORGANISM: lettuce

<400> SEQUENCE: 21
caaccaccca cmcccaacgt tctatctggc cagatgaact cacgacaagt cttgagatga    60
cagaagaatt gataagagaa taactgtaag acacctccgt tgcattaata accatgtcgg   120
c                                                                    121

<210> SEQ ID NO 22
<211> LENGTH: 141
<212> TYPE: DNA
<213> ORGANISM: lettuce

<400> SEQUENCE: 22
cagagagggg tgttttgctt cttgaaaatg tcagattcta taaggaggaa gaaaagaacg    60
atcctgaatt cgcaaagaag cttgcatcac tagcagacct gtatgttaat gatgcatttg   120
gcactgcaca tagagcacat g                                              141

<210> SEQ ID NO 23
<211> LENGTH: 141
<212> TYPE: DNA
<213> ORGANISM: lettuce

<400> SEQUENCE: 23
cataaataat aattcgctaa tacccctgc agtgcaaacg ggaggggaat cctggatgtt     60
caagctggat cgaaactcta gaaaagagg tgatggaata ctttagtgaa aatkttaaca   120
tattgagaag atgatggyac a                                              141

<210> SEQ ID NO 24
<211> LENGTH: 141
<212> TYPE: DNA
<213> ORGANISM: lettuce

```
<400> SEQUENCE: 24
tgcatacata ccttaggcaa ttggtagctg atgttgaatt ctcaattggt tggaactcta      60
aatgcttcct taaagttcgt aaaagagaaa catgaataga atcaatcaat aagstaggag     120
acttgcttct aatggatgcc a                                               141

<210> SEQ ID NO 25
<211> LENGTH: 141
<212> TYPE: DNA
<213> ORGANISM: lettuce

<400> SEQUENCE: 25
cgcatcatcg acctctcatt taattcattt tctggtgatc tgccacatca gtacttccag      60
gattggtcag taatgaagga gacaaaacaa aatgcagcat atatgcaakc aaatgttgat     120 attttgggggg aaargtacat c                                              141

<210> SEQ ID NO 26
<211> LENGTH: 141
<212> TYPE: DNA
<213> ORGANISM: lettuce

<400> SEQUENCE: 26
ttcatgcttc tcactccatg tgtaagtagc tcctttatgg gtaaatggtg tcaacggaac      60
aacaactgaa gaaaatcctt agataaacct tttgtaacat ccaactaatc ctaggatact     120
acaagtctca gtgggacttt t                                               141

<210> SEQ ID NO 27
<211> LENGTH: 141
<212> TYPE: DNA
<213> ORGANISM: lettuce

<400> SEQUENCE: 27
aaagtgcata gtcttgtgag cttcttccat gagaagttct ctcattcctc ctaccttggg      60
caccaaaatc atattttgga attcgtttaa tcctttattg tttgtactaa atgctaacat     120
tttgcctaaa cgttccacct t                                               141

<210> SEQ ID NO 28
<211> LENGTH: 141
<212> TYPE: DNA
<213> ORGANISM: lettuce

<400> SEQUENCE: 28
tataaatgtg ttgcaagaaa actgaatttc aagaaagcaa atgtaatcac tctttttaa      60 ttatttgtag cacatcgtac tgatcatttt gagaagttcg atcaaaagtt tatctattat    120
cccaatttga tcactttgaa a                                               141

<210> SEQ ID NO 29
<211> LENGTH: 141
<212> TYPE: DNA
<213> ORGANISM: lettuce

<400> SEQUENCE: 29
gttcatcaat ttcctttagc tctttatcaa ggaaatattc ttttccctcg tagcgaaggg      60
ccatatgaat gtttcagatc caatcgttga agtttgaccc atcgaagata attctcccaa     120
ccaatttcat gagtgagacc a                                               141
```